(12) United States Patent
Takahata et al.

(10) Patent No.: US 11,961,623 B2
(45) Date of Patent: Apr. 16, 2024

(54) METHOD FOR SUPPORTING EXPERT MEETING BY USING COMPUTER, SUPPORT DEVICE, COMPUTER PROGRAM FOR SUPPORTING EXPERT MEETING, AND SUPPORT SYSTEM

(71) Applicant: SYSMEX CORPORATION, Kobe (JP)

(72) Inventors: Takayuki Takahata, Kobe (JP); Koji Ikeda, Kobe (JP); Mitsuru Taniguchi, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 592 days.

(21) Appl. No.: 17/038,376

(22) Filed: Sep. 30, 2020

(65) Prior Publication Data
US 2021/0098136 A1 Apr. 1, 2021

(30) Foreign Application Priority Data
Sep. 30, 2019 (JP) .................. 2019-180807

(51) Int. Cl.
*G16H 80/00* (2018.01)
*G06Q 10/1093* (2023.01)
*G16H 40/20* (2018.01)

(52) U.S. Cl.
CPC ......... *G16H 80/00* (2018.01); *G06Q 10/1095* (2013.01); *G16H 40/20* (2018.01)

(58) Field of Classification Search
CPC ........ G16H 80/00; G16H 10/60; G16H 15/00; G16H 70/20; G16H 70/60; G16H 20/00; G16H 40/00; G16H 40/20; G16H 50/70; G06Q 10/10; G06Q 10/06; G06Q 10/1095; G06Q 10/06311; G06Q 10/109; G06Q 10/0631

See application file for complete search history.

(56) References Cited

U.S. PATENT DOCUMENTS

| 9,965,590 B1* | 5/2018 | Zeiger ................. G16H 40/67 |
| 2015/0178452 A1* | 6/2015 | Nicolaas ............... G16Z 99/00 |
| | | 705/7.19 |
| 2017/0076046 A1* | 3/2017 | Barnes ................. G06F 40/40 |

(Continued)

FOREIGN PATENT DOCUMENTS

| JP | 2009-193157 A | 8/2009 |
| JP | 2018-533123 A | 11/2018 |

OTHER PUBLICATIONS

Raine R, Wallace I, et al. Improving the effectiveness of multidisciplinary team meetings for patients with chronic diseases: a prospective observational study. Southampton (UK): NIHR Journals Library; Oct. 2014. PMID: 25642498 (Year: 2014).*

(Continued)

*Primary Examiner* — Joseph D Burgess
(74) *Attorney, Agent, or Firm* — Crowell & Moring LLP

(57) ABSTRACT

Disclosed is a method of using a computer to support an expert meeting for interpretation of genetic information of a patient by a plurality of medical persons, the method including acquiring a test result of gene panel testing that analyzes genetic information of the patient; and outputting an operation screen that enables schedule setting of the expert meeting, based on meeting time according to the test result.

15 Claims, 67 Drawing Sheets

(56) References Cited

U.S. PATENT DOCUMENTS

2017/0098053 A1* 4/2017 Pandey ............... G16B 50/00
2019/0156914 A1 5/2019 Kato et al.

OTHER PUBLICATIONS

Soukup T. Socio-cognitive factors that affect decision-making in cancer multidisciplinary team meetings [PhD Thesis; Clinical Medicine Research]. London, UK: Imperial College London; 2017 (Year: 2017).*

Kristen P. Fishler et al.: "Experiences of a Multidisciplinary Genomic Tumor Board Interpreting Risk for Underlying Germline Variants in Tumor-Only Sequencing Results", American Society of Clinical Oncology, JCO Precision Oncology, Apr. 11, 2019, pp. 1-8, Retrieved from the Internet:URL:http://ascopubs.org/journal/po/.

The extended European search report dated Feb. 15, 2021 in a counterpart European patent application No. 20197190.0.

S. Ishikawa, "Reference 1: The current status of the gene panel tests used in Japan", The 3rd Sub-Working Group on Requirements for Designation of Cancer Genome Medicine Core Center Hospitals, etc. (tentative name), Oct. 4, 2017, Ministry of Health, Labour and Welfare, Retrieved from the Internet on Aug. 7, 2020, <URL: https://www.mhlw.go.jp/stf/shingi2/0000179778.html>.

The Japanese Office Action dated Sep. 29, 2020 in a counterpart Japanese patent application No. 2019-180807.

* cited by examiner

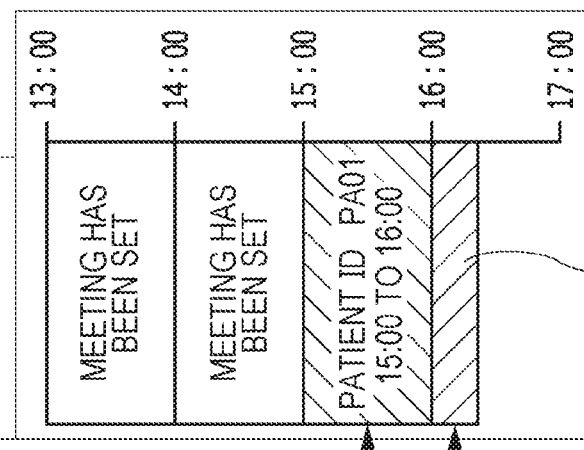

FIG. 7

MASTER TABLE M

| PATIENT ID | SAMPLE ID | TEST REQUEST ID | GENE PANEL ID | PATIENT NAME | GENDER | DATE OF BIRTH | PATIENT CONSENT | TEST REQUEST DATE | MEDICAL PERSON USER ID |
|---|---|---|---|---|---|---|---|---|---|
| PA01 | SA01 | T01 | P013 | ICHIRO TANAKA | MALE | 1977/04/14 | ... | 2018/10/10 | U01 |
| PA01 | SA02 | T01 | P013 | ICHIRO TANAKA | MALE | 1977/04/14 | ... | 2018/10/10 | U01 |
| PA02 | SA03 | T02 | P015 | Yyyyy | FEMALE | 1963/01/04 | ... | 2018/12/10 | U05 |
| PA02 | SA04 | T02 | P015 | Yyyyy | FEMALE | 1963/01/04 | ... | 2018/12/10 | U05 |
| ... | ... | ... | ... | ... | ... | ... | ... | ... | ... |

| GROUP ID | PATIENT INFORMATION | TEST RESULT | FIRST ATTRIBUTE | | SECOND ATTRIBUTE | | QUALITY INFORMATION | BUREAU FACILITY ID | HOLDING DATE AND TIME | TIME CATEGORY ID | MEETING TIME | ADDITIONAL TIME ID |
|---|---|---|---|---|---|---|---|---|---|---|---|---|
| | | | PRESENCE OR ABSENCE | COUNTS | TYPE | COUNTS | | | | | | |
| G01 | ... | ... | PRESENT | 3 | ACTIONABLE | 3 | ... | ... | ... | A | 60min | D |
| G01 | ... | ... | ABSENT | 0 | — | 0 | ... | ... | ... | | | |
| G02 | ... | ... | | | | | ... | F01 | ... | B | 10min | D |
| G02 | ... | ... | | | | | ... | | | | | |
| ... | ... | ... | ... | ... | ... | ... | ... | ... | ... | ... | ... | ... |

FIG. 8A

MASTER TABLE M

| PATIENT ID | SAMPLE ID | TEST REQUEST ID | GROUP ID | PATIENT NAME | GENDER | DATE OF BIRTH | BUREAU FACILITY ID | HOLDING DATE |
|---|---|---|---|---|---|---|---|---|
| PA04 | SA04 | T04 | G01 | XXX | MALE | 1977/04/14 | F01 | ... |

FIG. 8B

EXPERT MEETING GROUP TABLE GT

| GROUP ID | FACILITY ID | USER ID OF USER INCLUDED IN GROUP |
|---|---|---|
| G01 | F01 | U01, U02, U03, U04, U05, ... |
| G02 | F01 | U01, U04, U06, U10, U11, ... |
| G03 | F02 | U03, U08, U12, U13, U15, ... |

FIG. 9

CURRENT DATE AND TIME: 2019/01/27

TEST REQUEST — UI10 / SM / UI1 / UI3 / UI

| REQUEST DATE | TEST REQUEST ID | PATIENT INFORMATION | RESULT ATTRIBUTE INFORMATION ||||| RESULT REGISTRATION | REPORT | SETTING STATUS | HOLDING DATE AND TIME |
| | | | FIRST ATTRIBUTE || SECOND ATTRIBUTE ||| | | | |
| | | | PRESENCE OR ABSENCE | COUNTS | TYPE | COUNTS | | | | | |
| 2018/11/29 | T01 | REGISTERED | MUTATION PRESENT | 3 | ACTIONABLE | 3 | REGISTERED | OUTPUTTED | SET | 2019/01/31 10:00 |
| 2018/12/01 | T02 | REGISTERED | ① NO MUTATION | 0 | — | 0 | REGISTERED | OUTPUTTED | UNSET | — |
| 2018/12/05 | T03 | REGISTERED | MUTATION PRESENT | 1 | ① GERMLINE | 1 | REGISTERED | OUTPUTTED | SET | 2019/02/03 10:00 |
| 2018/12/07 | T04 | REGISTERED | MUTATION PRESENT | 7 | ACTIONABLE ① GERMLINE | 6 1 | REGISTERED | OUTPUTTED | SET | 2019/01/31 11:00 |
| 2018/12/14 | T05 | REGISTERED | MUTATION PRESENT |  | OTHER |  | REGISTERED | OUTPUTTED | UNSET | SET MEETING |
| 2018/12/26 | T06 | REGISTERED | UNREGISTERED |  | UNREGISTERED |  | UNREGISTERED |  | UNSET | SET MEETING |
| 2018/12/26 | T07 | REGISTERED | UNREGISTERED |  | UNREGISTERED |  | UNREGISTERED |  | UNSET | SET MEETING |
| 2019/01/07 | T08 | PARTIALLY REGISTERED | UNREGISTERED |  | UNREGISTERED |  | UNREGISTERED |  | UNSET | SET MEETING |
| 2019/01/07 | T09 | PARTIALLY REGISTERED | UNREGISTERED |  | UNREGISTERED |  | UNREGISTERED |  | UNSET | SET MEETING |
| 2019/01/11 | T10 | UNREGISTERED | UNREGISTERED |  | UNREGISTERED |  | UNREGISTERED |  | UNSET | SET MEETING |

TEST REQUEST INFORMATION

FIRST ATTRIBUTE: ATTRIBUTE OF PANEL TESTING RESULT
SECOND ATTRIBUTE: ATTRIBUTE OF PANEL TESTING RESULT

EXPERT MEETING SETTING STATUS

FIG. 22

UIa

INFORMATION OF REQUEST SOURCE FACILITY — UIa1

| FACILITY NAME UIa11 | FACILITY ID UIa13 | ADDRESS UIa15 | CONTACT UIa17 |
|---|---|---|---|
| xxx HOSPITAL | F04 | MINATO-KU, TOKYO | 03-xxxx-yyyy |

TEST REQUEST INFORMATION — UIa3

| TEST TYPE UIa31 | DOCTOR IN CHARGE OF PATIENT UIa32 | DOCTOR-IN-CHARGE USER ID UIa33 | PATIENT ID UIa34 | PATIENT CONSENT UIa35 |
|---|---|---|---|---|
| PANEL A: P013 | xxx | U 01 | PA04 | CONSENT TO TEST |

| PATIENT NAME UIa41 | PATIENT GENDER UIa42 | PATIENT DATE OF BIRTH UIa43 | | TEST FACILITY UIa44 |
|---|---|---|---|---|
| xxx | MALE | 1968/10/14 | | Gene Genesis |

| TEST REQUEST DATE UIa51 | FACILITY THAT LEADS MEETING UIa52 | ID OF FACILITY THAT LEADS MEETING UIa53 |
|---|---|---|
| 2019/01/21 | xx CANCER RESEARCH CENTER | F01 |

| SAMPLE 1 ID UIa57 | SAMPLE 2 ID UIa58 |
|---|---|
| SA01 | SA02 |

REQUEST — UIa7

FIG. 23

TEST MANAGEMENT TABLE L

| PATIENT ID | SAMPLE ID | TEST REQUEST ID | GENE PANEL ID | PATIENT NAME | GENDER | DATE OF BIRTH | PATIENT CONSENT | TEST REQUEST DATE | MEDICAL PERSON USER ID |
|---|---|---|---|---|---|---|---|---|---|
| PA01 | SA01 | T01 | P013 | ICHIRO TANAKA | MALE | 1977/04/14 | CONSENT | 2018/10/10 | U01 |
| PA01 | SA02 | T01 | P013 | ICHIRO TANAKA | MALE | 1977/04/14 | CONSENT | 2018/10/10 | U01 |
| PA02 | SA03 | T02 | P015 | Yyyyy | FEMALE | 1963/01/04 | NON-CONSENT | 2018/12/10 | U05 |
| PA02 | SA04 | T02 | P015 | Yyyyy | FEMALE | 1963/01/04 | NON-CONSENT | 2018/12/10 | U05 |
| ... | ... | ... | ... | ... | ... | ... | ... | ... | ... |

| TEST RESULT | FIRST ATTRIBUTE | | SECOND ATTRIBUTE | | QUALITY INFORMATION |
|---|---|---|---|---|---|
| | PRESENCE OR ABSENCE | COUNTS | TYPE | COUNTS | |
| ... | PRESENT | 3 | ACTIONABLE | 3 | ... |
| ... | ABSENT | 0 | — | 0 | ... |
| ... | ... | ... | ... | ... | ... |

FIG. 24

SAMPLE QUALITY INFORMATION INPUT TABLE Q

| EXTRACTION DATE | TEST REQUEST ID | FIRST SAMPLE | | SECOND SAMPLE | |
|---|---|---|---|---|---|
| | | EXTRACTED NUCLEIC ACID AMOUNT | ELECTROPHORESIS RESULT | EXTRACTED NUCLEIC ACID AMOUNT | ELECTROPHORESIS RESULT |
| 2018/11/29 | T01 | SA01:10μg | FAVORABLE | SA02:500μg | FAVORABLE |
| 2018/12/01 | T02 | SA03:5μg | FAVORABLE | SA04:250μg | FAVORABLE |
| 2018/12/05 | T03 | SA05: DETECTION LIMIT OR LESS | DETECTION LIMIT OR LESS | SA06:300μg | FAVORABLE |
| ... | ... | ... | ... | ... | ... |

FIG. 27

| (EXAMPLE) MUTATION ID | CHROM | POS | REF | ALT | Annotation |
|---|---|---|---|---|---|
| #1 | 20 | 3 | C | G | abc |
| #2 | 19 | 4 | A | T | xyz |
| #3 | xx | yy | C | G | EGFR L858R |
| #4 | aa | bb | T | A | BRAF V600E |
| ... | | | | | |
| #xx | abc | ABC | G | G]p] | ALK-EML4 FUSION |
| #yy | xyz | XYZ | T | ]p]T | ROS1-CD74 FUSION |
| ... | | | | | |

FIG. 28A

ATTRIBUTE INFORMATION INPUT — UIc

FIRST ATTRIBUTE INFORMATION — UIc1

| | SELECT | NUMBER OF MUTATIONS |
|---|---|---|
| IS GENE MUTATION OF TEST TARGET DETECTED? | YES ☑ NO ☐ | 3 |

SECOND ATTRIBUTE INFORMATION — UIc2

| | SELECT | NUMBER OF MUTATIONS |
|---|---|---|
| IS ACTIONABLE MUTATION DETECTED? | YES ☑ NO ☐ | 2 |
| IS GERMLINE MUTATION DETECTED? | YES ☑ NO ☐ | 1 |
| IS MUTATION OTHER THAN ABOVE DETECTED? | YES ☐ NO ☑ | 0 |

FIG. 28B

ATTRIBUTE INFORMATION INPUT — UId

FIRST ATTRIBUTE INFORMATION — UId1

| | SELECT | NUMBER OF MUTATIONS |
|---|---|---|
| IS GENE MUTATION OF TEST TARGET DETECTED? | YES ☑ NO ☐ | 2 |

SECOND ATTRIBUTE INFORMATION — UId2

| | SELECT | NUMBER OF MUTATIONS |
|---|---|---|
| IS ACTIONABLE MUTATION DETECTED? | YES ☑ NO ☐ | 2 |
| IS MUTATION OTHER THAN ABOVE DETECTED? | YES ☐ NO ☑ | 0 |

| PANEL ID | FIRST ATTRIBUTE INFORMATION | | SECOND ATTRIBUTE INFORMATION (MUTATION TYPE) | | | | | |
|---|---|---|---|---|---|---|---|---|
| | PRESENCE OR ABSENCE OF MUTATION | COUNTS | ACTIONABLE MUTATION | COUNTS | GERMLINE MUTATION | COUNTS | OTHER MUTATION | COUNTS |
| P001 | PRESENT | 3 | PRESENT | 2 | PRESENT | 1 | ABSENT | 0 |
| ... | ... | ... | ... | ... | ... | ... | ... | ... |
| P003 | PRESENT | 2 | PRESENT | 2 | N/A | — | ABSENT | 0 |

FIG. 29

| PANEL ID | FIRST ATTRIBUTE INFORMATION | | SECOND ATTRIBUTE INFORMATION | | |
|---|---|---|---|---|---|
| | ▶ | | ▶ | | |
| P001 | PRESENT | | ACTIONABLE MUTATION | | |
| | ABSENT | | GERMLINE MUTATION | | |
| | | | OTHER MUTATION | | |

SUMMARY REPORT

PATIENT ID:
NAME OF DOCTOR IN CHARGE:
ORGANIZATION NAME:
GENE PANEL:

DETECTED GENE MUTATION

| EGFR_L858R | BRAF_V600E | .......... | .......... |
|---|---|---|---|
| .......... | .......... | .......... | .......... |
| .......... | .......... | BRCA1_K1183R | .......... |

DETAILED REPORT

GENE MUTATION INFORMATION

| GENE NAME | MUTATION ID | CHROM | POS | REF | ALT | Annotation |
|---|---|---|---|---|---|---|
| EGFR | #1 | xx | yy | C | G | EGFRL858R |
| BRAF | #2 | aa | bb | T | A | BRAFV600E |
| ..... | ... | ... | ... | ... | ... | .......... |

GERMLINE MUTATION

| GENE NAME | MUTATION ID | CHROM | POS | REF | ALT | Annotation |
|---|---|---|---|---|---|---|
| BRCA1 | #11 | ... | ... | ... | ... | BRCA1_K1183R |

ADDITIONAL INFORMATION

| GENE MUTATION | RELATED TUMOR | APPLICABLE DRUG |
|---|---|---|
| EGFR exon 21 L858R alterations | Non-small cell lung cancer | Afatinib maleate, erlotinib hydrochloride, gefitinib, or osimertinib mesilate |
| BRAF V600E | Melanoma | Dabrafenib mesilate, trametinib dimethyl sulfoxide, or vemurafenib |
| BRCA1 K1183R | Breast cancer | |

FIG. 35A

CANDIDATE SCHEDULE TABLE MS

| GROUP ID | BUREAU FACILITY ID | TIME CATEGORY ID | CANDIDATE SLOT OF MEETING HOLDING DATE AND TIME | NUMBER OF ACCEPTABLE ENTRIES |
|---|---|---|---|---|
| G01 | FA01 | A | 2019/02/08 13:00-16:00 | 3 |
| G01 | FA01 | B | 2019/02/08 16:00-16:30 | 3 |
| ... | ... | ... | ... | ... |
| G01 | FA01 | A | 2019/02/21 13:00-16:00 | 2 |
| ... | ... | ... | ... | ... |

FIG. 35B

CANDIDATE SCHEDULE TABLE MS2

| GROUP ID | BUREAU FACILITY ID | CANDIDATE SLOT OF MEETING HOLDING DATE AND TIME | SETTING STATUS A | SETTING STATUS B | Total TIME (min) | SET TIME (min) | VACANT TIME (min) |
|---|---|---|---|---|---|---|---|
| G01 | F01 | 2019/02/08 13:00-17:00 | 0 | 0 | 240 | 0 | 0 |
| G01 | F01 | 2019/02/21 13:00-17:00 | 0 | 0 | 240 | 0 | 0 |
| ... | ... | ... | ... | ... | ... | ... | ... |

FIG. 36

CURRENT DATE AND TIME: 2019/01/27
TEST REQUEST

| REQUEST DATE | TEST REQUEST ID | PATIENT INFORMATION | RESULT ATTRIBUTE INFORMATION ||||| RESULT REGISTRATION | REPORT | SETTING STATUS | HOLDING DATE AND TIME |
| | | | FIRST ATTRIBUTE || SECOND ATTRIBUTE || | | | |
| | | | PRESENCE OR ABSENCE | COUNTS | TYPE | COUNTS | | | | |
| 2018/11/29 | T01 | REGISTERED | MUTATION PRESENT | 3 | ACTIONABLE | 3 | REGISTERED | OUTPUTTED | SET | 2019/01/31 10:00 |
| 2018/12/01 | T02 | REGISTERED | ⊖ NO MUTATION | 0 | — | 0 | REGISTERED | OUTPUTTED | UNSET | — |
| 2018/12/05 | T03 | REGISTERED | MUTATION PRESENT | 1 | ⊙ GERMLINE | 1 | REGISTERED | OUTPUTTED | SET | 2019/02/03 10:00 |

EXPERT MEETING

MEETING SCHEDULE INFORMATION

SET MEETING

FIG. 40A

MASTER TABLE M

| PATIENT ID | SAMPLE ID | DATA ID | FIRST ATTRIBUTE INFORMATION |
|---|---|---|---|
| PA01 | T01 | NO01 | PRESENT |
| ... | ... | ... | ... |
| PA02 | T03 | NO03 | ABSENT |
| ... | ... | ... | ... |

FIG. 40B

TIME CATEGORY TABLE T

| MUTATION | MEETING TIME | TIME CATEGORY ID |
|---|---|---|
| PRESENT | 60min | A |
| ABSENT | 10min | B |

FIG. 40C

CANDIDATE SCHEDULE TABLE MS

| GROUP ID | BUREAU FACILITY ID | TIME CATEGORY ID | CANDIDATE SLOT OF MEETING HOLDING DATE AND TIME | NUMBER OF ACCEPTABLE ENTRIES |
|---|---|---|---|---|
| G01 | FA01 | A | 2019/02/08 13:00-16:00 | 1 |
| G01 | FA01 | B | 2019/02/08 16:00-16:30 | 3 |
| ... | ... | ... | ... | ... |
| G01 | FA01 | A | 2019/02/21 13:00-16:00 | 2 |
| ... | ... | ... | ... | ... |

FIG. 43A

MASTER TABLE M

| PATIENT ID | SAMPLE ID | DATA ID | FIRST ATTRIBUTE INFORMATION |
|---|---|---|---|
| PA01 | T01 | N01 | PRESENT |
| ... | ... | ... | ... |

FIG. 43B

TIME CATEGORY TABLE T

| MUTATION | MEETING TIME | TIME CATEGORY ID |
|---|---|---|
| PRESENT | 60min | A |
| ABSENT | 10min | B |

FIG. 43C

CANDIDATE SCHEDULE TABLE MS2

| GROUP ID | BUREAU FACILITY ID | CANDIDATE SLOT OF MEETING HOLDING DATE AND TIME | CANDIDATE HOLDING DATE AND TIME | SETTING STATUS A | SETTING STATUS B | Total TIME (min) | SET TIME (min) | VACANT TIME (min) |
|---|---|---|---|---|---|---|---|---|
| G01 | FA01 | 2019/02/08 13:00-16:00 | | 1 | 3 | 180 | 90 | 90 |
| G01 | FA01 | 2019/02/21 13:00-16:30 | | 1 | 1 | 180 | 70 | 110 |
| ... | ... | ... | | ... | ... | ... | ... | ... |

FIG. 43D (WHEN THERE IS MUTATION)

SETTING OF EXPERT MEETING — UI55

| HOLDING DATE | NUMBER OF REMAINING ACCEPTABLE ENTRIES OF A | SELECT |
|---|---|---|
| 2019/02/08 | 1 | ☑ |
| 2019/02/21 | 1 | ☐ |
| ... | ... | |

SET — UI553

UI551 UI552

FIG. 43E (WHEN THERE IS NO MUTATION)

SETTING OF EXPERT MEETING — UI56

| HOLDING DATE | NUMBER OF REMAINING ACCEPTABLE ENTRIES OF B | SELECT |
|---|---|---|
| 2019/02/08 | 9 | ☑ |
| 2019/02/21 | 11 | ☐ |
| ... | ... | |

SET — UI563

UI561 UI562

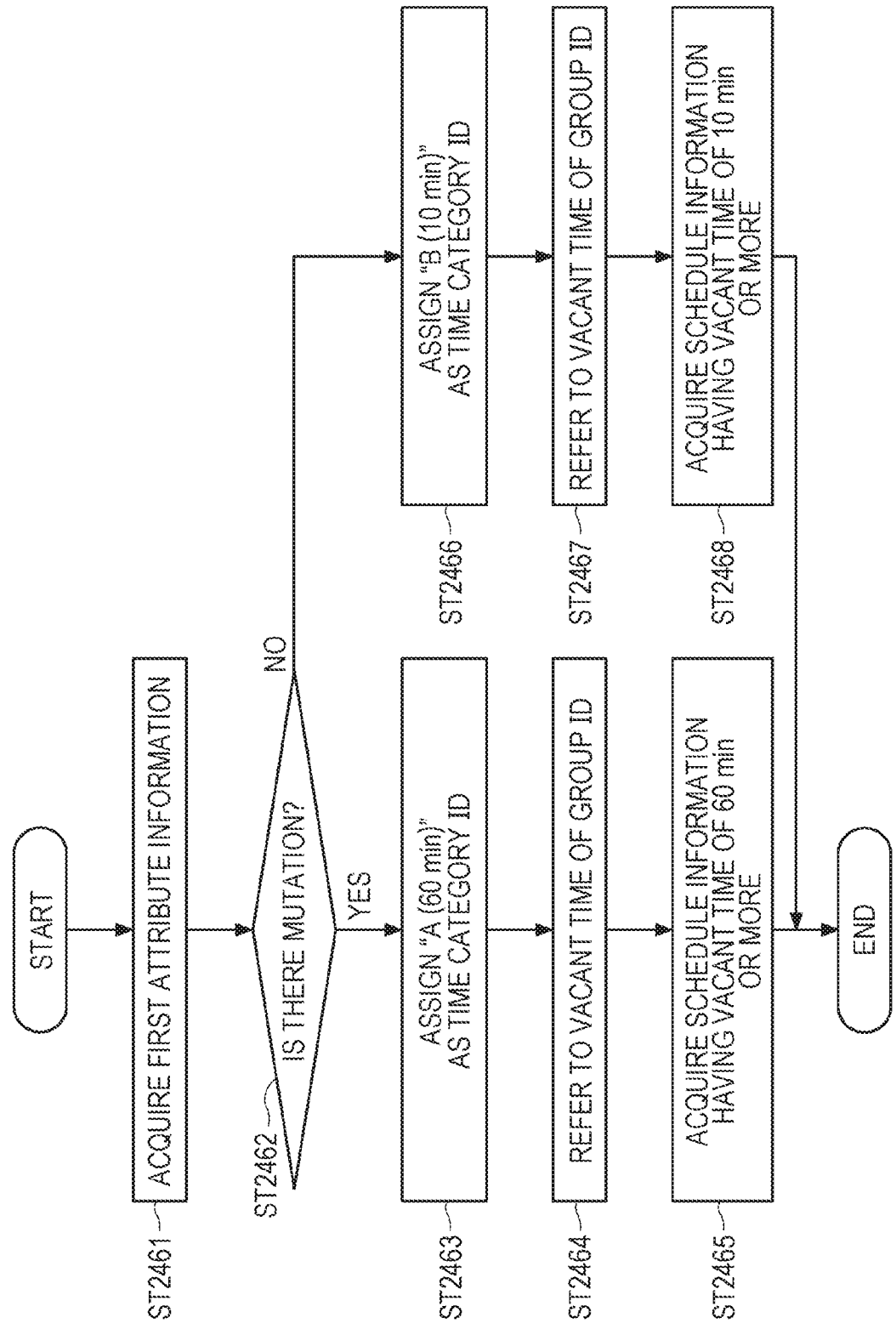

FIG. 47A

MASTER TABLE M

| PATIENT ID | TEST REQUEST ID | DATA ID | FIRST ATTRIBUTE INFORMATION | |
|---|---|---|---|---|
| | | | PRESENCE OR ABSENCE OF MUTATION | NUMBER OF MUTATIONS |
| PA01 | T01 | N01 | PRESENT | 7 |
| ... | ... | ... | ... | ... |
| PA03 | T03 | N03 | ABSENT | 0 |
| ... | ... | ... | ... | ... |

FIG. 47B

TIME CATEGORY TABLE T2

| NUMBER OF MUTATIONS | MEETING TIME | TIME CATEGORY ID |
|---|---|---|
| 1 TO 5 | 30min | A1 |
| 6 TO 10 | 60min | A2 |
| 11 TO 20 | 90min | A3 |
| 21 OR MORE | 120min | A4 |
| 0 | 10min | B |

FIG. 47C

CANDIDATE SCHEDULE TABLE MS3

| GROUP ID | BUREAU FACILITY ID | CANDIDATE SLOT OF MEETING HOLDING DATE AND TIME | SETTING STATUS | | Total TIME (min) | VACANT TIME (min) | SET TIME (min) |
|---|---|---|---|---|---|---|---|
| | | | A2 | B | | | |
| G01 | FA01 | 2019/02/08 13:00-17:00 | 2 | 3 | 240 | 90 | 150 |
| G01 | FA01 | 2019/02/21 13:00-17:00 | 1 | 1 | 240 | 170 | 70 |
| ... | ... | ... | ... | ... | ... | ... | ... |

SETTING OF EXPERT MEETING

| HOLDING DATE | NUMBER OF REMAINING ACCEPTABLE ENTRIES OF A2 | SELECT |
|---|---|---|
| 2019/02/08 | 1 | ☑ |
| 2019/02/21 | 2 | ☐ |
| ... | ... | |

UI571  UI572

SET — UI573

SETTING OF EXPERT MEETING

| HOLDING DATE | NUMBER OF REMAINING ACCEPTABLE ENTRIES OF B | SELECT |
|---|---|---|
| 2019/02/08 | 9 | ☑ |
| 2019/02/21 | 11 | ☐ |
| ... | ... | |

UI581  UI582

SET — UI583

FIG. 50A

MASTER TABLE M

| PATIENT ID | TEST REQUEST ID | DATA ID | FIRST ATTRIBUTE | SECOND ATTRIBUTE | |
|---|---|---|---|---|---|
| | | | PRESENCE OR ABSENCE OF MUTATION | MUTATION TYPE | NUMBER OF MUTATIONS |
| PA01 | T01 | N01 | PRESENT | ACTIONABLE MUTATION | 6 |
| : | : | : | : | : | : |
| PA03 | T03 | N03 | PRESENT | ACTIONABLE MUTATION GERMLINE MUTATION | 5 1 |
| : | : | : | : | : | : |

FIG. 50B

TIME CATEGORY TABLE T2

| NUMBER OF MUTATIONS | MEETING TIME | TIME CATEGORY ID |
|---|---|---|
| 1 TO 5 | 30min | A1 |
| 6 TO 10 | 60min | A2 |
| 11 TO 20 | 90min | A3 |
| 21 OR MORE | 120min | A4 |
| 0 | 10min | B |

FIG. 50C

ADDITIONAL TIME CATEGORY TABLE AD

| GERMLINE MUTATION | ADDITIONAL TIME | ADDITIONAL TIME ID |
|---|---|---|
| PRESENT | 15min | C |
| ABSENT | 0min | D |

FIG. 53A

TIME CATEGORY TABLE T2

| NUMBER OF MUTATIONS | MEETING TIME | TIME CATEGORY ID |
|---|---|---|
| 1 TO 5 | 30min | A1 |
| 6 TO 10 | 60min | A2 |
| 11 TO 20 | 90min | A3 |
| 21 OR MORE | 120min | A4 |
| 0 | 10min | B |

FIG. 53B

ADDITIONAL TIME CATEGORY TABLE AD

| GERMLINE MUTATION | ADDITIONAL TIME | ADDITIONAL TIME ID |
|---|---|---|
| PRESENT | 15min | C |
| ABSENT | 0min | D |

FIG. 53D

SETTING OF EXPERT MEETING — UI60

| HOLDING DATE | NUMBER OF REMAINING ACCEPTABLE ENTRIES OF A2 + C | SELECT |
|---|---|---|
| 2019/02/08 | 1 | ☑ |
| 2019/02/21 | 2 | ☐ |
| ... | ... | ... |

UI601  UI602

SET — UI603

FIG. 53C

CANDIDATE SCHEDULE TABLE MS3

| GROUP ID | BUREAU FACILITY ID | CANDIDATE OF MEETING HOLDING DATE AND TIME | SETTING STATUS A2 | SETTING STATUS B | Total TIME (min) | SET TIME (min) | VACANT TIME (min) |
|---|---|---|---|---|---|---|---|
| G01 | FA01 | 2019/02/08 13:00-17:00 | 2 | 3 | 240 | 150 | 90 |
| G01 | FA01 | 2019/02/08 13:00-17:00 | 1 | 1 | 240 | 70 | 170 |
| ... | ... | ... | ... | ... | ... | ... | ... |

FIG. 59

CURRENT DATE AND TIME: 2019/01/27

TEST REQUEST

U11

| REQUEST DATE | TEST REQUEST ID | TEST STATUS | PATIENT INFORMATION | RESULT ATTRIBUTE INFORMATION | QUALITY INFORMATION |
|---|---|---|---|---|---|
| 2018/11/29 | T01 | TEST COMPLETED | ... | ... | ... |
| 2018/12/01 | T02 | TEST COMPLETED | REGISTERED | NO MUTATION | REGISTERED |
| 2018/12/05 | T03 | TEST COMPLETED | ... | ... | ... |

LINK TO SAMPLE/TEST QUALITY INFORMATION

FIG. 62

CURRENT DATE AND TIME: 2019/01/27

TEST REQUEST LIST — UI1

| REQUEST DATE | TEST REQUEST ID | TEST STATUS | PATIENT INFORMATION | ... | RESULT ATTRIBUTE INFORMATION | RESULT REGISTRATION | INFORMATION DB |
|---|---|---|---|---|---|---|---|
| 2018/11/29 | T01 | TEST COMPLETED | | ... | | | |
| 2018/12/01 | T02 | TEST COMPLETED | REGISTERED | | MUTATION PRESENT  ACTIONABLE MUTATION | REGISTERED | DRUG DB CLINICAL TRIAL DB |
| 2018/12/05 | T03 | TEST COMPLETED | REGISTERED | | MUTATION PRESENT  OTHER MUTATION | REGISTERED | ARTICLE DB |

LINK TO TEST RESULT INFORMATION

LINK TO EACH INFORMATION DB

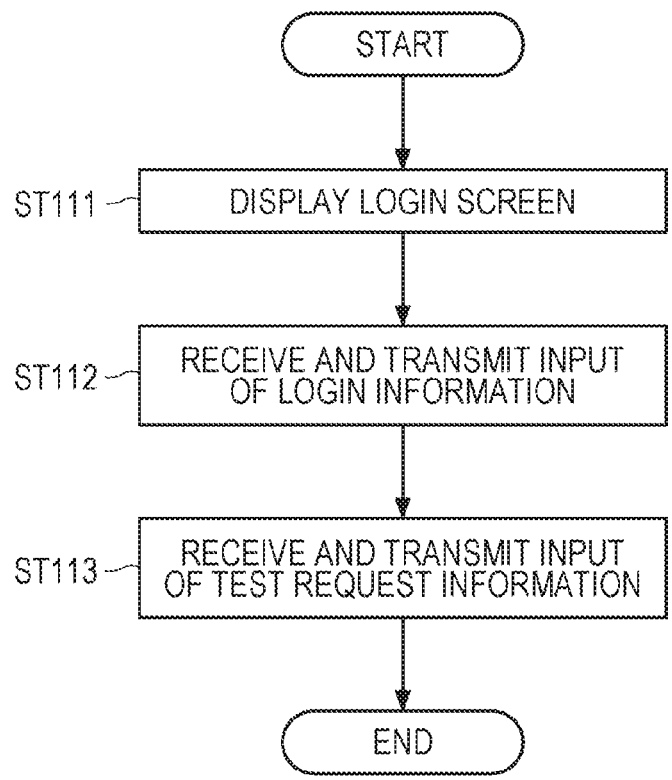

FIG. 67

CURRENT DATE AND TIME: 2019/01/27

TEST REQUEST

| REQUEST DATE | TEST REQUEST ID | TEST STATUS | PATIENT INFORMATION | RESULT ATTRIBUTE INFORMATION | | SETTING STATUS | HOLDING DATE AND TIME |
|---|---|---|---|---|---|---|---|
| 2018/11/29 | T01 | TEST COMPLETED | ... | ... | | SET | 2019/01/31 10:00 |
| 2018/12/01 | T02 | TEST COMPLETED | REGISTERED | MUTATION PRESENT | ACTIONABLE MUTATION | TEMPORARILY RESERVED | 2019/02/03 15:00 |
| 2018/12/05 | T03 | TEST COMPLETED | REGISTERED | MUTATION PRESENT | — | SET | 2019/02/03 10:00 |

UI1

EXPERT MEETING

MEETING SCHEDULE INFORMATION

SET MEETING

SETTING OF MEETING

PATIENT IDENTIFICATION INFORMATION UI71

| PATIENT NAME | GENDER | PATIENT DATE OF BIRTH |
|---|---|---|
| XXX | MALE | 1968/10/14 |

MEETING MEMBER UI73

ICHIRO TANAKA
· · ·
· · ·

SETTING OF EXPERT MEETING UI75

| HOLDING DATE | TIME ZONE | SELECT |
|---|---|---|
| 2019/01/07 | 10:00–12:00 | ☑ |
| 2019/01/07 | 13:00–15:00 | ☐ |

MEETING NOTIFICATION — UI77

METHOD FOR SUPPORTING EXPERT MEETING BY USING COMPUTER, SUPPORT DEVICE, COMPUTER PROGRAM FOR SUPPORTING EXPERT MEETING, AND SUPPORT SYSTEM

RELATED APPLICATIONS

This application claims priority to Japanese Patent Application No. 2019-180807, filed on Sep. 30, 2019, the entire content of which is incorporated herein by reference.

BACKGROUND OF THE INVENTION

1. Field of the Invention

The present specification discloses a method for supporting an expert meeting by using a computer, a support device, a computer program for supporting an expert meeting, and a support system.

2. Description of the Related Art

In recent years, in cancer treatment, research on cancer genomic medicine is being promoted in which, for each patient, gene panel testing is performed that can comprehensively investigate many gene mutations at once with a next-generation sequencer and the like, to formulate a treatment strategy suitable for each patient based on a result.

However, in general, a patient's electronic medical record, pathological image, and various test results of gene panel testing that serve as a reference in formulating a treatment strategy suitable for each patient are individually managed by different systems in a medical facility. WO2017042396 discloses an information platform that supports formulation of a treatment plan for a patient by aggregating an electronic medical record, a pathological image, a test result such as of gene panel testing, and the like dispersed in a medical facility.

In genomic medicine, a treatment strategy is formulated by holding an expert meeting including a genetic counselor, a molecular genetics researcher, a clinical technologist, a bioinformatician, and the like, in addition to a doctor in charge of a patient and a pathologist. Required time for the expert meeting may vary in accordance with a test result of gene panel testing. For example, for a patient with an actionable mutation having a therapeutic agent or a germline mutation detected, and a patient with multiple somatic mutations detected, the required time for the expert meeting tends to be longer. Whereas, for a patient with no gene mutation detected, the expert meeting may end after confirming that there is no problem in accuracy of the test and reporting an analysis result that there is no mutation. Therefore, the required time may vary greatly depending on the mutation detection result.

Since the expert meeting is often held for multiple tests on the same day, and attendees and the required time may differ for each test, it is required to devise a smooth operation.

Under such circumstances, there is a demand for a method, a support device, a computer program, and a support system for supporting a smooth operation of an expert meeting in genomic medicine.

Therefore, it is an object to provide a method, a support device, a computer program, and a support system for improving efficiency of the entire operation of genomic medicine that handles multiple test requests.

SUMMARY OF THE INVENTION

The scope of the present invention is defined solely by the appended claims, and is not affected to any degree by the statements within this summary.

One embodiment of the present invention relates to (1) a method for supporting an expert meeting for interpretation of genetic information of a patient by a plurality of medical persons by a computer. The method includes acquiring a test result of gene panel testing that analyzes genetic information of the patient, and outputting an operation screen that enables schedule setting of the expert meeting on the basis of meeting time according to the test result.

One embodiment of the present invention relates to (2) a support device (A in FIG. 4) that supports an expert meeting for interpretation of genetic information of a patient by a plurality of medical persons. A control unit (100A in FIG. 5) of the support device (A in FIG. 4) acquires a test result of gene panel testing that analyzes genetic information of the patient. Then, the control unit outputs an operation screen that enables schedule setting of the expert meeting on the basis of meeting time according to the test result.

One embodiment of the present invention relates to (3) a computer program for supporting an expert meeting for interpretation of genetic information of the patient by a plurality of medical persons. The computer program causes a computer (A in FIG. 4) to execute a step of acquiring a test result in gene panel testing that analyzes genetic information of a patient (step ST35 in FIG. 19), and a step of outputting an operation screen that enables schedule setting of the expert meeting to another computer on the basis of meeting time according to the test result (step ST243 of FIG. 39).

One embodiment of the present invention relates to (4) a support system (1000 in FIG. 4) that supports an expert meeting for interpretation of genetic information of a patient by a plurality of medical persons. The support system (1000 in FIG. 4) includes a support device (A in FIG. 4) including a control unit (100A in FIG. 5), and one or more computers (B15, B25, B35, C15, SP11, SP15 in FIG. 4). The control unit (100A in FIG. 5) of the support device (A in FIG. 4) acquires a test result of gene panel testing that analyzes genetic information of the patient. The control unit (100A in FIG. 5) outputs an operation screen [dialog UI51 in FIG. 3A, dialog UI52 in FIG. 3B, dialog UI55 in FIG. 43D, dialog UI56 in FIG. 43E, dialog UI57 in FIG. 47D, dialog UI58 in FIG. 47E, dialog UI60 in FIG. 53D] that enables schedule setting of the expert meeting on the basis of meeting time according to the test result, to one or more other computers (B15, B25, B35, C15, SP11, SP15 in FIG. 4). One or more computers (B15, B25, B35, C15, SP11, SP15 in FIG. 4) acquire and display an operation screen [dialog UI51 in FIG. 3A, the dialog UI52 in FIG. 3B, the dialog UI55 in FIG. 43D, the dialog UI56 in FIG. 43E, the dialog UI57 in FIG. 47D, the dialog UI58 in FIG. 47E, the dialog UI60 in FIG. 53D].

The above configurations (1) to (4) enable setting of meeting time according to a test result, in a schedule setting of an expert meeting whose meeting time has been set uniformly before.

A method, a support device, a computer program, and a support system can be provided to support a smooth operation of an expert meeting.

BRIEF DESCRIPTION OF THE DRAWINGS

FIG. 3A shows an example of dialog UI51, which is an operation screen for schedule setting of an expert meeting;

FIG. 3B shows an example of dialog UI52, which is an operation screen for schedule setting of an expert meeting;

FIG. 3C shows an example of a time slot MT to manage a schedule of meeting time;

FIG. 7 shows an outline of a master table M;

FIG. 8A shows an example of a part of the master table M;

FIG. 8B shows an outline of an expert meeting group table GT linked to a "group ID" field of the master table M;

FIG. 9 shows a display example of a test request list;

FIG. 22 shows an example of a graphical user interface UIa that is for making a test request;

FIG. 23 shows an outline of a test management table L;

FIG. 24 shows an outline of a sample quality information input table Q in which sample quality information is recorded;

FIG. 27 shows an example of a test result outputted in mutation analysis;

FIG. 28A shows an example of a graphical user interface UIc that is for acquiring attribute information;

FIG. 28B shows an example of a graphical user interface UId that is for acquiring attribute information;

FIG. 28C shows an example of a test management table L to which attribute information has been inputted;

FIG. 29 shows an example of a list for acquiring attribute information;

FIG. 33 shows a report format;

FIG. 35A shows a form of a candidate schedule table MS;

FIG. 35B shows a form of a candidate schedule table MS2;

FIG. 36 shows an example of a test request list UI1 when an expert meeting is set from a test request list outputted from the integrated data management device A;

FIGS. 40A to 40C show an outline of pattern 1 of a candidate schedule output process, FIG. 40A shows a part of the master table M, FIG. 40B shows a time category table T, FIG. 40C shows the candidate schedule table MS;

FIGS. 43A to 43E show an outline of pattern 2 of the candidate schedule output process, FIG. 43A shows a part of the master table M, FIG. 43B shows the time category table T. FIG. 43C shows the candidate schedule table MS2, FIG. 43D shows an example of dialog when there is a mutation, FIG. 43E shows an example of dialog when there is no mutation;

FIG. 44 shows a flowchart of pattern 2;

FIGS. 47A to 47E show an outline of pattern 3 of the candidate schedule output process, FIG. 47A shows a part of the master table M, FIG. 47B shows a time category table T2, FIG. 47C shows a candidate schedule table MS3, FIG. 47D shows an example of dialog when there is a mutation, FIG. 47E shows an example of dialog when there is no mutation;

FIGS. 50A to 50C show an outline of pattern 4 of the candidate schedule output process, FIG. 50A shows a part of the master table M, FIG. 50B shows the time category table T2, FIG. 50C shows an additional time category table AD;

FIG. 53A shows the time category table T2;

FIG. 53B shows the additional time category table AD;

FIG. 53C shows the candidate schedule table MS3;

FIG. 53D shows an example of dialog when there is a mutation;

FIG. 55A shows a part of the master table M, FIG. 55B shows the time category table T, FIG. 55C shows a meeting schedule time slot MT2;

FIG. 59 shows an example of the test request list UI1 for display of quality information from a test request list outputted from the integrated data management device A;

FIG. 62 shows an example of the test request list UI1 when an external database is displayed from a test request list outputted from the integrated data management device A;

FIG. 65 shows an example of an authentication process when a test request is made;

FIG. 66 shows an example of a login information table P;

FIG. 67 shows a modified example of the test request list UI1 when an expert meeting is set from a test request list outputted from the integrated data management device A; and FIG. 68 shows an example of dialog UI7 that is for displaying a meeting schedule.

DETAILED DESCRIPTION OF THE PREFERRED EMBODIMENTS

Figure 1:
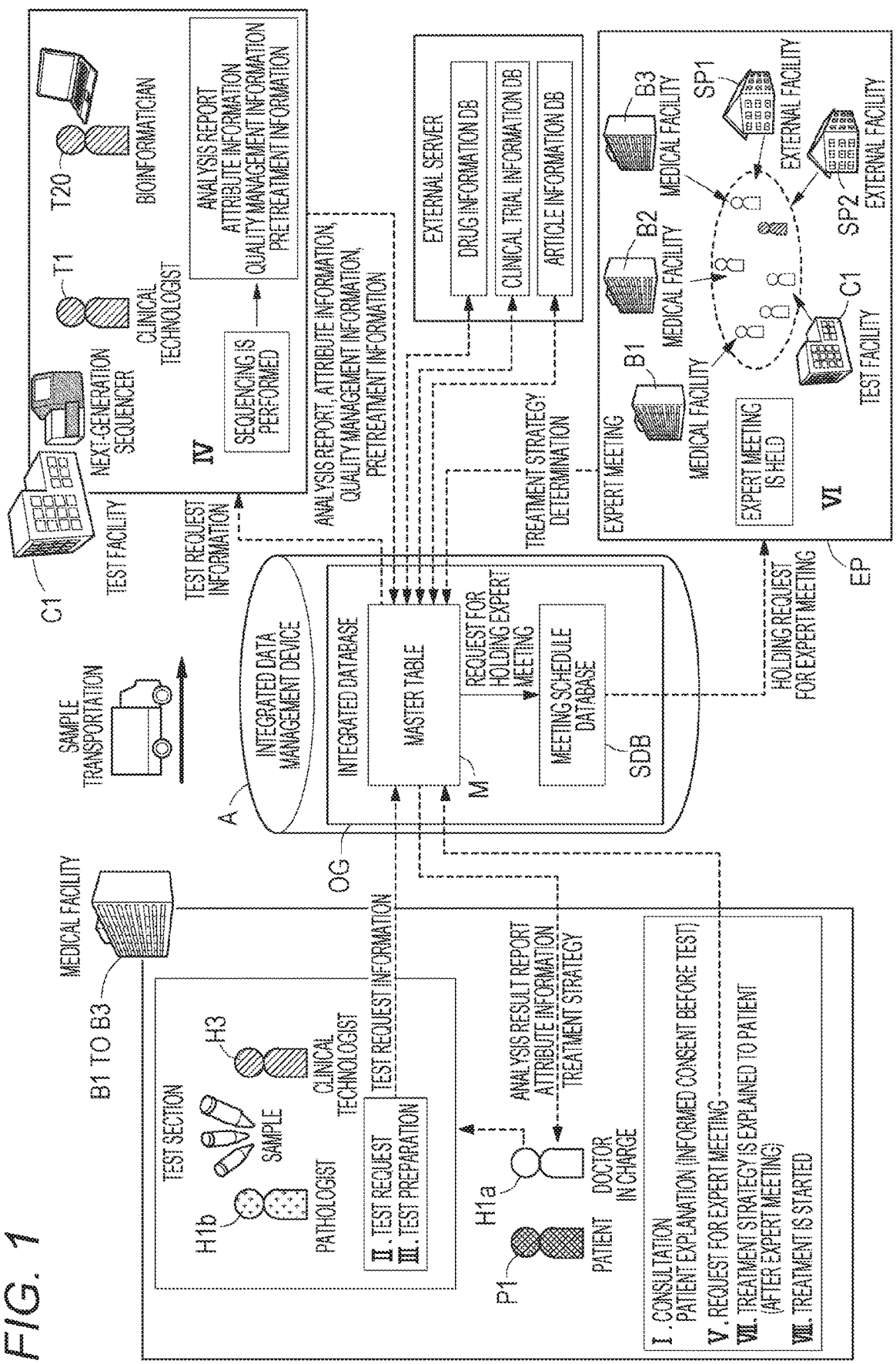
FIG. 1 shows a flow of gene panel testing.

Hereinafter, an embodiment for carrying out the invention will be described in detail with reference to the accompanying drawings. In the following description and drawings, the same reference numerals denote the same or similar components, and thus the description of the same or similar components will be omitted.

I. Outline of Embodiment

One embodiment relates to a method, a support device, a computer program, and a support system for supporting a smooth operation of an expert meeting.

First, an outline of the present embodiment will be described with reference to FIGS. 1 to 3A to 3C.

Analysis of a nucleic acid sequence of a patient sample is performed, for example, for the purpose of detecting a mutation in a nucleic acid sequence present in a tumor cell, in order to predict an effect of an anticancer drug on the tumor cell and a prognosis.

In the present specification, "nucleic acid sequence mutation" is a concept including nucleotide substitution, insertion, deletion, gene fusion, and the like. The nucleic acid sequence mutation may include a synonymous mutation that does not affect an amino acid sequence and a non-synonymous mutation that affects an amino acid sequence. The mutation to be detected is desirably a non-synonymous mutation. The non-synonymous mutation is a mutation that causes a structural abnormality of protein. The non-synonymous mutation is considered to be associated with tumorigenesis of a cell.

Mutations may be classified into two types depending on whether the mutation has occurred in a germ cell before fertilization or after fertilization. A mutation that has occurred in a somatic cell is called a somatic mutation, and a mutation that has occurred in a germ cell is called a germline mutation. Unlike the somatic mutation, the germline mutation may be inherited to the next generation of an individual. Therefore, when a patient to be applied with the method of the present embodiment inherits the germline mutation from a parental generation, even a sample prepared from a somatic cell also contains the germline mutation.

In addition to the classification nucleic acid sequence mutations as described above, mutations can be classified in accordance with reactivity to anticancer drug treatment. For example, even if there is a somatic mutation or a germline mutation that causes a disease, a mutation may be generally called an actionable mutation when the mutation can be expected to have therapeutic efficacy of 3A or more shown in "Clinical practice guidance for next-generation sequencing in cancer diagnosis and treatment" published jointly by the Japanese Society of Medical Oncology, the Japan Society of Clinical Oncology, and the Japanese Cancer Association.

Analysis of a nucleic acid sequence of a cancer-related gene by using a patient's cancer tissue sample is important for identification of an effective anticancer drug or the like against a cancer held by the patient. In gene panel testing, it is possible to simultaneously analyze several tens to several hundreds of genes in one test. A result of gene panel testing is not interpreted by a doctor in charge of the patient alone, but is interpreted by an expert meeting (also called an expert panel) including a pathologist who performs tissue diagnosis, a clinical technologist and/or a bioinformatician who conducts gene panel testing, a genetic counselor and/or a molecular genetics researcher who is an expert in gene mutation interpretation, and the like, in addition to the doctor in charge. The expert meeting determines an appropriate treatment strategy for the patient subjected to the gene panel testing.

A test request for gene panel testing is made from each medical facility, but the expert meeting is often held by one base institution in each region. Therefore, results of gene panel testing for which test requests have been made individually and for each patient by multiple medical facilities in the region will be aggregated in one expert meeting.

Therefore, in order to efficiently manage a large number of requests for gene panel testing, one embodiment provides a method for managing a test request for gene panel testing. The method includes using a computer to acquire, for each of a plurality of test requests for gene panel testing, information regarding the test request, and an attribute indicating an outline of a test result in the gene panel testing; and outputting display information for displaying a plurality of the test requests and the attribute in association with each other.

FIG. 1 shows a flow of gene panel testing in the present embodiment.

In FIG. 1, the flow of the gene panel testing will be described with use of three organizations as an example. A first organization involved in the gene panel testing is a medical facility B1 such as a hospital where a cancer patient actually visit. A second organization is a test facility C1 in which the gene panel testing is actually conducted. A third organization is an expert meeting EP. The three organizations may share information through an integrated data management device A that is for sharing information in each organization.

In gene panel testing (hereinafter, also simply referred to as a test), a patient P1 having a tumor visits the medical facility B1, and a doctor in charge H1a explains details and a flow of gene panel testing. In the explanation, informed consent is also acquired regarding whether the patient P1 or a his/her family wishes to be informed of a result in case of incidental finding such as finding of a germline mutation in the test (I in FIG. 1).

When the patient P1 consents to carry out the gene panel testing, the doctor in charge H1a requests the gene panel testing (II in FIG. 1). Information regarding the test request is transmitted to the integrated data management device A and recorded in a master table M together with patient information. The information regarding the test request may include information such as a test request date, test identification information (ID), a test panel number, a sample type, and information regarding a patient (patient information). The patient information may include patient identification information (ID), a patient name, gender, age, a pathological diagnosis result, a patient medical history, a patient family history, and the like.

When the test is requested, a sample required for the test is collected at the medical facility B1 (III in FIG. 1). As the sample, a sample containing a tumor cell and a sample containing a non-tumor cell are usually collected for one patient. The sample may be collected by a pathologist H1b or a clinical technologist H3. The collected sample is transported to the test facility C1.

At the test facility C1, a clinical technologist T1 performs pretreatment of the sample, performs sequencing of a nucleic acid sequence contained in the sample by using a next-generation sequencer, to carry out the gene panel testing (IV in FIG. 1). After the test is carried out, the clinical technologist T1 and a bioinformatician T20 cooperate with each other to create a test report (also referred to as a report). In addition to this, information regarding a test status such as pretreatment information indicating a test progress status, quality information regarding quality of the test and the sample, and attribute information indicating an outline of a test result (hereinafter, may be simply referred to as "attribute information" or "attribute") is generated. The attribute information may include first attribute information regarding the presence or absence of a mutation relating to a predetermined gene, and second attribute information relating to a mutation type. The test result of the gene panel testing, the pretreatment information, the test and sample quality information, and the attribute information are transmitted to the integrated data management device A, and recorded in the master table M in association with the information regarding the test request and the patient information. The test report may be returned to the medical facility B1 that has requested the test in a paper medium.

Figures 2A, 2B, 2C:
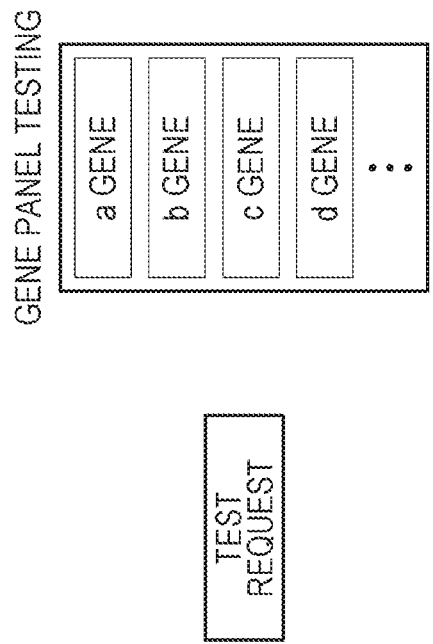
FIG. 2A shows a test request.
FIG. 2B shows an example of genes to be tested in the gene panel testing.
FIG. 2C shows a relationship between a test result and required time for an expert meeting.

FIGS. 2A to 2C show a relationship between required time for a meeting and an example of the number of gene mutations and mutation types detected in the gene panel testing. In FIG. 2A, a test request is made first. In FIG. 2B, gene panel testing included in information regarding the test request is conducted. In the example shown in FIG. 2B, as genes to be tested in the gene panel testing, predetermined genes such as "a" gene, "b" gene, "c" gene, "d" gene . . . are included as test items. When mutation analysis of a nucleic acid sequence is performed for each gene included in gene panel testing items, as shown in FIG. 2C, for the gene of each test item, the presence or absence of a mutation, the number of gene mutations, and a mutation type are outputted as a test result. A gene mutation may be contained at one or more sites for each gene. A mutation may be detected in multiple genes in single gene panel testing. Therefore, the number of mutations in the presence or absence of gene mutation is intended to be the number of mutations that can be detected in single gene panel testing. The mutation type may include an actionable mutation, a germline mutation, and another mutation other than the actionable mutation and the germline mutation. One or more kinds of the mutation types may be included in one gene. Thus, the mutation type is intended for all mutation types that may be detected in single gene panel testing. Each number of mutations may be associated with each mutation type.

In general, when gene panel testing is conducted, an expert meeting (hereinafter, sometimes simply referred to as "meeting") is held for almost all patients regarding the result, to determine a treatment strategy. Almost all is intended to exclude, for example, a case where quality of the test or the sample does not bear the test, or a case where the patient dies.

At present, for a patient who has been subjected to the gene panel testing, required time for the expert meeting is set uniformly to some extent, and a meeting time zone is set. However, as shown in FIG. 2C, regarding meeting time for a patient whose mutation has been determined to be "absent" by the gene panel testing, meeting time actually required may be shorter than meeting time of a patient whose mutation has been determined to be "present". The meeting time required for one patient varies also depending on the number of detected gene mutations, and the required time for the meeting tends to be longer as the number of detected gene mutations is larger. Even with the same number of mutations, the required time for the meeting tends to be longer in a case where one patient has a total of three mutations of one actionable mutation, one germline mutation, and another mutation, than a case where one patient has three actionable mutations with evidence of a therapeutic agent. This is because, for example, if a germline mutation is present, it is necessary to consider a response to the patient more carefully than a case of somatic mutation, based on the gene in which the mutation has been detected, age of the patient, a situation of informed consent of the patient, and the like. If another mutation is detected, there is often no potential therapeutic agent with evidence in general, and information indicating clinical significance such as drug information, clinical trial information, and article information may be retrieved from an external server, which will be described later, and a treatment method may be examined. In this case, required time for the meeting tends to be longer than that for an actionable mutation for which a therapeutic agent has been determined to some extent. In a case of retrieving the drug information, the clinical trial information, the article information, and the like from the external server, the required time for the meeting tends to be longer when retrieving information from a plurality of external servers, rather than retrieving information exclusively from a drug information database server (F11 in FIG. 4 described later).

According to the present disclosure, it is possible to set a meeting according to required time for the expert meeting.

As shown in FIG. 1, in the medical facility B1, the doctor in charge H1a accesses a support device A (hereinafter, the integrated data management device A) shown in FIG. 1, to request holding of an expert meeting (V in FIG. 1). When the doctor in charge H1a accesses the integrated data management device A, for example, from an expert meeting terminal provided in the medical facility B1, if a mutation is detected in gene panel testing, dialog UI51 shown in FIG. 3A is displayed on the expert meeting terminal provided in the medical facility B1. The dialog UI51 of FIG. 3A is provided with a candidate schedule display area UI511 that displays a holding date and a candidate schedule having a vacant slot in the schedule. One or a plurality of candidate schedules may be displayed depending on the vacant slot of the schedule. The candidate schedule display area UI511 collectively displays a holding date, a time zone label indicating meeting time according to a test result "mutation present", which is required time of 60 minutes with start time and end time of the meeting of "15:00 to 16:00" and "14:00 to 15:00", for example, and a label "A" indicating the required time of 60 minutes. The label "A" indicating the required time is a label indicating that it is first required time in the present specification.

For example, when no mutation is detected in the gene panel testing, dialog UI52 shown in FIG. 3B is displayed on the expert meeting terminal provided in the medical facility B1. The dialog UI52 of FIG. 3B is provided with a candidate schedule display area UI521 that displays a holding date and a candidate schedule having a vacant slot in the schedule. One or a plurality of candidate schedules may be displayed depending on the vacant slot of the schedule. The candidate schedule display area UI521 collectively displays a holding date, a time zone label indicating meeting time according to a test result "no mutation", which is required time of 10 minutes with start time and end time of the meeting of "16:00 to 16:10", "16:10 to 16:20", and "16:20 to 16:30", for example, and a label "B" indicating the required time of 10 minutes. The label "B" indicating the required time is a label indicating that it is second required time in the present specification.

A meeting time zone indicated by start time and end time of the meeting, required time, a label indicating the required time, and the like may be referred to as "information indicating required time" in the present specification. The first required time is set longer than the second required time.

The dialog UI51 of FIG. 3A and the dialog UI52 of FIG. 3B are outputted from the integrated data management device A shown in FIG. 1, in accordance with a test result. For example, when the dialog UI51 of FIG. 3A is displayed, the doctor in charge H1a sets a desired time zone for holding the expert meeting from the displayed dialog UI51. The desired time zone may be set by the doctor in charge H1a selecting a check box in a selection area UI512 arranged next to the time zone of the candidate schedule and corresponding to the desired time zone in the dialog UI51 of FIG. 3A, and selecting a set icon UI513.

For example, when the dialog UI52 of FIG. 3B is displayed, the doctor in charge H1a sets a desired time zone for holding the expert meeting from the displayed dialog UI52. The desired time zone may be set by the doctor in charge H1a selecting a check box in a selection area UI522 arranged next to the time zone of the candidate schedule and corresponding to the desired time zone in the dialog UI52 of FIG. 3B, and selecting a set icon UI523.

A setting input from the dialog UI51 of FIG. 3A and the dialog UI52 of FIG. 3B may be recorded in a meeting schedule time slot MT, which is a time slot for managing a schedule of meeting time, shown in FIG. 3C. The meeting schedule time slot MT may be stored in a meeting schedule database SDB in the integrated data management device A shown in FIG. 1. The dialog UI51 shown in FIG. 3A, the dialog UI52 shown in FIG. 3B, dialog UI55 shown in FIG. 43D, dialog UI56 shown in FIG. 43E, dialog UI57 shown in FIG. 47D, dialog UI58 shown in FIG. 47E, or dialog UI60 shown in FIG. 53D corresponds to an operation screen in the present specification.

By displaying a graphical user interface such as dialog for reservation of an expert meeting according to a test result on the expert meeting terminal installed in a medical facility, and allowing each doctor in charge of a patient to select a schedule of the meeting from the displayed graphical user interface, the integrated data management device A shown in FIG. 1 allows scheduling of a plurality of expert meetings in the integrated data management device A shown in FIG. 1 for a plurality of requests for holding the expert meeting, in accordance with a holding date and a test result.

In FIG. 1, the doctor in charge H1a explains a treatment strategy indicated in the expert meeting to the patient P1 (VII in FIG. 1). When the patient P1 consents to the treatment strategy, the treatment is started (VIII in FIG. 1).

There may be multiple medical facilities. In this case, individual medical facilities are represented such as by reference numerals B1, B2, and B3.

A nucleic acid sequence mutation can be detected by a method including, with use of a nucleic acid extracted from a sample containing a nucleic acid derived from a tumor cell and a sample containing a nucleic acid derived from a non-tumor cell, (process 1) acquiring first nucleic acid sequence data derived from a tumor cell collected from a patient, and second nucleic acid sequence data derived from a non-tumor cell collected from the same patient; and (process 2) detecting a somatic mutation on the basis of the first nucleic acid sequence data, or the first nucleic acid sequence data and the second nucleic acid sequence data; or (process 2') detecting a germline mutation on the basis of the second nucleic acid sequence data.

A tumor may include a benign epithelial tumor, a benign non-epithelial tumor, a malignant epithelial tumor, and a malignant non-epithelial tumor. An origin of the tumor is not limited. Examples of the origin of the tumor include respiratory system tissue such as a trachea, a bronchus, or a lung; digestive tract tissue such as a nasopharynx, an esophagus, a stomach, a duodenum, a jejunum, an ileum, a cecum, an appendix, an ascending colon, a transverse colon, a sigmoid colon, a rectum, or an anus; a liver; a pancreas; urinary system tissue such as a bladder, a ureter, or a kidney; female reproductive system tissue such as an ovary, a fallopian tube, and a uterus; a mammary gland; male reproductive system tissue such as a prostate gland; skin; endocrine system tissue such as hypothalamus, a pituitary gland, a thyroid gland, a parathyroid gland, and an adrenal gland; central nervous system tissue; bone and soft part tissue; hematopoietic system tissue such as bone marrow and a lymph node; a blood vessel; and the like.

The sample is a test sample containing a nucleic acid derived from a tumor cell, such as tissue, body fluid, excrement collected from a patient, and a test sample prepared from these. The body fluid is, for example, blood, bone marrow fluid, ascitic fluid, pleural effusion, spinal fluid, or the like. The excrement is, for example, stool and urine. A liquid obtained after washing a part of the patient's body, such as an intraperitoneal lavage fluid or a colon lavage fluid, may be used.

An amount of a nucleic acid contained in the sample is not limited as long as a nucleic acid sequence can be detected. When acquiring nucleic acid sequence data derived from a non-tumor cell, a sample containing a nucleic acid derived from a non-tumor cell is used. Concentration of the non-tumor cell contained in the tissue, body fluid, and the like is not limited as long as the nucleic acid sequence present in the non-tumor cell can be detected. When the tumor cell is derived from a solid tumor, for example, it is possible to use peripheral blood, oral mucosa tissue, skin tissue, and the like as the sample containing a non-tumor cell. When the tumor cell is derived from hematopoietic system tissue, it is possible to use oral mucosa tissue, skin tissue, and the like as the sample containing a non-tumor cell.

The sample can be collected from fresh tissue, fresh frozen tissue, paraffin-embedded tissue, or the like. The sample can be collected in accordance with a known method.

The sample containing a nucleic acid derived from a tumor cell and the sample containing a nucleic acid derived from a non-tumor cell are collected from the same patient. The test sample containing a nucleic acid derived from the non-tumor cell and the test sample containing a nucleic acid derived from the tumor cell may be collected at the same timing or may be collected at different timing. The nucleic acid may be DNA or RNA.

A gene whose nucleic acid sequence is to be analyzed is not limited as long as the gene exists on a human genome. The gene is desirably associated with tumor onset, prognosis, and therapeutic efficacy.

The germline mutation may be a disease-related mutation or gene sequence polymorphism. "Polymorphism" of a gene includes single nucleotide polymorphism (SNV), variable nucleotide of tandem repeat (VNTR), short tandem repeat polymorphism (STRP), and the like. A left column of Table 1 shows an example of genes from which a germline mutation may be detected. The genes listed in the left column of Table 1 are respectively related to diseases shown in a right column of the table.

TABLE 1

| Gene | Phenotype |
| --- | --- |
| BRCA1, BRCA2 | Hereditary Breast and Ovarian Cancer |
| TP53 | Li-Fraumeni Syndrome |
| STK11/LKB1 | Peutz-Jeghers Syndrome |
| MLH1, MSH2 | Lynch Syndrome |
| APC | Familial Adenomatous Polyposis |
| VHL | Von Hippel-Lindau Syndrome |
| RET | Multiple Endocrine Neoplasia Type 2 Familial Medullary Thyroid Cancer (FMTC) |
| PTEN | PTEN Hamartoma Tumor Syndrome |
| RB1 | Retinoblastoma |
| TSC1 | Tuberous Sclerosis Complex |
| SMAD4 | Juvenile Polyposis |

The nucleic acid sequence data is not limited as long as the data reflects a nucleic acid sequence. The nucleic acid sequence data may be nucleic acid sequence information itself, and may be data indicating a structure of the nucleic acid sequence or the presence or absence of a mutation in the nucleic acid sequence, or data indicating a structure of protein derived from the nucleic acid sequence. Preferably, the nucleic acid sequence data is the nucleic acid sequence information itself.

Acquisition of the nucleic acid sequence data is not limited as long as the method can acquire mutation information. For the acquisition of the nucleic acid sequence data, the nucleic acid sequence information itself may be acquired with use of a next-generation sequencer described later. In addition, by a PCR-Invader method, a PCR-RFLP method, a PCR-SSCP method, a Southern blotting method, a Northern blotting method, a Western blotting method, a FISH method, a microarray method, an immunostaining method, or the like, data indicating a structure of the nucleic acid sequence or the presence or absence of a mutation in the nucleic acid sequence, or data indicating a structure of protein derived from the nucleic acid sequence may be acquired as the nucleic acid sequence data. These methods for acquiring the nucleic acid sequence data are known. A method for acquiring the first nucleic acid sequence data derived from a tumor cell and a method for acquiring the second nucleic acid sequence data derived from a non-tumor cell are desirably the same method.

Detection of a somatic mutation and a germline mutation can be performed by comparing reference sequence data reported as a general sequence, with the first nucleic acid sequence data and the second nucleic acid sequence data. For example, in comparing the reference sequence data and the first nucleic acid sequence data, a mutation in the first nucleic acid sequence data can be detected by detecting a sequence in the first nucleic acid sequence data that is different from a sequence in the reference sequence data. Similarly, in comparing the reference sequence data and the second nucleic acid sequence data, a mutation in the second nucleic acid sequence data can be detected by detecting a sequence in the second nucleic acid sequence data that is different from a sequence in the reference sequence data.

In FIG. 2B and FIGS. 3A to 3C, all test requests are displayed as a list, but list display may be changed in accordance with, for example, a test date, attribute information, the presence or absence of a setting of an expert meeting, and the like.

II. Test Request Management System for Gene Panel Testing

1. System Configuration

Figure 4:
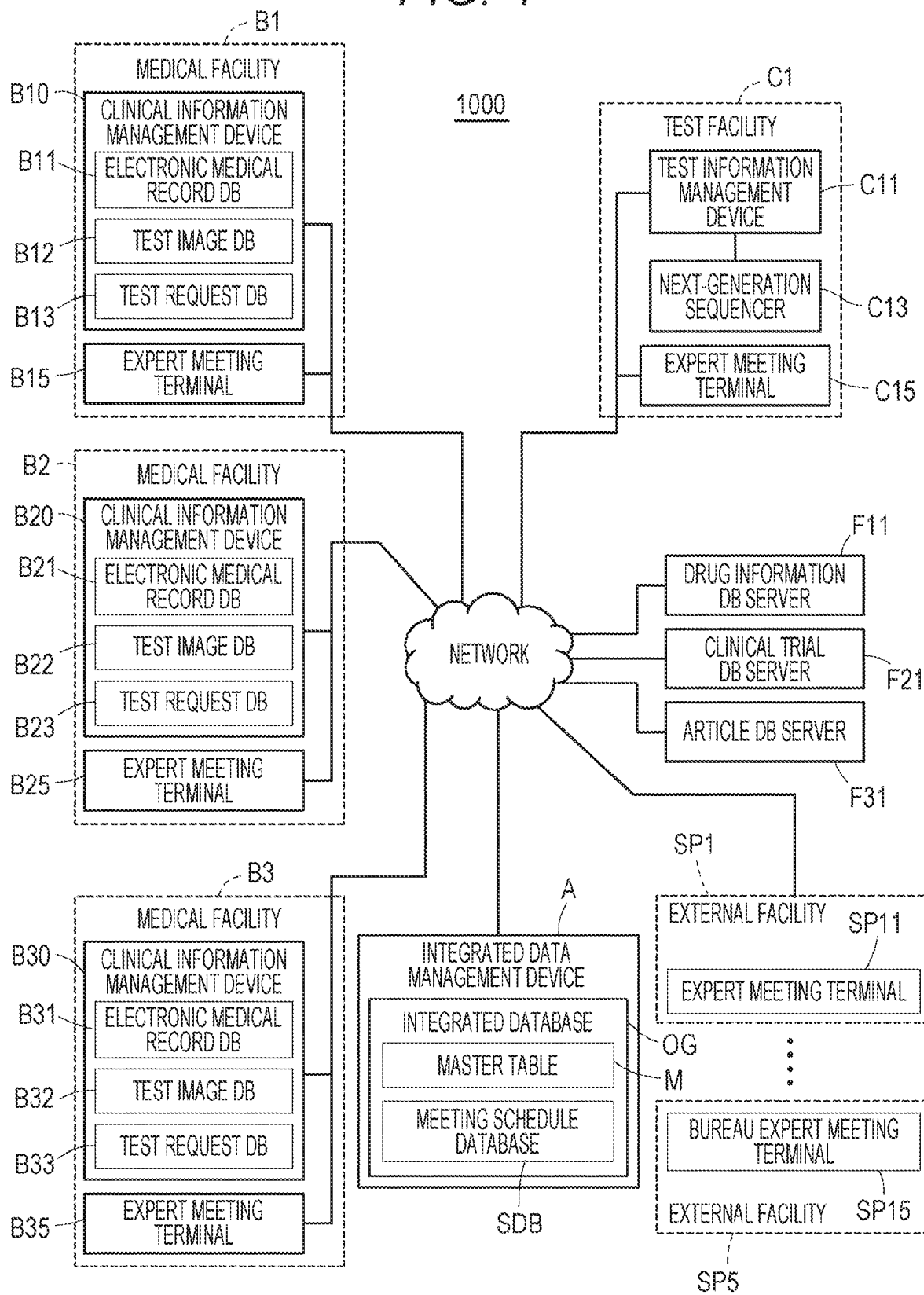
FIG. 4 shows a hardware configuration of a system 1000.

With reference to FIG. 4, a description is given to a configuration of a management system 1000 (hereinafter, simply referred to as a system 1000) for managing, with a computer, a test request for gene panel testing. There may be multiple medical facilities connected to the system 1000. Here, an example is shown in which three medical facilities, a medical facility B1, a medical facility B2, and a medical facility B3 are connected. The system 1000 includes a clinical information management device B10 and an expert meeting terminal B15 that are installed in the medical facility B1, a clinical information management device B20 and an expert meeting terminal B25 that are installed in the medical facility B2, and a clinical information management device B30 and an expert meeting terminal B35 that are installed in the medical facility B3. The clinical information management device B10, the expert meeting terminal B15, the clinical information management device B20, the expert meeting terminal B25, the clinical information management device B30, and the expert meeting terminal B35 are communicably connected to the integrated data management device A via a wired or wireless network. The clinical information management device B10, B20, and B30 are management devices that integrally manage medical record information such as a test request, a test result, prescription information, meal information, and surgery information in a medical facility. The clinical information management devices B10, B20, and B30 are individually and communicably connected to electronic medical record databases (electronic medical record DBs) B11, B21, and B31, test image databases (test image DBs) B12, B22, and B32, and test request databases (test request DBs) B13, B23, and B33 via a wired or wireless network. The expert meeting terminals B15, B25, and B35 of individual medical facilities are used for displaying a graphical user interface UI outputted from the integrated data management device A, requesting to hold an expert meeting, and the like. In the present embodiment, in the clinical information management device B10, the expert meeting terminal B15, the clinical information management device B20, the expert meeting terminal B25, the clinical information management device B30, and the expert meeting terminal B35, a dedicated application for accessing the integrated data management device A is installed.

The system 1000 includes a test information management device C11, a next-generation sequencer C13 connected to the test information management device C11, and an expert meeting terminal C15 of the test facility C1, that are installed in the test facility C1. The test information management device C11 and the expert meeting terminal C15 of the test facility C1 are communicably connected to the integrated data management device A via a wired or wireless network. The test information management device C11 analyzes a nucleic acid sequence by using nucleic acid sequence data acquired from the next-generation sequencer C13. The test information management device C11 also manages receipt of a sample, quality information of a sample and a test, a test progress status, and the like. The expert meeting terminal C15 of the test facility C1 is used by a clinical technologist and a bioinformatician who participate in an expert meeting, to display the graphical user interface UI outputted from the integrated data management device A and to participate in the expert meeting.

The system 1000 includes an expert meeting terminal SP11 installed in an external facility SP1. The expert meeting terminal SP11 of the external facility SP1 is communicably connected to the integrated data management device A via a wired or wireless network. The expert meeting terminal SP11 is used by a genetic counselor and a molecular genetics researcher who participate in an expert meeting, to display the graphical user interface UI outputted from the integrated data management device A and to participate in the expert meeting. There may be a plurality of external facilities. Here, a case of five external facilities is taken as an example, which are represented by external facilities SP1 to SP5. The expert meeting terminals installed in the external facilities are also represented by expert meeting terminals SP11 to SP15 of the external facilities. One of the expert meeting terminals of the external facilities, for example, the expert meeting terminal SP15, may be a terminal used by an expert meeting bureau that controls the expert meeting. The expert meeting terminal SP15 of the external facility is also called a bureau expert meeting terminal SP15. The expert meeting terminal SP15 is used to register a new expert meeting schedule slot in the expert meeting schedule database SDB.

The system 1000 may also include a drug information database (also simply referred to as a drug database or a drug DB) F11, a clinical trial information database (also simply referred to as a clinical trial database or a clinical trial DB) F21, and an article information database (also simply referred to as an article database or an article DB) F31 that are databases of an external institution. The drug information database F11, the clinical trial database F21, and the article database F31 are communicably connected to the integrated data management device A via a wired or wireless network.

Examples of the drug information database F11 include, for example, CanDL (https://candl.osu.edu/), Cancer Genome Interpreter (https://www.cancergenomeinterpreter.org/home), CIViC (https://civicdb.org/home), OncoKB (https://oncokb.org/), and the like. Examples of the clinical trial information database F21 include, for example, clinicaltrials.gov (https://clinicaltrials.gov/), and FAERS (https://www.fda.gov/Drugs/GuidanceComplianceRegulatoryInformation/Surveillance/AdverseDrugEffects/ucm082193.htm). An example of the article information database F31 is PubMed (https://www.ncbi.nlm.nih.gov/pubmed/).

In the system 1000, since the integrated data management device A integrates test request information, attribute information, quality information, an expert meeting setting, and the like regarding gene panel testing, other device and terminal are sometimes called "other computers".

Figure 5:
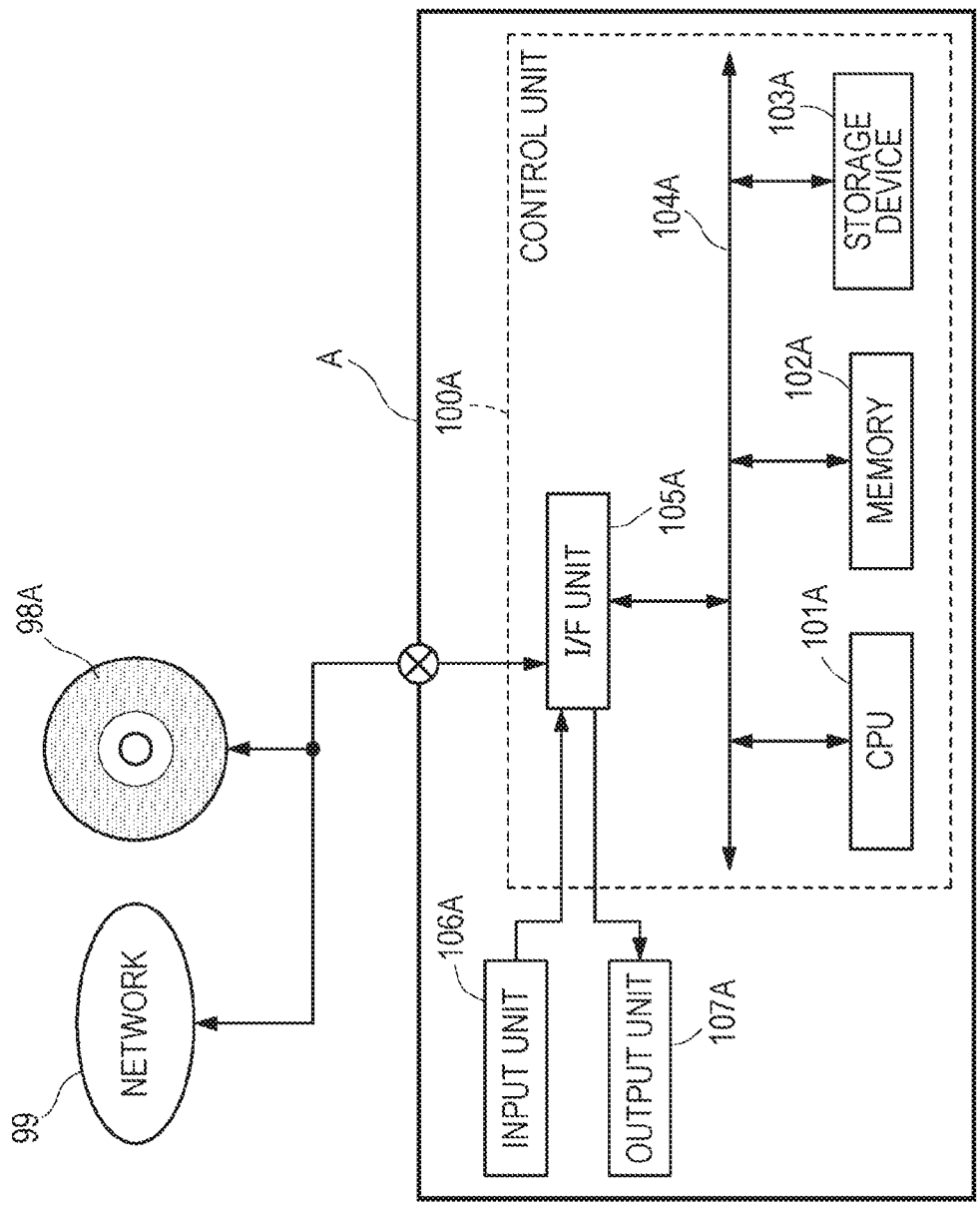
FIG. 5 shows a hardware configuration of an integrated data management device A.

2. Integrated Data Management Device 2-1. Hardware Configuration of Integrated Data Management Device FIG. 5 shows a hardware configuration of the integrated data management device A (also simply referred to as "management device A").

The integrated data management device A may be a general-purpose computer.

The integrated data management device A includes a control unit 100A, an input unit 106A, and an output unit 107A.

The control unit 100A includes a central processing unit (CPU) 101A that performs data processing described later, a memory 102A used as a temporary storage area for data processing, a storage device 103A that records a program and processing data described later, and a bus 104A that transmits data between individual units. The input unit 106A and the output unit 107A are connected to the control unit 100A. Exemplarily, the input unit 106A includes a keyboard, a mouse, a touch sensor, and the like. The output unit 107A includes a display, a printer, a speaker and the like. It is also possible to use a device having both functions of the input unit and the output unit, such as a touch panel in which a touch sensor and a display are integrated. An I/F unit 105A is an interface for the control unit 100A to communicate with an external device or a network. The control unit 100A may connect to a network 99 via the I/F unit 105A, to communicate with the clinical information management device B10, the expert meeting terminal B15 of the medical facility B1, the clinical information management device B20, the expert meeting terminal B25 of the medical facility B2, the clinical information management device B30, the expert meeting terminal B35 of the medical facility B3, the test information management device C11, the expert meeting terminal C15 of the test facility C1, the expert meeting terminal SP11 of an external facility, the expert meeting terminal SP15 of an external facility, the drug information database (drug information DB) F11, the clinical trial database (clinical trial DB) F21, and the article database (article DB) F31 that are databases of an external institution.

The storage device 103A has recorded, in advance, an operating system (OS), an application program to perform a process of each step shown in FIGS. 18 to 21, 30, 31, 37, 39, 41, 42, 44, 45, 46, 48, 49, 51, 52, 54, 56, 58, 60, 61, 63, 64, and 65 below, and mail software, in the storage device 103A in an execution format, for example. The execution format is, for example, a format generated by converting from a programming language by a compiler. The control unit 100A uses each program recorded in the storage device 103A to perform each process shown in FIGS. 18 to 21, 30, 31, 37, 39, 41, 42, 44, 45, 46, 48, 49, 51, 52, 54, 56, 58, 60, 61, 63, 64, and 65. In the storage device 103A, the master table M, and various databases to be used for processing described later such as the expert meeting schedule database SDB linked to the master table M are recorded. The control unit 100A updates information in the master table M on the basis of information transmitted from each clinical information management device, the test information management device, and the expert meeting terminal of each medical facility. The control unit 100A updates information in the expert meeting schedule database SDB on the basis of information transmitted from the expert meeting terminal of each medical facility, the expert meeting terminal of the test facility C1, and the expert meeting terminal of each external facility.

In the following description, unless otherwise noted, processing performed by the control unit 100A means processing performed by the CPU 101A on the basis of an application program stored in the storage device 103A or the memory 102A. The CPU 101A uses the memory 102A as a work area to temporarily store necessary data (intermediate data during processing, and the like) in a volatile manner. The CPU 101A appropriately stores data for long-term storage such as an analysis result in the storage device 103A in a non-volatile manner.

The application program may be downloaded from an external storage medium 98A such as a DVD or a USB memory, to be installed in the storage device 103A of the control unit 100A.

Figure 6:
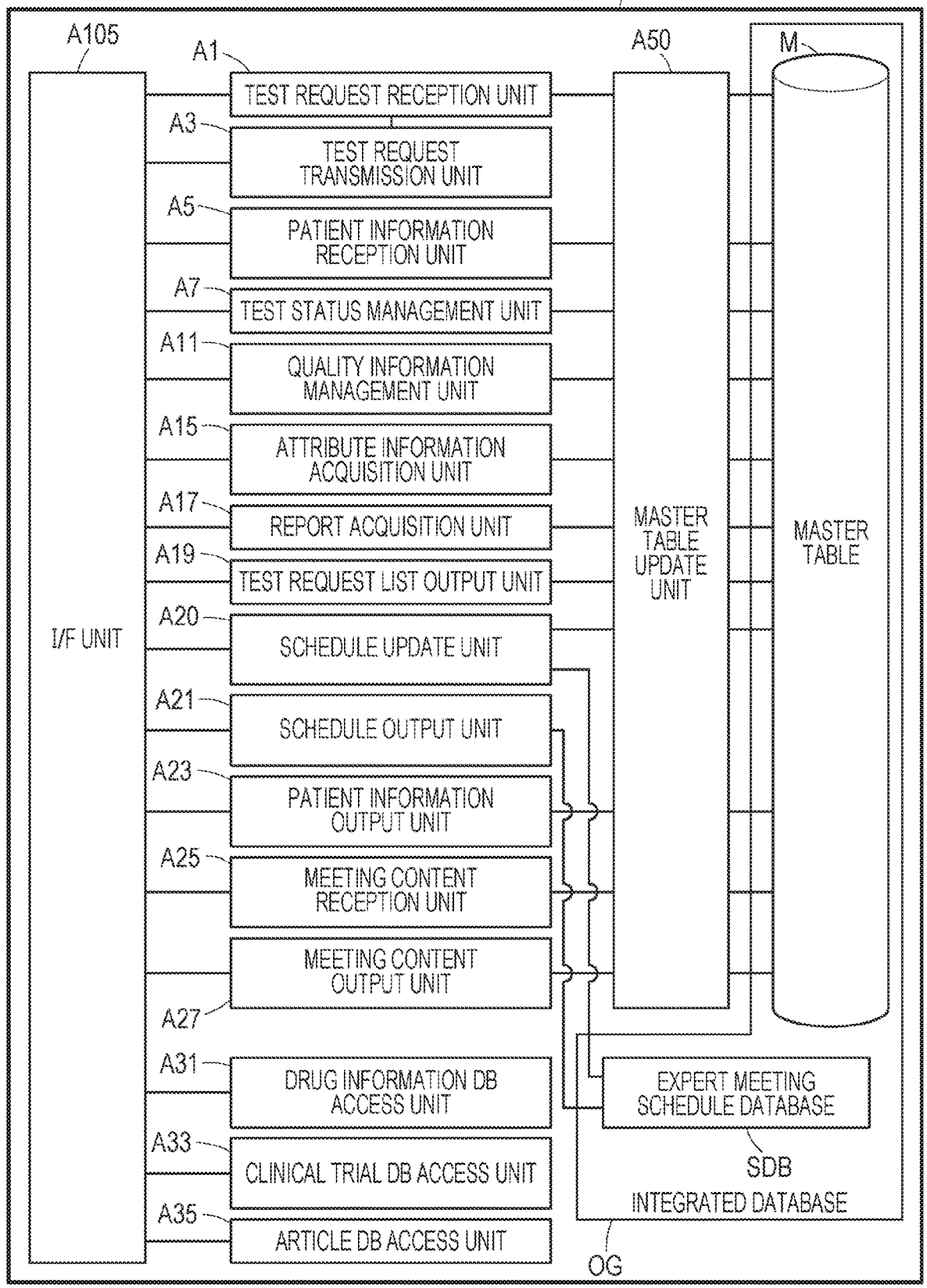
FIG. 6 shows functional blocks of a control unit of the integrated data management device A.

2-2. Functional Configuration of Control Unit of Integrated Data Management Device FIG. 6 shows a functional configuration of the control unit 100A of the integrated data management device A.

The control unit 100A of the integrated data management device A includes a test request reception unit A1, a test request transmission unit A3, a patient information reception unit A5, a test status management unit A7, a quality information management unit A11, an attribute information acquisition unit A15, a report acquisition unit A17, a test request list output unit A19, a schedule update unit A20, a schedule output unit A21, a patient information output unit A23, a meeting content reception unit A25, a meeting content output unit A27, a master table update unit A50, a drug information DB access unit A31, a clinical trial DB access unit A33, an article DB access unit A35, and an integrated database OG. The integrated database OG stores the master table M, various data tables linked to the master table M, the expert meeting schedule database SDB, and the like.

Information in the master table update unit A50 and the master table M is updated by the test request reception unit A1, the patient information reception unit A5, the test status management unit A7, the quality information management unit A11, the attribute information acquisition unit A15, the report acquisition unit A17, the test request list output unit A19, the schedule update unit A20, the patient information output unit A23, the meeting content reception unit A25, and the meeting content output unit A27. The schedule update unit A20 stores a set date and time of an expert meeting received from the expert meeting terminals B15, B25, and B35 of individual medical facilities, in the expert meeting schedule database SDB.

The schedule output unit A21 transmits the set date and time of the expert meeting received from the expert meeting terminals B15, B25, and B35 of individual medical facilities, to the expert meeting terminals B15, B25, B35, C15, SP11, and SP15 of individual medical facilities by mail software or the like. A mail destination is stored in the integrated database OG in association with a user ID of a user who is included in a group of an expert meeting group table GT shown in FIG. 8B, for example.

The drug information DB access unit A31, the clinical trial DB access unit A33, and the article DB access unit A35 are respectively connected to the drug information database F11, the clinical trial database F21, and the article database F31 via the I/F unit 105A.

2-3. Configuration of Master Table

FIG. 7 shows an example of the master table M.

The master table M includes an area for recording "patient ID" that is an identification label of a patient, an area for recording "sample ID" that is an identification label of a sample, an area for recording "test request ID" that is an identification label of a test request, an area for recording "gene panel ID" that is an identification label for gene panel testing, an area for recording "patient name", an area for recording "patient gender", an area for recording "patient date of birth", an area for recording "patient consent" that is informed consent information of a patient, an area for recording "test request date", an area for recording "medical person user ID" that is an identification label of a doctor in charge, an area for recording "group ID" that is a label of a group in charge of an expert meeting, an area showing "patient information" that is information related to patient clinical information, an area for recording "test result" that is information regarding a result of gene panel testing, an area for recording "first attribute information" that is an outline of a test result and is information on the presence or absence of a gene mutation and the number of mutations, an area for recording "second attribute information" that is an outline of a test result and is information regarding a type of a gene mutation and the number of the mutations, an area for recording "quality information" that is information regarding quality of a sample and a test, an area for recording "bureau facility ID" that is identification information of a bureau that leads an expert meeting, an area for recording "holding date and time" of an expert meeting, "time category ID" that is identification information indicating meeting time according to a test result, and "additional time ID" indicating identification information of meeting time that is added in accordance with a predetermined gene mutation type. The master table M may store time corresponding to "time category ID" or "additional time ID", and total time of the time corresponding to "time category ID" and "additional time ID".

The master table M of FIG. 7 shows an example of using, in the gene panel testing, a first sample containing a tumor cell and a second sample containing a normal cell, as samples in one test of one patient. Since two types of samples are used in one test of one patient, in the master table M of FIG. 7, except for "sample ID", "test status", and "quality information", an individual test request display area UI3 in the first and second rows and an individual test request display area UI3 in the third and fourth rows have the same contents.

The field of "bureau facility ID" in the master table M in FIG. 7 is linked with the expert meeting group table GT shown in FIGS. 8A and 8B including "group ID" of an expert meeting and "user ID included in group" in which identification information of a user included in the group is recorded. The "group ID" of the expert meeting group table GT corresponds to the "group ID" of the master table M. Two group IDs G01 and G02 correspond to the "facility ID" F01 in FIG. 8B. Members identified by user IDs: U01, U02, U03, U04, U05 . . . are registered in G01. Members identified by user IDs: U01, U04, U06, U10, U11 . . . are registered in G01.

2-4. Configuration of Test Request List

Information recorded in the master table M and information recorded in a table linked to the master table M can be displayed as a test request list or as a link from a test list, from the expert meeting terminals B15, B25, and B35 of the medical facilities B1, B2, and B3, the expert meeting terminal C15 of the test facility C1, the expert meeting terminal SP11 of the external facility SP1, and the bureau expert meeting terminal SP15, which are shown in FIG. 4. That is, the integrated data management device A can output the information recorded in the master table M to each expert meeting terminal as a test request list. Information recorded in a table linked to the master table M can also be outputted via a link provided in a corresponding item of the test request list.

Each expert meeting terminal can display a test request list and information linked to the test request list via browser software stored in a storage device of each terminal.

FIG. 9 shows an example of the graphical user interface UI including display information outputted from the integrated data management device A.

In FIG. 9, the graphical user interface UI includes a test request list display area UI1 that displays a test request list (also simply referred to as "test request list UI1"), and an area UI10 that shows a display date and time. The test request list UI1 includes an individual test request display area UI3 that displays each test request. The test request list UI1 may include a plurality of individual test request display areas UI3. The test request list UI1 may include areas showing a request date of each test, a test request ID, a test status, patient information, result attribute information, result registration status, and the like, an area showing an output status of a report, a setting status area showing a setting status of an expert meeting, and a holding date and time display area showing a holding date and time of the expert meeting. For example, in the test request ID area, a label indicating a test request ID for identification of each test is given as T01, T02, .... For example, each ID has a link to information regarding each test request registered in the master table M. The patient information area displays a label of "registered" or "unregistered". The "registered" label has a link to patient information associated with each test request registered in the master table M. The result attribute information may display a label indicating whether or not there is a mutation and a label indicating the number of mutations as first attribute information transmitted from the test facility C1, and may display a label indicating a mutation type, such as "actionable mutation", "germline mutation", or "other" and a label indicating the numbers of these as second attribute information. The result registration area may display labels of "registered" and "unregistered" indicating whether or not a result of gene panel testing transmitted from the test facility C1 is registered in the master table M. The setting status area is an area indicating whether or not a meeting is set. When an expert meeting is set, the holding date and time display area displays a schedule. When no expert meeting is set, an "unset" label is displayed in the setting status area. At the expert meeting terminal B15 of the medical facility B1, the doctor in charge H1a can set a schedule of an expert meeting by selecting the unset label from the individual test request display area UI3 of the patient P1. This causes a request for an expert meeting regarding a result of gene panel testing of the patient P1.

Figure 10:
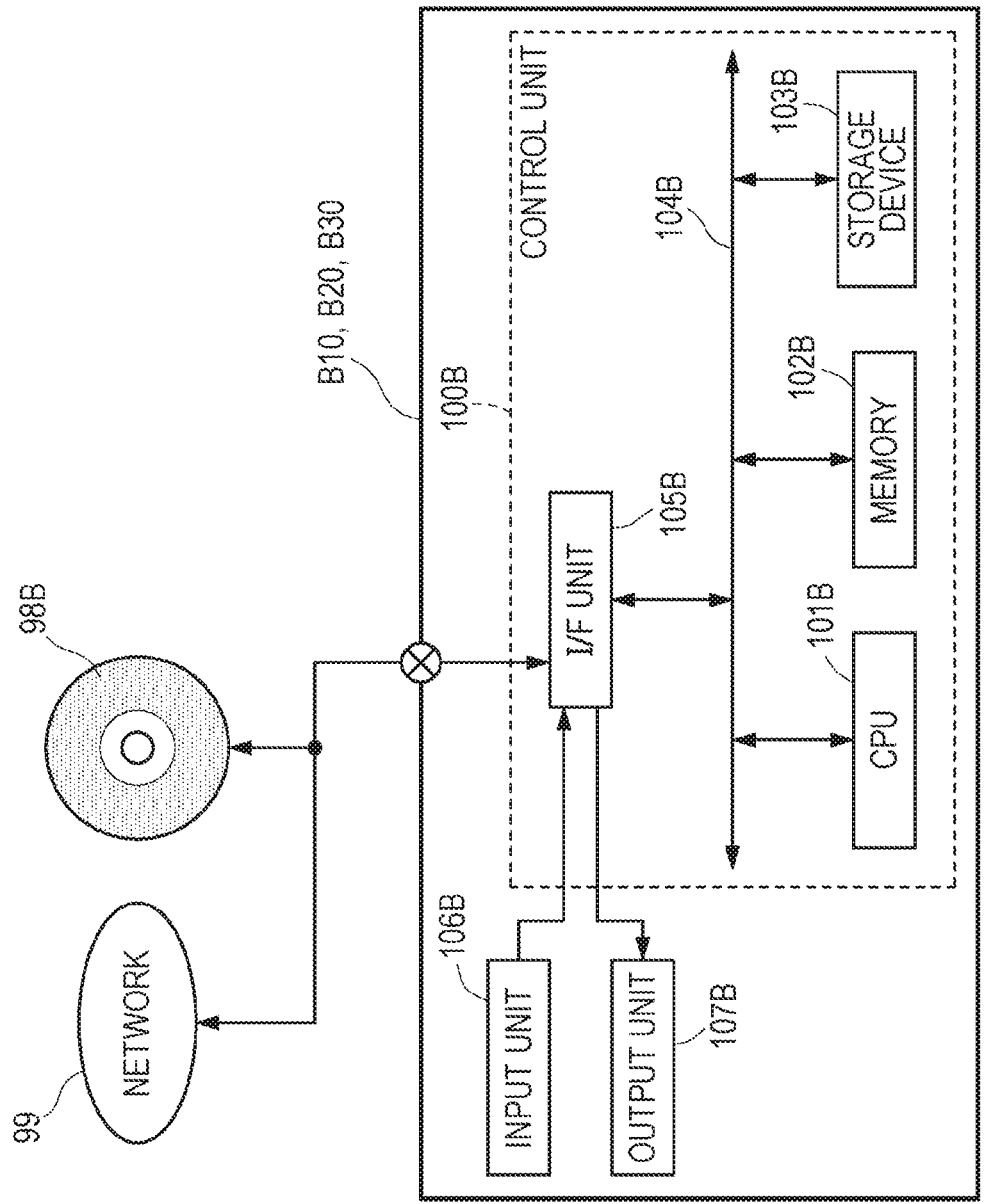
FIG. 10 shows a hardware configuration of clinical information management devices B10, B20, and B30.

3. Clinical Information Management Device 3-1. Hardware Configuration of Clinical Information Management Device FIG. 10 shows a hardware configuration of the clinical information management devices B10, B20, and B30. The clinical information management devices B10, B20, and B30 may be general-purpose computers. The hardware configuration of the clinical information management devices B10, B20, and B30 is basically similar to that of the integrated data management device A. In the clinical information management device B10, B20, and B30, the control unit 100A, the input unit 106A, the output unit 107A, the CPU 101A, the memory 102A, the storage device 103A, the bus 104A, and the I/F unit 105A in the integrated data management device A are to be replaced with a control unit 100B, an input unit 106B, an output unit 107B, a CPU 101B, a memory 102B, a storage device 103B, a bus 104B, and an I/F unit 105B.

The storage device 103B has recorded, in advance, an operating system (OS), a computer program to perform a process of each step shown in FIG. 18 and FIG. 65 below, a computer program to display an electronic medical record stored in the electronic medical record database (DB) B11, a computer program to display a test image stored in the test image database (DB) B12, a computer program to make a test request in a hospital and the like, browser software to make a test request for gene panel testing, and browser software for display of display information and the like outputted from the integrated data management device A. The storage device 103B may store the electronic medical record database (DB) B11, the test image database (DB) B12, and the test request database (DB) B13.

The computer program and the browser software described above may be downloaded from an external storage medium 98B such as a DVD or a USB memory, to be installed in the storage device 103B.

The control unit 100B is connected to the network 99 via the I/F unit 105B to communicate with the integrated data management device A.

Figure 11:
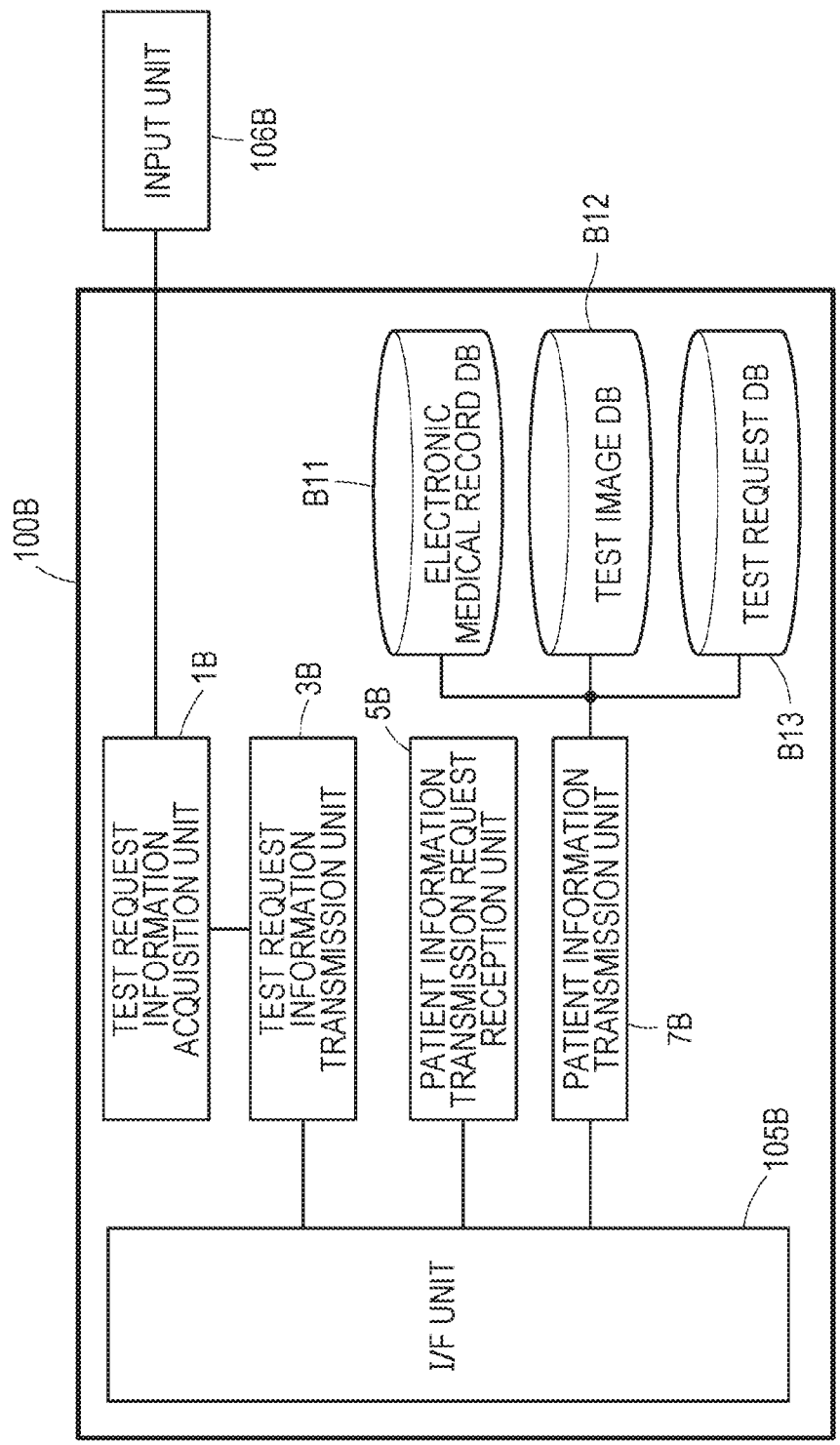
FIG. 11 shows functional blocks of a control unit of the clinical information management device B10, B20, and B30.

3-2. Functional Configuration of Control Unit of Clinical Information Management Device FIG. 11 shows a functional configuration of the control unit 100B of the clinical information management devices B10, B20, and B30.

The control unit 100B of the clinical information management device B10, B20, and B30 includes a test request information acquisition unit 1B, a test request information transmission unit 3B, a patient information transmission request reception unit 5B, a patient information transmission unit 7B, the electronic medical record database (DB) B11, the test image database (DB) B12, and the test request database (DB) B13. The electronic medical record database (DB) B11, the test image database (DB) B12, and the test request database (DB) B13 may be external to and communicatively connected to the clinical information management devices B10, B20, and B30.

Figure 12:
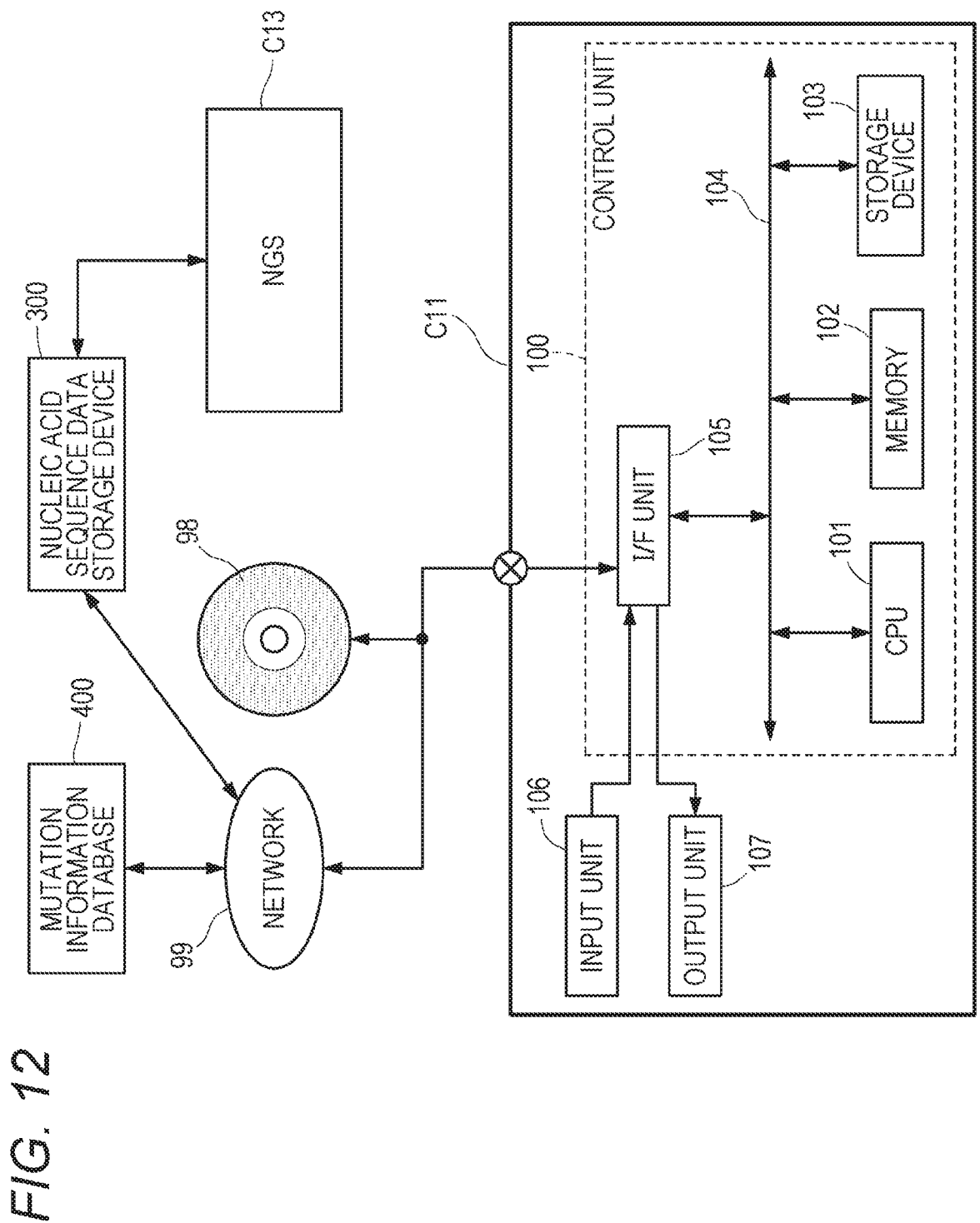
FIG. 12 shows a hardware configuration of a test information management device C11.

4. Test Information Management Device 4-1. Hardware Configuration of Test Information Management Device FIG. 12 shows a hardware configuration of the test information management device C11. The test information management device C11 may be a general-purpose computer.

The test information management device C11 includes a control unit 100, an input unit 106, and an output unit 107.

The control unit 100 includes a CPU 101 that performs data processing described later, a memory 102 used as a temporary storage area for data processing, a storage device 103 that records a program and processing data described later, a bus 104 that transmits data between individual units, and an I/F unit 105 that inputs and outputs data to and from an external device. The input unit 106 and the output unit 107 are connected to the control unit 100. Exemplarily, the input unit 106 includes a keyboard, a mouse, a touch sensor, and the like. The output unit 107 includes a display, a printer, a speaker and the like. It is also possible to use a device having both functions of the input unit and the output unit, such as a touch panel in which a touch sensor and a display are integrated. The I/F unit 105 is an interface for the control unit 100 to communicate with an external device.

The storage device 103 of the control unit 100 has recorded, in advance, an operating system, and an application program to perform a process of each step shown in FIGS. 18, 19, 25, 26, and 37 below, in the storage device 103 in an execution format, for example. The execution format is, for example, a format generated by converting from a programming language by a compiler. The control unit 100 uses the program recorded in the storage device 103 to perform a nucleic acid sequence analysis process and an attribute information acquisition process.

In the following description, unless otherwise noted, processing performed by the control unit 100 means processing performed by the CPU 101 on the basis of a computer program stored in the storage device 103 or the memory 102. The CPU 101 uses the memory 102 as a work area to temporarily store necessary data (intermediate data during processing, and the like) in a volatile manner. The CPU 101 appropriately stores data for long-term storage such as an analysis result in the storage device 103 in a non-volatile manner.

The application program may be downloaded from an external storage medium 98 such as a DVD or a USB memory, to be installed in the storage device 103 of the control unit 100.

The test information management device C11 can be connected to a mutation information database 400 and a nucleic acid sequence data storage device 300 via the network 99.

The mutation information database 400 is an external public sequence information database, a public known mutation information database, or the like. Examples of the public sequence information database include NCBI RefSeq (web page, www.ncbi.nlm.nih.gov/refseq/), NCBI GenBank (web page, www.ncbi.nlm.nih.gov/genbank/), UCSC Genome Browser, and the like. Examples of the public known mutation information database include COSMIC database (web page, www.sanger.ac.uk/genetics/CGP/cosmic/), ClinVar database (web page, www.ncbi.nlm.nih.gov/clinvar/), dbSNP (web page, www.ncbi.nlm.nih.gov/SNP/), and the like. The mutation information database 400 may be a public known mutation information database containing frequency information for each race or animal category regarding a public known mutation. Examples of the public known mutation information database having such information include HapMap Genome Browser release #28, Human Genetic Variation Browser (web page, www.genome.med.kyoto-u.ac.jp/SnpDB/index.html), and 1000 Genomes (web page, www.1000genomes.org/). From these databases, for example, mutation frequency information and the like of Japanese can be obtained.

Examples of a sequencing technology applicable to the next-generation sequencer C13 include a sequencing technology such as ion semiconductor sequencing, pyrosequencing, sequencing-by-synthesis using a reversible dye terminator, sequencing-by-ligation, and sequencing by probe ligation of oligonucleotide, which can acquire multiple read sequences per run. The next-generation sequencer C13 sequences a nucleic acid sequence to acquire read sequence information as nucleic acid sequence information. A read sequence is a nucleic acid sequence obtained by sequencing. The next-generation sequencer C13 outputs read sequence information. The read sequence information may include a sequence name, a nucleic acid sequence, a sequencing quality score, and the like. Read sequence information acquired from a nucleic acid derived from a tumor cell is first nucleic acid sequence data, while read sequence information acquired from a nucleic acid derived from a non-tumor cell is second nucleic acid sequence data.

The nucleic acid sequence data storage device 300 is a computer that stores nucleic acid sequence data acquired by the next-generation sequencer C13.

Figure 13:
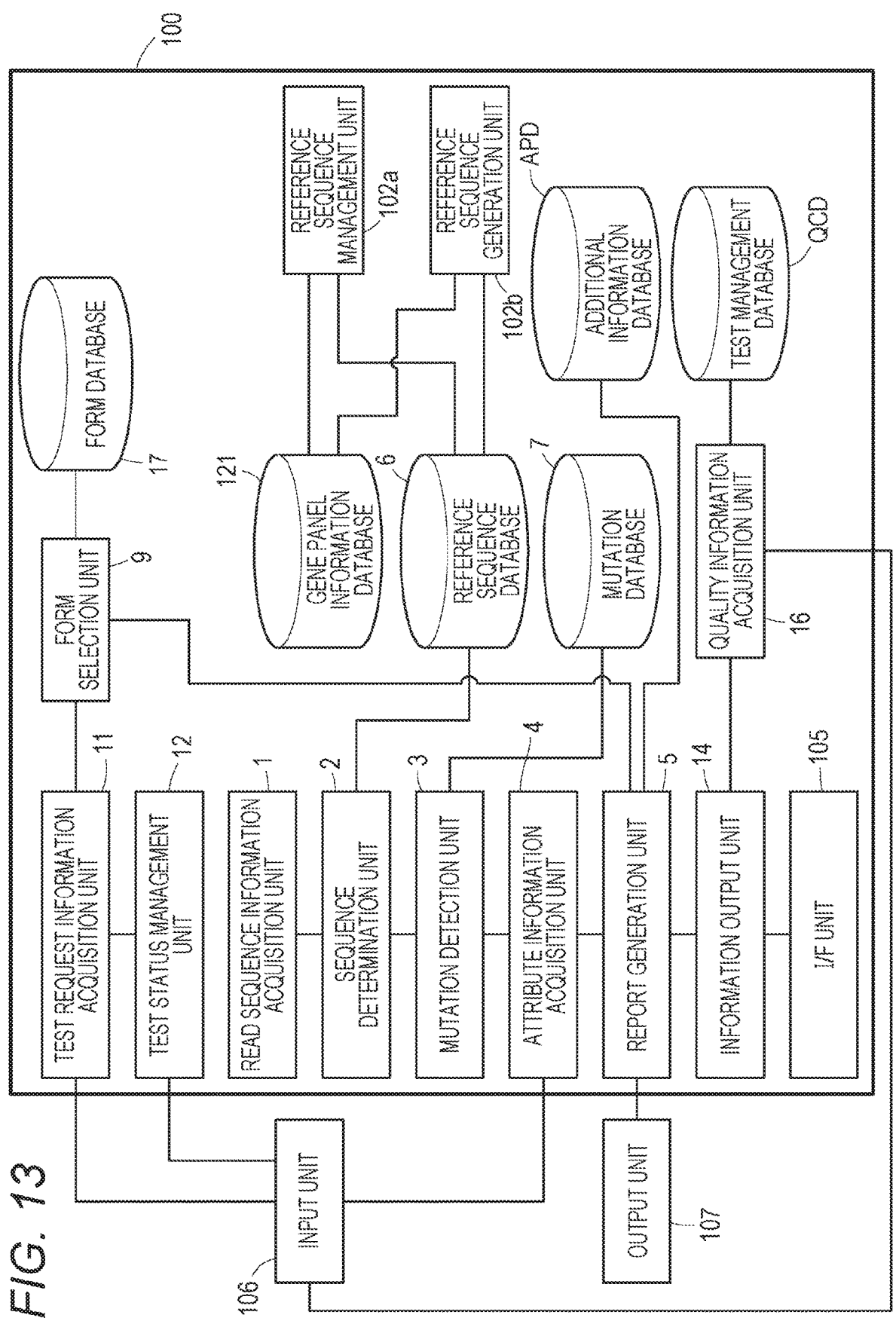
FIG. 13 shows functional blocks of a control unit of the test information management device C11.

4-2. Functional Configuration of Control Unit of Test Information Management Device FIG. 13 shows a functional configuration of the control unit 100 of the test information management device C11.

The control unit 100 of the test information management device C11 includes a test request information acquisition unit 11, a test status management unit 12, a read sequence information acquisition unit 1, a sequence determination unit 2, a mutation detection unit 3, an attribute information acquisition unit 4, a report generation unit 5, an information output unit 14, a form selection unit 9, a form database 17, a quality information acquisition unit 16, a test management database QCD, an additional information database APD, a reference sequence management unit 102a, a reference sequence generation unit 102b, a gene panel information database 121, a reference sequence database 6, and a mutation database 7.

The test request information acquisition unit 11 acquires information regarding a test request, from the integrated data management device A. The test status management unit 12 acquires sample receipt information, pretreatment information, a test progress status, and the like inputted by the clinical technologist T1 and the like, from the input unit 106. The quality information acquisition unit 16 acquires information regarding sample quality inputted by a clinical technologist T1 or the like from the input unit 106. Then, the quality information acquisition unit 16 records the information in a test management table L stored in the test management database QCD. The quality information acquisition unit 16 also acquires information regarding test quality such as sequencing acquired by the read sequence information acquisition unit 1. Then, the quality information acquisition unit 16 records the information in the test management database QCD. The additional information database APD stores additional information attached to a report, that is, information indicating clinical significance. The information indicating clinical significance may include information corresponding to each gene mutation acquired from the drug database F11, the clinical trial database F21, and the article database F31, and URL information for accessing the information.

Figure 14:
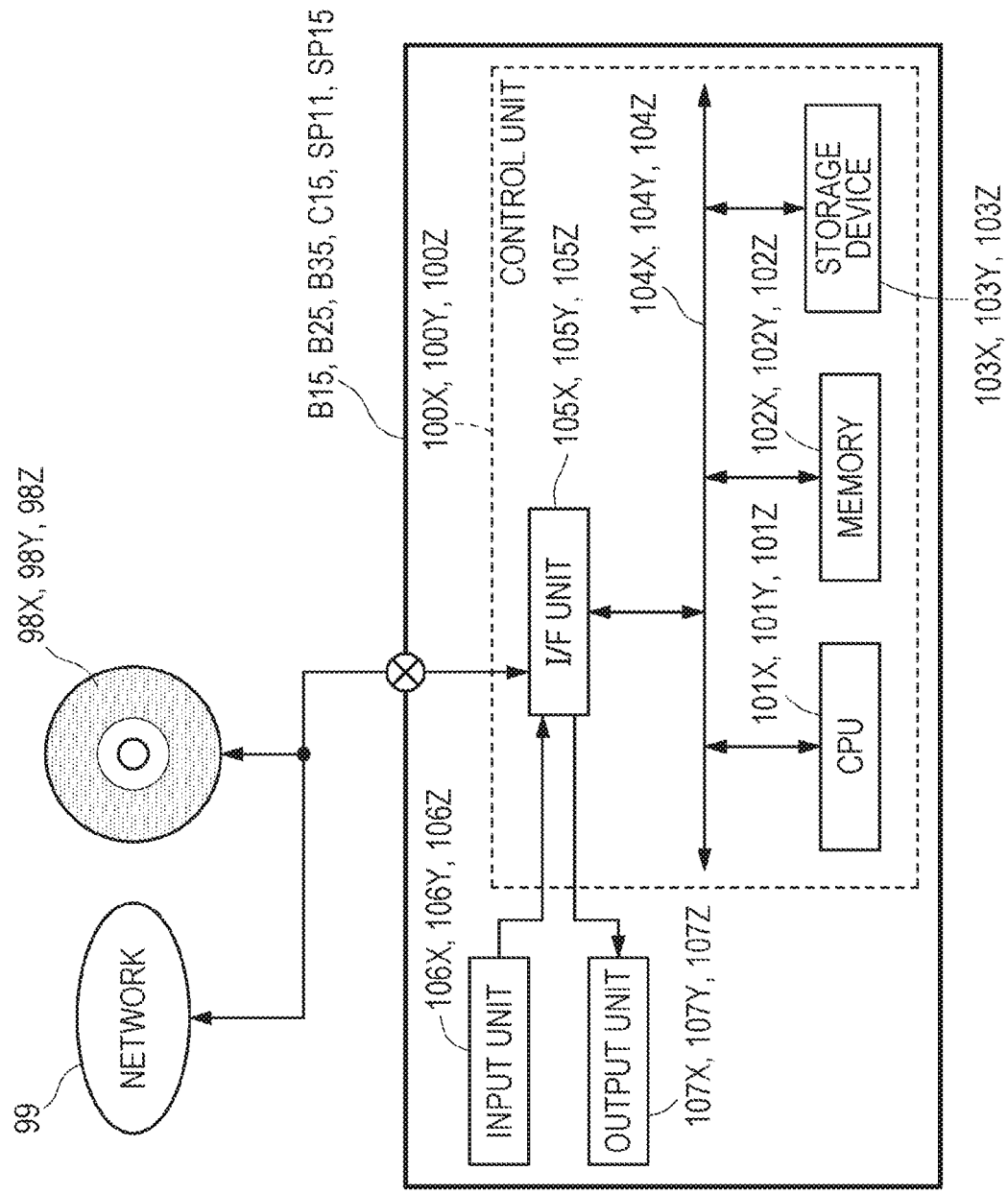
FIG. 14 shows a hardware configuration of each of expert meeting terminals B15, B25, B35, C15, SP11, and SP15.

5. Expert Meeting Terminal in Medical Facility 5-1. Hardware Configuration of Expert Meeting Terminal in Medical Facility FIG. 14 shows a hardware configuration of the expert meeting terminals B15, B25, and B35 installed in the medical facilities B1, B2, and B3.

The expert meeting terminals B15, B25, and B35 installed in the medical facilities B1, B2, and B3 may be general-purpose computers. The hardware configuration of the expert meeting terminals B15, B25, and B35 is basically similar to that of the integrated data management device A. The control unit 100A, the input unit 106A, the output unit 107A, the CPU 101A, the memory 102A, the storage device 103A, the bus 104A, and the I/F unit 105A in the integrated data management device A are to be replaced with a control unit 100X, an input unit 106X, an output unit 107X, a CPU 101X, a memory 102X, a storage device 103X, a bus 104X, and an I/F unit 105X, in the expert meeting terminals B15, B25, and B35.

The storage device 103X stores, in advance, an operating system (OS), a computer program to perform a process of each step shown in FIGS. 20, 21, 38, 22, 24, 28A to 28C, 29, 31, and 33 below, and browser software for display of display information and the like outputted from the integrated data management device A.

The browser software may be downloaded from an external storage medium 98X such as a DVD or a USB memory, to be installed in the storage device 103X.

The control unit 100X is connected to the network 99 via the I/F unit 105X to communicate with the integrated data management device A.

Figure 15:
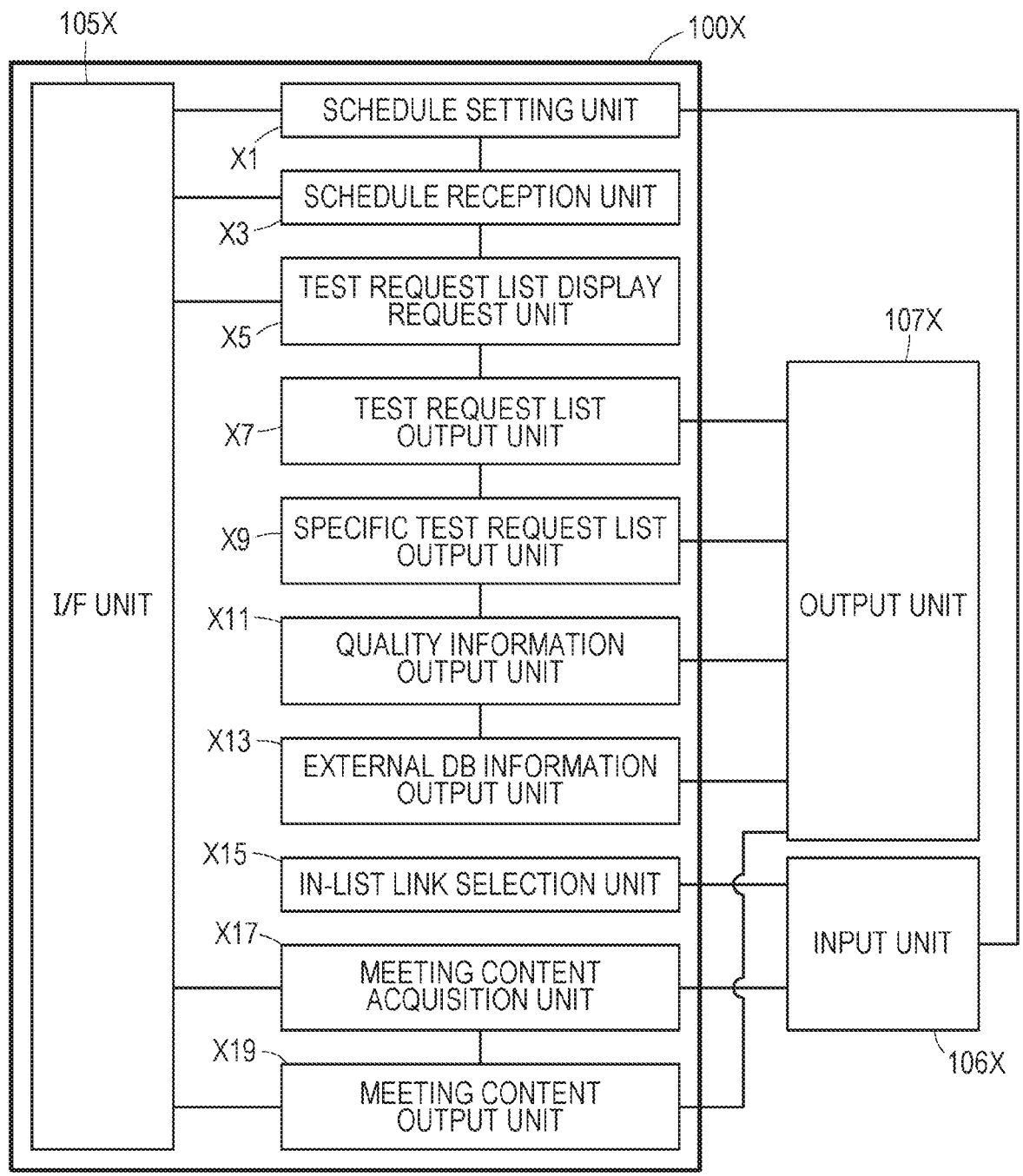
FIG. 15 shows functional blocks of a control unit of the expert meeting terminals B15, B25, and B35 of a medical facility.

5-2. Functional Configuration of Control Unit of Expert Meeting Terminal of Medical Facility FIG. 15 shows a functional configuration of the control unit 100X of the expert meeting terminals B15, B25, and B35 installed in the medical facilities B1, B2, and B3.

The control unit 100X of the expert meeting terminals B15, B25, and B35 installed in the medical facilities B1, B2, and B3 includes a schedule setting unit X1, a schedule reception unit X3, a test request list display request unit X5, a test request list output unit X7, a specific test request list output unit X9, a quality information output unit X11, an external database (DB) information output unit X13, an in-list link selection unit X15, a meeting content acquisition unit X17, and a meeting content output unit X19.

6. Expert Meeting Terminal of Test Facility and Expert Meeting Terminal of External Facility 6-1. Hardware Configuration of Expert Meeting Terminal of Test Facility and Expert Meeting Terminal of External Facility FIG. 14 shows a hardware configuration of the expert meeting terminal C15 of the test facility C1 and the expert meeting terminal SP11 of the external facility SP1.

The expert meeting terminal C15 and the expert meeting terminal SP11 may be general-purpose computers. The hardware configuration of the expert meeting terminal C15 and the expert meeting terminal SP11 is basically similar to that of the integrated data management device A. The control unit 100A, the input unit 106A, the output unit 107A, the CPU 101A, the memory 102A, the storage device 103A, the bus 104A, and the I/F unit 105A in the integrated data management device A are to be replaced with a control unit 100Y, an input unit 106Y, an output unit 107Y, a CPU 101Y, a memory 102Y, a storage device 103Y, a bus 104Y, and an I/F unit 105Y, in the expert meeting terminal C15 of the test facility C1 and the expert meeting terminal SP11 of the external facility SP1.

The storage device 103Y stores, in advance, an operating system (OS), a computer program to perform a process of each step shown in FIGS. 20, 21, 60, and 64 below, and browser software for display of display information and the like outputted from the integrated data management device A.

The browser software may be downloaded from an external storage medium 98Y such as a DVD or a USB memory, to be installed in the storage device 103Y.

The control unit 100Y is connected to the network 99 via the I/F unit 105Y to communicate with the integrated data management device A.

Figure 16:
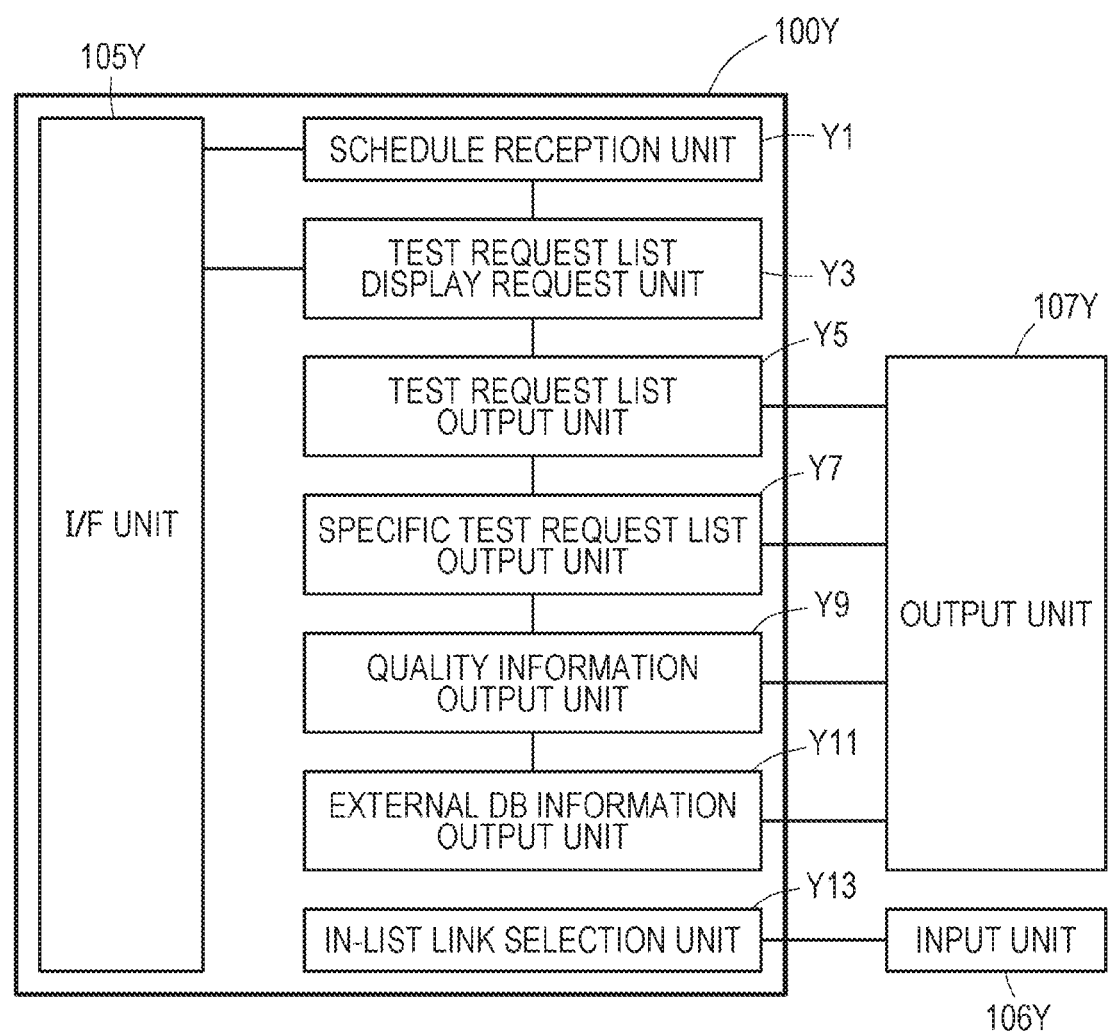
FIG. 16 shows functional blocks of the control unit of the expert meeting terminal C15 of a test facility C1 and an external institution expert meeting terminal SP11.

6-2. Functional Configuration of Control Unit of Expert Meeting Terminal of Test Facility and Expert Meeting Terminal of External Facility FIG. 16 shows a functional configuration of the control unit 100Y of the expert meeting terminal C15 of the test facility C1, and the control unit 100Y of the expert meeting terminal SP11 of the external facility SP1.

The control unit 100Y of the expert meeting terminal C15 and the expert meeting terminal SP11 includes a schedule reception unit Y1, a test request list display request unit Y3, a test request list output unit Y5, a specific test request list output unit Y7, a quality information output unit Y9, an external database (DB) information output unit Y11, and an in-list link selection unit Y13.

7. Bureau Expert Meeting Terminal 7-1. Hardware Configuration of Bureau Expert Meeting Terminal FIG. 14 shows a hardware configuration of the bureau expert meeting terminal SP15.

The bureau expert meeting terminal SP15 may be a general-purpose computer. The hardware configuration of the bureau expert meeting terminal SP15 is basically similar to that of the integrated data management device A. The control unit 100A, the input unit 106A, the output unit 107A, the CPU 101A, the memory 102A, the storage device 103A, the bus 104A, and the I/F unit 105A in the integrated data management device A are to be replaced with a control unit 100Z, an input unit 106Z, an output unit 107Z, a CPU 101Z, a memory 102Z, a storage device 103Z, a bus 104Z, and an I/F unit 105Z, in the bureau expert meeting terminal SP15.

The storage device 103Z stores, in advance, an operating system (OS), a computer program to perform a process of each step described in FIGS. 20, 21, 60, and 64 below, and browser software for display of display information and the like outputted from the integrated data management device A.

The browser software may be downloaded from an external storage medium 98Z such as a DVD or a USB memory, to be installed in the storage device 103Z.

The control unit 100Z is connected to the network 99 via the I/F unit 105Z to communicate with the integrated data management device A.

7-2. Functional Configuration of Control Unit of Bureau Expert Meeting Terminal

Figure 17:
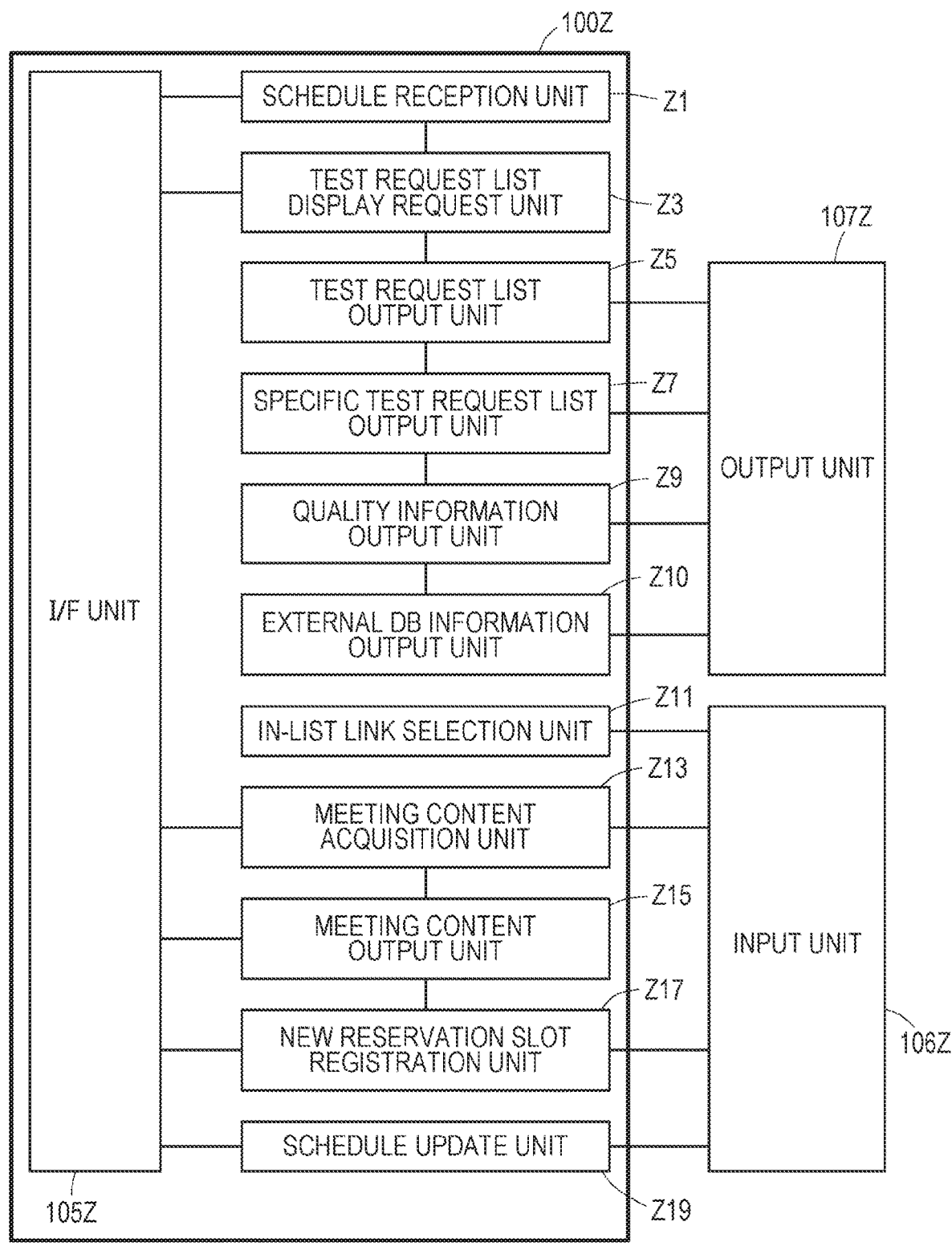
FIG. 17 shows functional blocks of a control unit of a bureau expert meeting terminal SP15.

FIG. 17 shows a functional configuration of the control unit 100Z of the bureau expert meeting terminal SP15.

The control unit 100Z of the bureau expert meeting terminal SP15 includes a schedule reception unit Z1, a test request list display request unit Z3, a test request list output unit Z5, a specific test request list output unit Z7, a quality information output unit Z9, an external database (DB) information output unit Z10, an in-list link selection unit Z11, a meeting content acquisition unit Z13, a meeting content output unit Z15, a new reservation slot registration unit Z17, and a schedule update unit Z19.

8. System Operation

An operation of the system 1000 for test request for gene panel testing will be described with reference to FIGS. 18 to 21.

8-1. Flow of Test Request

In the system 1000, first, the medical facilities B1, B2, and B3 request gene panel testing of a patient having a tumor.

While there may be a plurality of medical facilities who participate in the system 1000, a description is given here to an operation with an example of the medical facility B1 with a case of using the clinical information management device B10 and the expert meeting terminal B15 of the medical facility B1.

The control unit 100B of the clinical information management device B10 installed in the medical facility B1 (hereinafter, also simply referred to as a clinical information management device B10) receives, in step ST1 of FIG. 18, an input of a test request start by the doctor in charge H1a from the input unit 106B. At this time, the control unit 100B functions as the test request information acquisition unit 1B shown in FIG. 11. Processing of the test request information acquisition unit 1B will be described later.

The test request is inputted via a user interface UIa shown in FIG. 22. The user interface UIa may include a medical facility information input area UIa1 for input of information of a request source medical facility, a test request information input area UIa3 for input of test request information, and a request confirmation icon UIa7 for confirmation of a request. The medical facility information input area UIa1 is provided with an area UIa11 that displays a facility name, an area UIa13 for input of facility identification information (ID), an area UIa15 for input of an address of the facility, and an area UIa17 for input of facility contact information.

The test request information input area UIa3 is provided with an area UIa31 for input of a test type for specifying requested gene panel testing, an area UIa32 for input of a name of a doctor in charge of a patient for which the test is requested, an area UIa33 for input of identification information of the doctor in charge as a user in the gene panel testing, an area UIa34 for input of patient identification information (ID), an area UIa35 for input of information regarding patient's informed consent, an area UIa41 for input of a patient's name, an area UIa42 for input of patient's gender, an area UIa43 for input of a patient's date of birth, an area UIa44 for input of a test facility name to which the gene panel testing is requested, an area UIa51 for input of a test request date, an area UIa52 for input of a name of a facility serving as a bureau that leads an expert meeting, an area UIa53 for input of identification information (ID) of the facility serving as the bureau, an area UIa57 for input of an ID of a first sample containing a nucleic acid derived from a tumor cell, and an area UIa58 for input of an ID of a second sample containing a nucleic acid derived from a non-tumor cell.

When the doctor in charge H1a makes input in some or all of individual areas of the user interface UIa from the input unit 106B of the clinical information management device B10, and selects the request confirmation icon UIa7, the clinical information management device B10 transmits a content inputted to the user interface UIa, to the integrated data management device A as information related to the test request. At this time, the control unit 100B of the clinical information management device B10 functions as the test request information transmission unit 3B.

The control unit 100A of the integrated data management device A (hereinafter, simply referred to as an integrated data management device A) receives, in step ST21 of FIG. 18, the test request information transmitted from the clinical information management device B10 via the I/F unit 105A. At this time, the control unit 100A functions as the test request reception unit A1.

Subsequently, in step ST22, the integrated data management device A records the test request information in the master table M, to update the master table M. At this time, the control unit 100A functions as the master table update unit A50.

In the update process of the master table M in step ST22 of FIG. 18, information regarding the test request inputted from the user interface UIa may be reflected in the master table M in the following correspondence relationship, for example.

A column indicating "patient ID" in the master table M, and the patient ID input area UIa34

A column indicating "sample ID" of the master table M, and the first sample ID input area UIa57 and the second sample ID input area UIa58

A "gene panel ID" area of the master table M, and the test type input area UIa31

A "patient name" area of the master table M, and the patient name input area UIa41

A "patient gender" area of the master table M, and the patient gender input area UIa42

A "patient date of birth" area of the master table M, and the patient date-of-birth input area UIa43

A "patient consent" area of the master table M, and the patient informed consent information input area UIa35

A "test request date" area of the master table M, and the test request date input area UIa51, A "medical person user ID" area of the master table M, and a doctor-in-charge user ID input area UIa33

A "medical person name" area of the master table M, and a doctor-in-charge name input area UIa32

A "bureau facility" area of the master table M, and the bureau facility name input area UIa52.

Information regarding a test request other than the above, an input area of which is not shown in FIG. 7, is also stored in a predetermined area of the master table M.

Information inputted in the "test request ID" area of the master table M is, for example, given to the master table M in advance. When the integrated data management device A acquires information regarding a new test request, fields of the same row other than the "test request ID" area are automatically blank. By inputting acquired information regarding the new test request in fields of a row whose test request ID is the smallest, the information regarding the new test request can be associated with the test request ID in the master table M.

Figure 18:
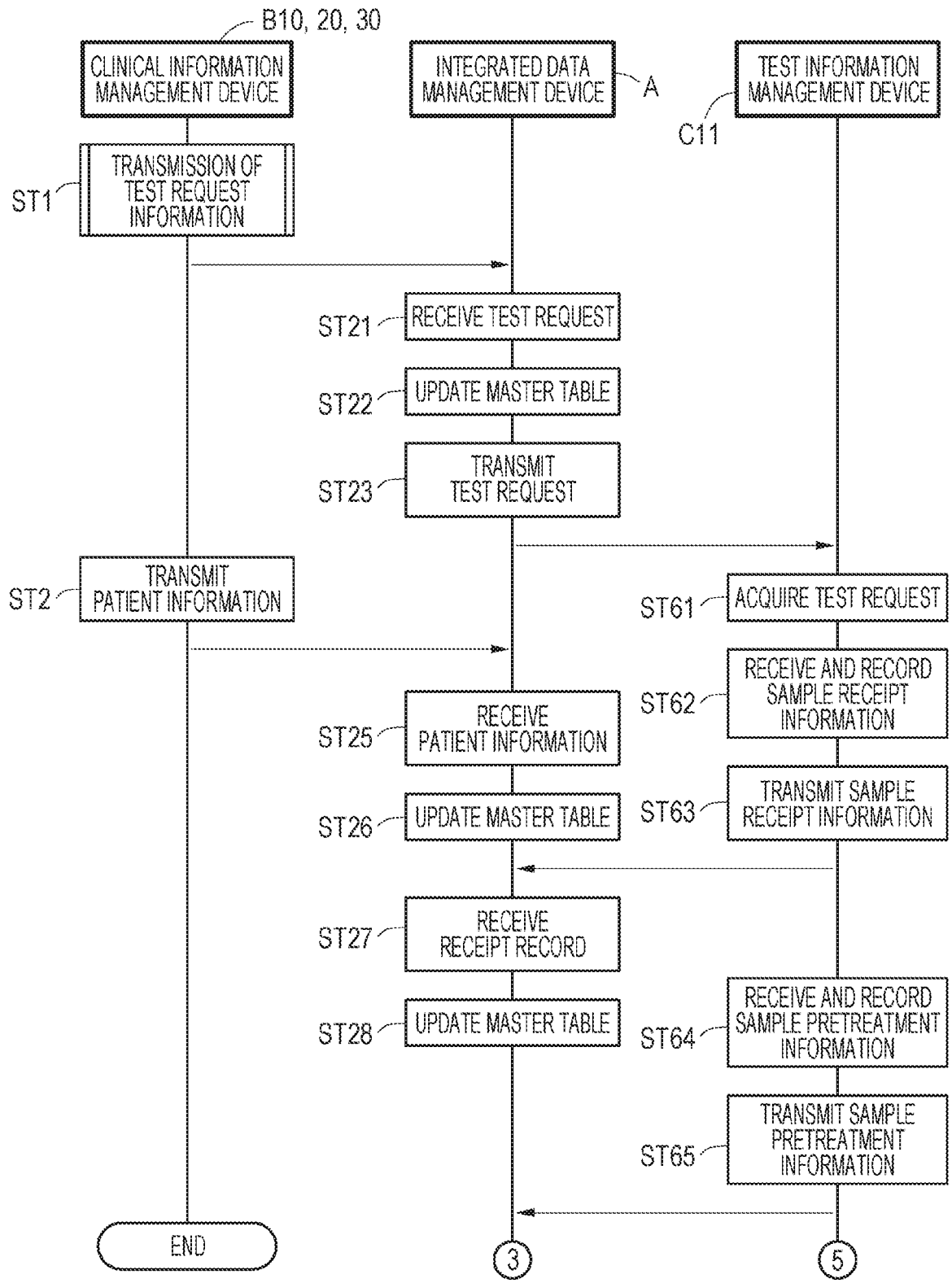
FIG. 18 is a flowchart showing a part of an operation of the system 1000.

Next, in step ST23 of FIG. 18, the integrated data management device A transmits test request information acquired in step ST22 to the test information management device C11 via the I/F unit 105A. At this time, in addition to the acquired test request information, the test request ID given in step ST22 may be included in the test request information and transmitted to the test information management device C11. In step ST23, the control unit 100A of the integrated data management device A functions as the test request transmission unit A3. The transmission in step ST23 of FIG. 18 may be triggered by the integrated data management device A updating the master table M. An operator who operates the integrated data management device A may input a transmission request via the input unit 106A.

The control unit 100 of the test information management device C11 (hereinafter, also simply referred to as a test information management device C11) acquires, in step ST61, the test request information transmitted from the integrated data management device A via the I/F unit 105. The test information management device C11 stores the acquired test request information in the storage device 103. At this time, the control unit 100 of the test information management device C11 functions as the test request information acquisition unit 11. FIG. 23 shows an example of the test management table L to store data that is acquired by the test information management device C11 and is stored in the test information management device C11.

The information regarding the test request acquired in step ST61 of FIG. 18 may be reflected in the test management table L in the following correspondence relationship, for example.

A column indicating "patient ID" in the test management table L, and the patient ID input area UIa34

A column indicating "sample ID" of the test management table L, and the first sample ID input area UIa57 and the second sample ID input area UIa58

A "gene panel ID" area of the test management table L, and the test type input area UIa31

A "patient name" area of the test management table L, and the patient name input area UIa41

A "patient gender" area of the test management table L, and the patient gender input area UIa42

A "patient date of birth" area of the test management table L, and the patient date-of-birth input area UIa43

A "patient consent" area of the test management table L, and the patient informed consent information input area UIa35

A "test request date" area of the test management table L, and the test request date input area UIa51, A "medical person user ID" of the test management table L, and the doctor-in-charge user ID input area UIa33

The test management table L may have the same configuration as that of the master table M, but an expert meeting bureau, a holding date and time, a group ID, patient information, and the like may not be present at a test stage.

Next, in step ST2 of FIG. 18, the clinical information management device B10 calls patient information of the patient for which the test request is made, from the electronic medical record database B11 or the test image database B12. Then, the clinical information management device B10 transmits the patient information to the integrated data management device A. At this time, the control unit 100B of the clinical information management device B10 functions as the patient information transmission unit 7B. The information transmitted in step ST2 of FIG. 18 may be included in test request information and transmitted when the test request information is transmitted in step ST1. The doctor in charge H1*a* may also input a transmission request from the input unit 106B to the control unit 100B. For example, the patient information may be transmitted by the doctor in charge H1*a* in step ST83 of FIG. 20 described later. At this time, the control unit 100B of the clinical information management device B10 functions as the patient information transmission request reception unit 5B (FIG. 11).

The integrated data management device A receives the patient information via the I/F unit 105A in step ST25 of FIG. 18. At this time, the control unit 100 of the integrated data management device A functions as the patient information reception unit A5. In step ST26 of FIG. 18, the integrated data management device A records the patient information in the master table M, to update the master table M. The patient information is stored in the "patient information" area of the master table M. At this time, the control unit 100 of the integrated data management device A functions as the master table update unit A50 (FIG. 6).

The processes of step ST2, step ST25, and step ST26 of FIG. 18 may be performed before step ST1 of FIG. 18. The processes above are simply required to be performed before an end of setting of the expert meeting (ST83 in FIG. 20) described later.

8-2. Flow of Gene Panel Testing

Figure 25:
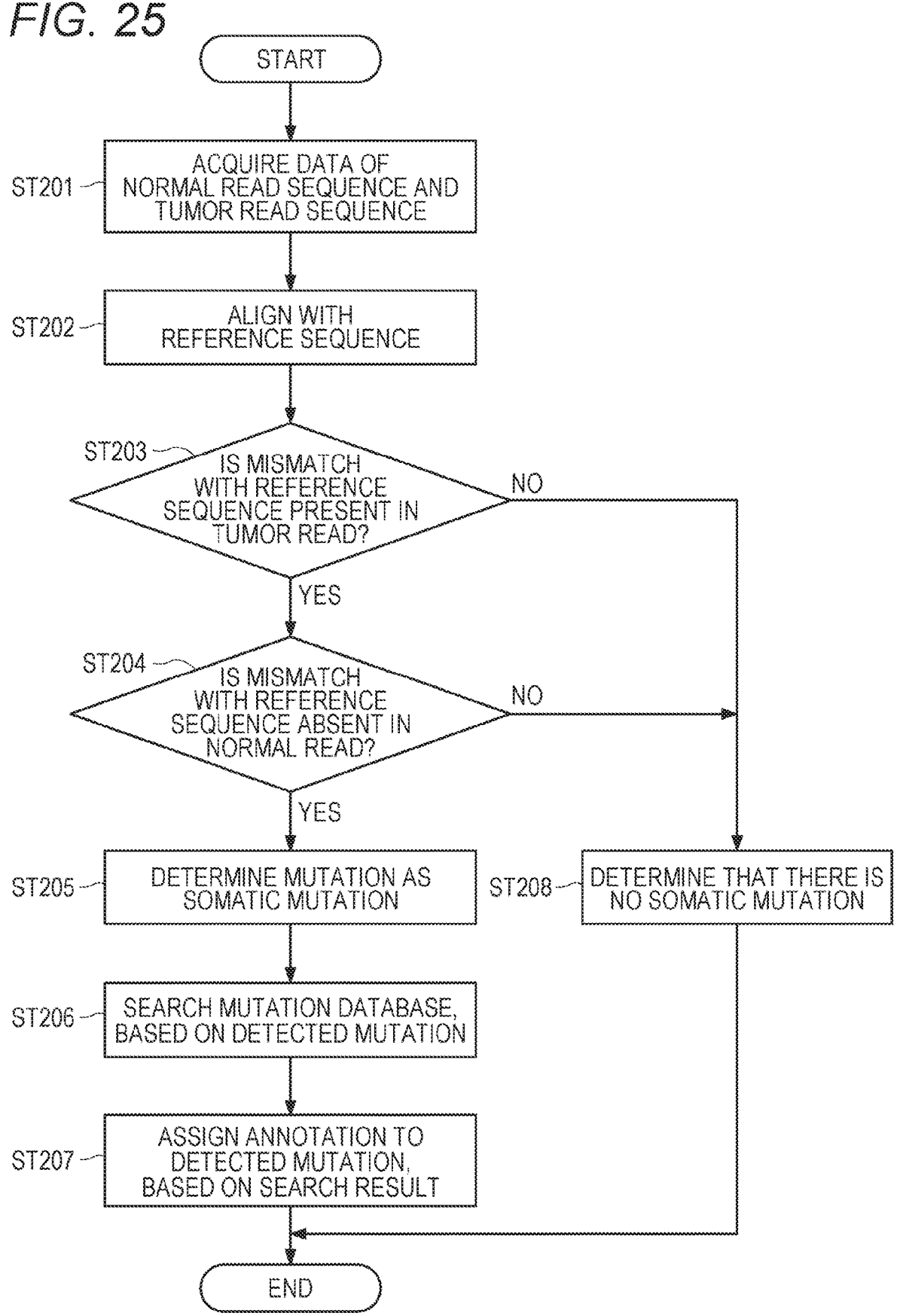
FIG. 25 shows a flowchart of mutation analysis.

Gene panel testing is started when the test information management device C11 receives test request information. When a sample of a patient collected at the medical facility B1 is carried into the test facility C1, for example, the clinical technologist T1 of the test facility C1 inputs a label of sample receipt in a test status area of the test management table L stored in the storage device 103, via the input unit 106 of the test information management device C11. A list of labels indicating a test status is shown in FIG. 25. The label of the test status may be appropriately inputted by the clinical technologist T1 along with progress of the test. This input is received by the test information management device C11. At this time, the control unit 100 of the test information management device C11 functions as the test status management unit 12 (FIG. 13).

In step ST63 of FIG. 18, the test information management device C11 transmits, as sample receipt information, the fact that a test status of the test management table L is updated to "sample receipt" in step ST62, to the integrated data management device A. At this time, the control unit 100 of the test information management device C11 functions as the test status management unit A7 (FIG. 6).

The integrated data management device A receives, in step ST27, the sample receipt information transmitted by the test information management device C11 in step ST63. At this time, the control unit 100A of the integrated data management device A functions as the test status management unit A7. The integrated data management device A updates the "test status" area of the master table M in step ST28, on the basis of the content received in step ST27. At this time, the control unit 100A of the integrated data management device A functions as the master table update unit A50 (FIG. 6). The information in the test management table L and the information in the master table M can be linked by, for example, the test request ID, the sample ID, the patient ID, and the test request date. The information transmission in step ST63 of FIG. 18 may be automatically performed when the test management table L is updated. Further, the information transmission may be performed by the clinical technologist T1 or the like inputting a transmission request from the input unit 106.

The sample carried into the test facility C1 is subjected to pretreatment such as nucleic acid extraction treatment and a nucleic acid quality test. When the pretreatment of the sample is completed, in step ST64 of FIG. 18, via the input unit 106 of the test information management device C11, the clinical technologist T1 inputs a label indicating pretreatment process completed shown in FIG. 25, in the test status area of the test management table L stored in the storage device 103. This input is received by the test information management device C11. At this time, the control unit 100 of the test information management device C11 functions as the test status management unit 12 (FIG. 13).

The test information management device C11 updates the test status of the test management table L to "pretreatment process completed" in step ST64. Then, the test information management device C11 transmits the information on the test status to the integrated data management device A in step ST65 of FIG. 18. The control unit 100 of the test information management device C11 functions as the test status management unit 12 (FIG. 13).

Figure 19:
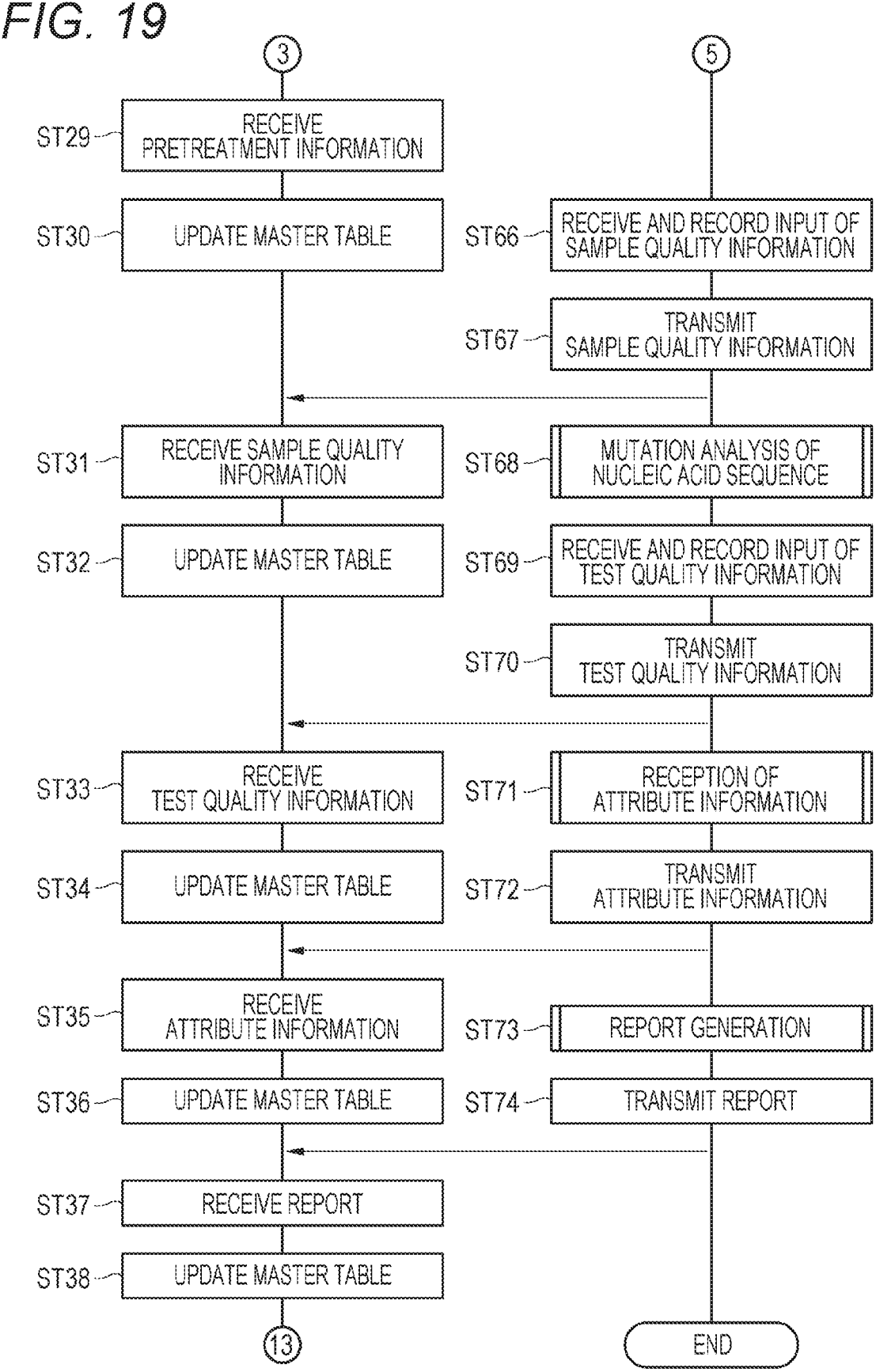
FIG. 19 is a flowchart showing a part of an operation of the system 1000.

The integrated data management device A updates the "test status" area of the master table M on the basis of the test status information transmitted by the test information management device C11, in step ST29 of FIG. 19. At this time, the control unit 100A of the integrated data management device A functions as the master table update unit A50 (FIG. 6). The information in the test management table L and the information in the master table M can be linked by, for example, the test request ID, the sample ID, the patient ID, and the test request date. The information transmission in step ST65 may be automatically performed when the test management table L is updated. Further, the information transmission may be performed by the clinical technologist T1 or the like inputting a transmission request from the input unit 106.

The clinical technologist T1 then registers information regarding sample quality in "quality information" of the test management table L stored in the storage device 103, via the input unit 106 of the test information management device C11. The field of the "quality information" is linked to a sample quality information input table Q for input of sample quality information. FIG. 24 shows an example of the sample quality information input table Q. The sample quality information input table Q shown in FIG. 24 is provided with at least an extraction date, a test request ID, an input field of "extracted nucleic acid amount" for input of an absolute amount of a nucleic acid extracted for a first sample, an input field of "electrophoresis result" evaluated by electrophoresis as to whether the extracted nucleic acid is not excessively decomposed, an input field for input of "extracted nucleic acid amount" for a second sample, and an input field for input of "electrophoresis result". The extraction date is a date on which a nucleic acid has been extracted. The "sample request ID" of the sample quality information input table Q corresponds to the "test request ID" of the test management table L and the master table M. Samples with "test request ID" T01 and T02 shown in the sample quality information input table Q can be said to have sufficient quality as a nucleic acid sample to be used for sequencing, since an amount of the extracted nucleic acid is sufficient for both the first sample and the second sample, and the electrophoresis result is also favorable. However, for a nucleic acid sample derived from the first sample with the "test request ID" of T03, a nucleic acid amount is a detection limit or less, and a sufficient nucleic acid sample has not been obtained. In such a case, even if no mutation is detected by sequencing, it is not possible to adopt the test result. Therefore, it is necessary to collect the sample again.

In step ST66 of FIG. 19, the test information management device C11 receives information inputted by the clinical technologist T1 to a sample quality information table via the input unit 106. Then, the test information management device C11 records the information in the storage device 103. At this time, the control unit 100 of the test information management device C11 functions as the quality information acquisition unit 16 (FIG. 13).

Next, in step ST67 of FIG. 19, the test information management device C11 transmits, as sample quality information, the content recorded in the sample quality information table in step ST66, to the integrated data management device A. The control unit 100 of the test information management device C11 functions as the information output unit 14 (FIG. 13).

In step ST31, the integrated data management device A receives sample quality information transmitted by the test information management device C11 in step ST67. At this time, the control unit 100A of the integrated data management device A functions as the quality information management unit A11 (FIG. 6). The integrated data management device A updates the "quality information" area of the master table M in step ST32. At this time, the control unit 100A of the integrated data management device A functions as the master table update unit A50 (FIG. 6). The information in the test management table L and the information in the master table M can be linked with, for example, the test request ID and the like. The information transmission in step ST67 may be automatically performed when the test management table L is updated. Further, the information transmission may be performed by the clinical technologist T1 or the like inputting a transmission request from the input unit 106.

Next, in step ST68 of FIG. 19, the test information management device C11 performs sequencing of a nucleic acid sample extracted from the first sample and a nucleic acid sample extracted from the second sample by the next-generation sequencer C13, to perform mutation analysis of the nucleic acid sequence. An outline of a nucleic acid sequence mutation analysis process will be described later.

In step ST68 of FIG. 19, when the sequencing is performed, quality of sequencing analysis is acquired for each test batch (one sequencing is one batch, and samples of a plurality of patients are subjected to sequencing for each batch) by the next-generation sequencer C13, and a quality control report (also called QC report) of the test is recorded in the test management database QCD of the storage device 103.

In step ST69 of FIG. 19, the test information management device C11 registers test quality information by storing or associating the QC report corresponding to each sample subjected to the sequencing, in a field of the quality information corresponding to each sample of the test management table L.

In steps ST68 and ST69 of FIG. 19, the control unit 100 of the test information management device C11 functions as the quality information acquisition unit 16 (FIG. 13).

When quality information of a new test is registered in the "quality information" field in step ST69, the test information management device C11 transmits, in step ST70 of FIG. 19, the content recorded in the test management table L to the integrated data management device A as test quality information. At this time, the control unit 100 of the test information management device C11 functions as the information output unit 14 (FIG. 13).

In step ST33, the integrated data management device A receives the test quality information transmitted in step ST70 of FIG. 19. In step ST34, the integrated data management device A records the test quality information in the "quality information" area of the master table M, to update the master table M. At this time, the control unit 100A of the integrated data management device A functions as the master table update unit A50 (FIG. 6). The information in the test management table L and the information in the master table M can be linked with, for example, the test request ID and the like. The information transmission in step ST70 of FIG. 19 may be automatically performed when the test management table L is updated. Further, the information transmission may be performed by the clinical technologist T1 or the like inputting a transmission request from the input unit 106.

Next, in step ST71 of FIG. 19, the test information management device C11 acquires attribute information indicating an outline of a test result of the gene panel testing, on the basis of a mutation analysis result detected in step ST68. Details of the attribute information acquisition process will be described later. The test information management device C11 records the acquired attribute information in the attribute information field of the test management table L. In step ST71, the control unit 100 of the test information management device C11 functions as the attribute information acquisition unit 4 (FIG. 13).

When new attribute information is registered in the "attribute information" field in step ST71, the test information management device C11 transmits, in step ST72 of FIG. 19, the content recorded in the test management table L to the integrated data management device A, as attribute information. At this time, the control unit 100 of the test information management device C11 functions as the information output unit 14 (FIG. 13). The attribute information is one embodiment of "test result" in the present specification.

In step ST35, the integrated data management device A receives the attribute information transmitted in step ST72 of FIG. 19. In step ST36, the integrated data management device A records the attribute information in the "attribute information" area of the master table M, to update the master table M. The information in the test management table L and the information in the master table M can be linked with, for example, the test request ID and the like. The information transmission in step ST72 of FIG. 19 may be automatically performed when the test management table L is updated. Further, the information transmission may be performed by the clinical technologist T1 or the like inputting a transmission request from the input unit 106.

Next, in step ST73 of FIG. 19, the test information management device C11 performs a report generation process of a test result of the gene panel testing on the basis of the mutation analysis result detected in step ST68. At this time, the control unit 100 of the test information management device C11 functions as the report generation unit 5 (FIG. 13). Details of the report will be described later. At this time, the control unit 100 of the test information management device C11 functions as the information output unit 14 (FIG. 13).

The test information management device C11 registers the test result of the test by storing the report generated in step ST73 of FIG. 19 in a test result field corresponding to each test request ID in the test management table L, or providing a link. The test result described in the report is one embodiment of the "test result" in the present specification.

When a new test result is registered in the "test result" field in step ST73, the test information management device C11 transmits, in step ST74 of FIG. 19, the content recorded in the test management table L to the integrated data management device A, as test result information.

In step ST37, the integrated data management device A receives the test result information transmitted in step ST74 of FIG. 19. In step ST38, the integrated data management device A records the test quality information in the "test result" area of the master table M, to update the master table M. The information in the test management table L and the information in the master table M can be linked with, for example, the test request ID and the like. The information transmission in step ST74 of FIG. 19 may be automatically performed when the test management table L is updated. Further, the information transmission may be performed by the clinical technologist T1 or the like inputting a transmission request from the input unit 106.

The gene panel testing report generated by the test information management device C11 in step ST73 of FIG. 19 is outputted from the output unit 107 such as a printer, to be sent to the medical facility B1 as a paper medium.

In FIG. 19, through the processing from steps ST21 to ST28 shown in FIG. 18 and steps ST29 to ST38 shown in FIG. 19, the integrated data management device A acquires information regarding the test request from the clinical information management device B10, or the clinical information management device B10, B20, or B30 of a first group, which is another computer different from the integrated data management device A. Further, the integrated data management device A acquires attribute information, a test result, sample and test quality management information from the test information management device C11, which is different from the integrated data management device A and the clinical information management devices B10, B20, and B30. The integrated data management device A integrates these pieces of information, to record individual information in the master table M shown in FIG. 7 and a table linked to the master table.

(1) Mutation Analysis Process

An outline of mutation analysis will be described below with reference to FIGS. 25 and 26. Details of the mutation analysis is according to the method described in U.S. Patent Application Publication No. 2019/156914.

The test information management device C11 acquires a read (tumor read sequence) of a nucleic acid sequence derived from a tumor cell from a nucleic acid sample acquired from the first sample and acquires a read of a nucleic acid sequence derived from a normal cell (normal read sequence) from a nucleic acid sample acquired from the second sample, to use for the mutation analysis.

The test information management device C11 determines whether or not a tumor carried by a patient has a somatic mutation on the basis of the tumor read sequence and the normal read sequence. The normal read sequence is also used to determine whether the patient carries a germline mutation.

Detection of a somatic mutation and a germline mutation can be performed by comparing reference sequence data reported as a general sequence, with the tumor read sequence and the normal read sequence. For example, when comparing the reference sequence data and the first nucleic acid sequence data, a mutation in the tumor read sequence can be detected by detecting a sequence in the tumor read sequence different from a sequence in the reference sequence data. Similarly, when comparing the reference sequence data and the normal read sequence, a mutation in the normal read sequence can be detected by detecting a sequence in the normal read sequence different from a sequence in the reference sequence data. Instead of the reference sequence data, the mutation reference sequence data described in U.S. Patent Application Publication No. 2019-156914 may be used to detect a mutation.

Information regarding a germline mutation is not limited as long as the information is related to a germline mutation carried by the patient for which the nucleic acid sequence is analyzed. For example, the information regarding a germline mutation may include at least a label indicating a name of a gene in which the mutation has been detected. Preferably, the information regarding a germline mutation may include a label indicating a name of a gene in which the mutation has been detected, information on the detected nucleic acid sequence, and/or information on an amino acid sequence generated by the mutation. As described in the section of I. Outline of embodiment, locus information of the gene in which the mutation has been detected, reference sequence information, and information on a mutation sequence held by the patient may be included. The information regarding a germline mutation is not limited to the information on detection as to whether or not there is a mutation, but may be information implying possibility of a germline mutation (for example, a mosaic mutation).

(1-1) Detection of Somatic Mutation

With reference to FIGS. 12, 13, and 25, a description will be given to an example of an operation of the control unit 100 for the test information management device C11 to detect a somatic mutation.

In step ST201 of FIG. 25, the control unit 100 of the test information management device C11 (hereinafter, simply referred to as a test information management device C11) acquires a read sequence from the nucleic acid sequence data storage device 300 shown in FIG. 12. At this time, the control unit 100 of the test information management device C11 functions as the read sequence information acquisition unit 1 shown in FIG. 13. The acquired read sequence includes a normal read sequence and a tumor read sequence.

In step ST202 of FIG. 25, the test information management device C11 aligns each of the normal read sequence and the tumor read sequence with the reference sequence. At this time, the control unit 100 of the test information management device C11 functions as the sequence determination unit 2 shown in FIG. 13.

In step ST203 of FIG. 25, the test information management device C11 determines whether or not a mismatch with the reference sequence is present in the tumor read. When a mismatch with the reference sequence is present in the tumor read (when "Yes"), the process proceeds to ST204. Then, it is determined whether or not a mismatch with the reference sequence is absent in the normal read. When a mismatch with the reference sequence is absent in the normal read (when "Yes"), the process proceeds to step ST205. Then, the mutation existing in the tumor read is determined to be a somatic mutation. The test information management device C11 identifies a gene name, locus, and a mismatch site of the reference sequence corresponding to the read sequence having the mismatch.

In step ST206 of FIG. 25, the test information management device C11 searches the mutation database 7 on the basis of the detected mutation. The mutation database 7 in FIG. 13 is constructed based on the external mutation information database 400 such as COSMIC or ClinVar, for example. In one aspect, each piece of mutation information in the database may be assigned with metadata of information regarding a gene panel.

Next, in step ST207 of FIG. 25, the test information management device C11 assigns an annotation to the detected mutation on the basis of a search result of step ST206. FIG. 27 shows an example of the search result and the annotation. FIG. 27 includes information of, from the left, "mutation ID" showing identification information of a mutation, "CHROM" indicating a chromosome number including a mutation site, "POS" indicating a position number of the mutation site, "REF" indicating a nucleotide sequence of the reference sequence, "ALT" indicating a mutation sequence, and "Annotation" specifically indicating what kind of mutation it is. Assignment of the Annotation can be omitted.

When the test information management device C11 determines that the tumor read has no mismatch with the reference sequence ("No") in step ST203, the test information management device C11 determines in step ST208 that there is no somatic mutation. Then, the test information management device C11 ends the process.

After step ST207 in FIG. 25, the result shown in FIG. 27 may be outputted. In steps ST203 to ST207 shown in FIG. 25, the control unit 100 of the test information management device C11 functions as the mutation detection unit 3 shown in FIG. 13.

(1-2) Detection of Germline Mutation

Figure 26:
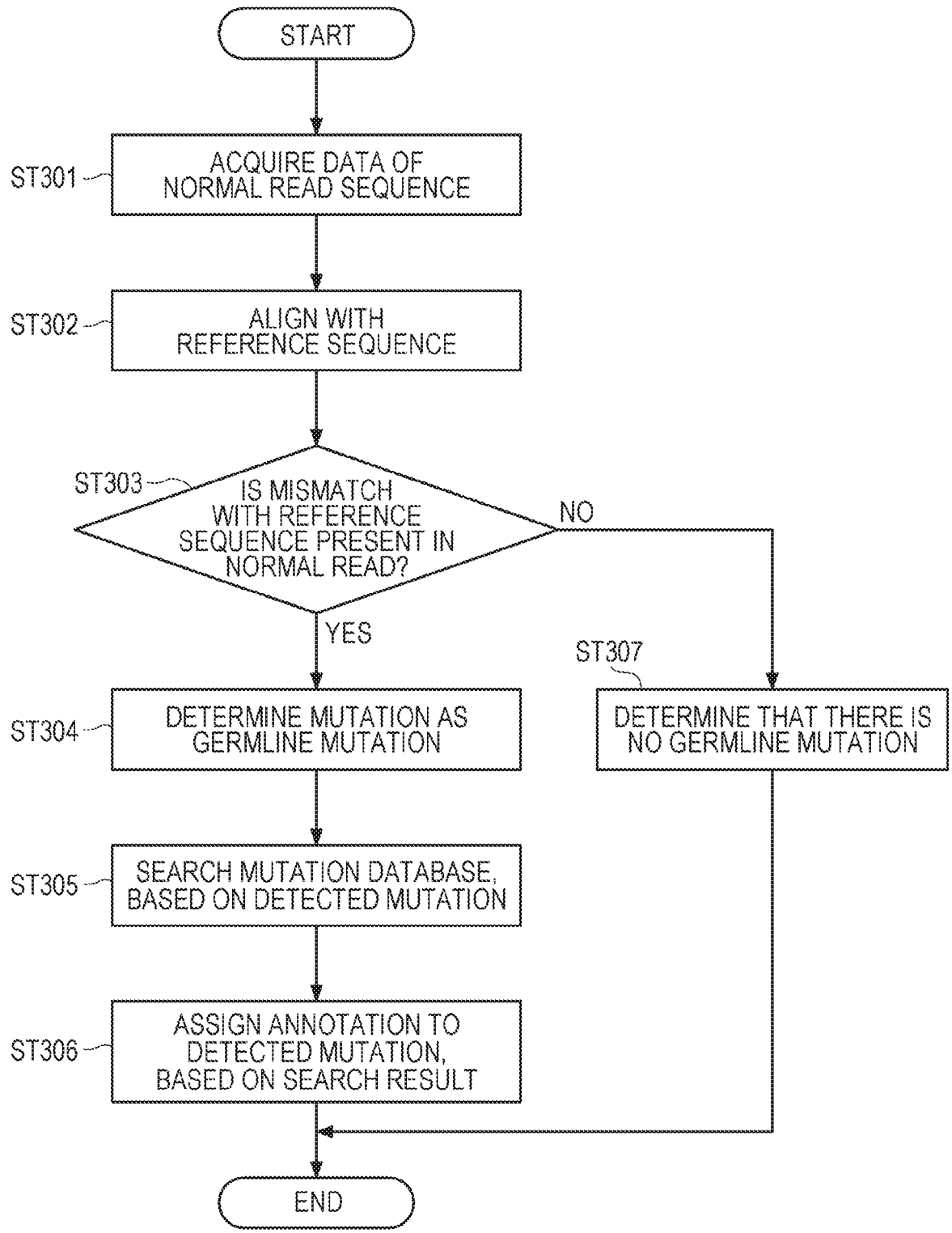
FIG. 26 shows a flowchart of mutation analysis.

With reference to FIGS. 12, 13, and 26, a description will be given to an example of an operation of the control unit 100 for the test information management device C11 to detect a germline mutation.

In step ST301 of FIG. 26, the test information management device C11 acquires a read sequence from the nucleic acid sequence data storage device 300 shown in FIG. 12. At this time, the control unit 100 of the test information management device C11 functions as the read sequence information acquisition unit 1 in FIG. 13. The acquired read sequence includes a normal read sequence.

In step ST302 of FIG. 26, the test information management device C11 aligns the normal read sequence with the reference sequence. At this time, the control unit 100 of the test information management device C11 functions as the sequence determination unit 2 shown in FIG. 13.

In step ST303 of FIG. 26, the test information management device C11 determines whether or not the normal read has a mismatch with the reference sequence. When there is a mismatch with the reference sequence in the normal read (when "Yes"), the mutation detection unit 3 proceeds to ST304. Then, the mutation detection unit 3 determines that the mutation existing in the normal read is a germline mutation. The test information management device C11 identifies a gene name, locus, and a mismatch site of the reference sequence corresponding to the read sequence having the mismatch.

In step ST305 of FIG. 26, the test information management device C11 searches the mutation database 7 shown in FIG. 13 on the basis of the identified mutation.

Next, in step ST306 of FIG. 26, the test information management device C11 assigns an annotation to the detected mutation on the basis of a search result of step ST305. This step is similar to step ST207 in FIG. 25.

When the test information management device C11 determines that the normal read has no mismatch with the reference sequence ("No") in step ST303 of FIG. 26, the test information management device C11 determines that there is no germline mutation in step ST307. Then, the test information management device C11 ends the process. In steps ST303 to ST306 shown in FIG. 26, the control unit 100 of the test information management device C11 functions as the mutation detection unit 3 shown in FIG. 13.

(2) Attribute Information Acquisition Process

With reference to FIGS. 12, 13, and 28A to 28C to 31, an operation for the test information management device C11 to acquire attribute information will be described.

In a test item of gene panel testing, mutation analysis of multiple genes is included in one panel. First attribute information and second attribute information comprehensively represent information on a mutation relating to a gene that is a target of the test item included in the gene panel testing. Therefore, the first attribute information is given with a "mutation present" label when a mutation is found in at least one gene to be tested (also referred to as a predetermined gene) included in the gene panel testing. When a mutation is found in at least one gene to be tested (also referred to as a predetermined gene) included in the gene panel testing, the second attribute information is also given with a label indicating a mutation type. For example, if both an actionable mutation and a germline mutation are found in single gene panel testing, labels of both will be given.

(2-1) First Acquisition Mode

A first acquisition mode of attribute information is a method in which the clinical technologist T1 or the bioinformatician T20 determines an attribute indicating an outline of a test result on the basis of the test result, and the clinical technologist T1 or the bioinformatician T20 inputs a determination result from the input unit 106 of the test information management device C11 shown in FIG. 12, and accordingly the test information management device C11 receives this input.

FIGS. 28A to 28C show an example of a graphical user interface for the clinical technologist T1 or the like to input attribute information to the test information management device C11, and an input example thereof. FIG. 28A shows a graphical user interface UIc in a case where a germline mutation has been reported in a test target gene of the gene panel testing. The graphical user interface UIc includes, as the first attribute information, a selection area UIc1 having a check box for selection as to whether or not a mutation has been detected in the test target gene, and an input field for input of the number of mutations. The graphical user interface UIc also includes, as the second attribute information, a selection area UIc2 having a check box for selection as to whether or not an actionable mutation has been detected, whether or not a germline mutation has been detected, and whether another mutation has been detected, and an input field for input of the numbers of individual mutations. FIG. 28B shows a graphical user interface UId in a case where a germline mutation has not been reported in a test target gene of the gene panel testing. A selection area UId1 in FIG. 28B is similar to the selection area UIc1 in FIG. 28A. A selection area UId2 in FIG. 28B is similar to the selection area UIc2 in FIG. 28A except that there is no input field for a germline mutation.

The clinical technologist T1 or the like selects the corresponding check box in each selection area by using a mouse or the like, which is the input unit 106 shown in FIG. 12.

An input from the input unit 106 shown in FIG. 12 is recorded in fields of the first attribute information and the second attribute information of the test management table shown in FIG. 28C.

Input of whether or not there is attribute information from the input unit 106 shown in FIG. 12 may be performed by selecting corresponding attribute information from options of a label indicating an attribute in a list format. As selection of the list format, a pull-down type graphical user interface UIe shown in FIG. 29 can be exemplified.

An actionable mutation is intended to, for example, a mutation that can be expected to have therapeutic efficacy of 3A or more of evidence level classification shown in the "Clinical practice guidance for next-generation sequencing in cancer diagnosis and treatment". The evidence level classification of therapeutic efficacy is classified into seven stages of 1A, 1B, 2A, 2B, 3A, 3B and 4. "3A or more" is intended to be a mutation classified into any of 1A, 1B, 2A, 2B, and 3A. Information regarding what kind of gene mutation is classified at what evidence level can be acquired from "Table 2. Evidence Levels of Gene Panel Testing Results" (as of Aug. 21, 2017) in "Clinical practice guidance for next-generation sequencing in cancer diagnosis and treatment".

(2-2) Second Acquisition Mode

A second acquisition mode of attribute information is a method for acquiring the attribute information on the basis of a mutation detected by the test information management device C11 through the processing shown in FIGS. 25 and 26. With reference to FIGS. 30 to 32A and 32B, a process in which the test information management device C11 acquires attribute information will be described.

Figure 30:
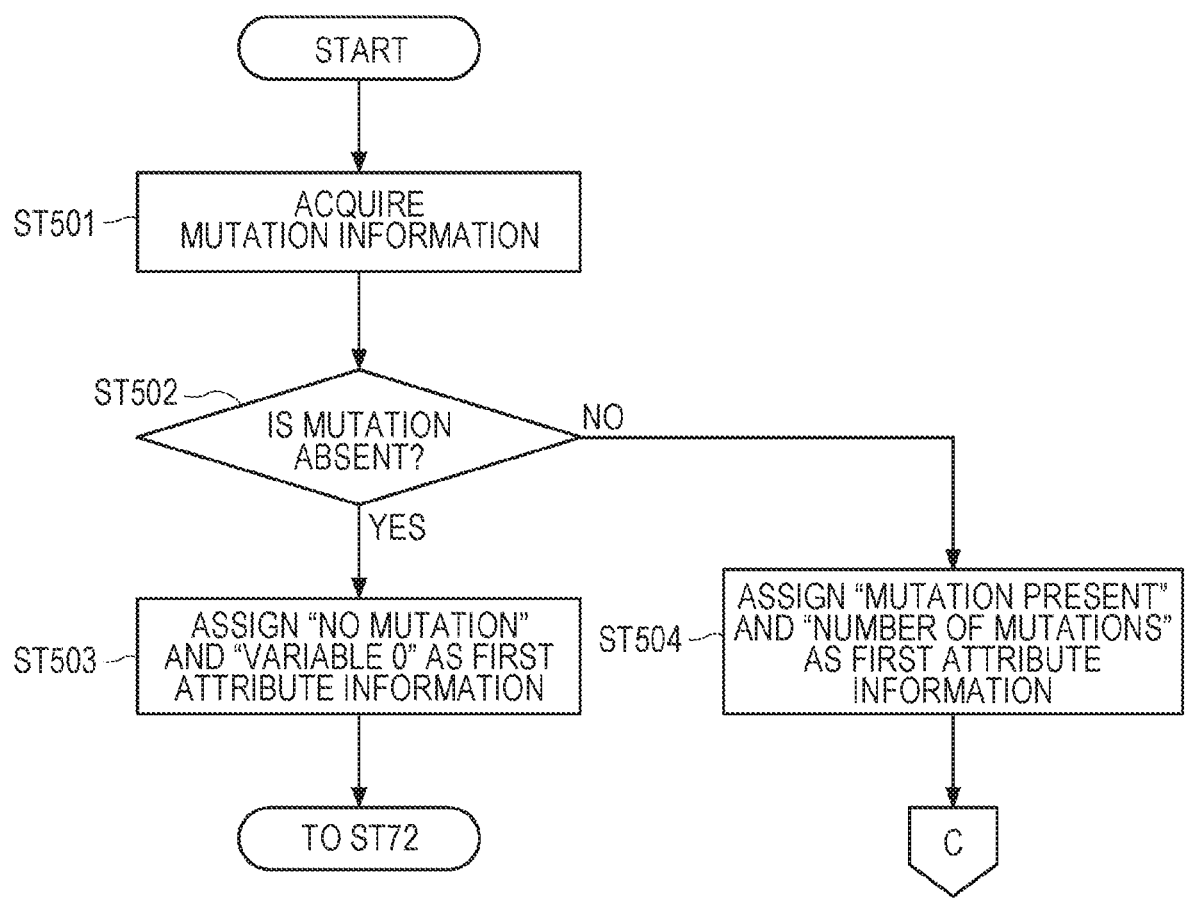
FIG. 30 shows a flowchart for the test information management device C11 to determine attribute information.
Figures 32A, 32B:
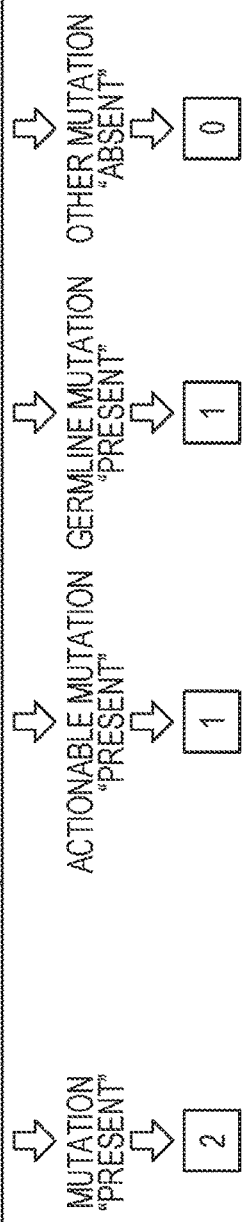
FIG. 32A shows an outline of a detection result table G.
FIG. 32B shows an outline of a determination table H.

In step ST501 of FIG. 30, the test information management device C11 acquires mutation information acquired through the processing shown in FIGS. 25 and 26. The mutation information is recorded in the storage device 103 as a detection result table G as shown in FIG. 32A, for example. For example, in FIG. 32A, the detection result table G includes a "data ID" field showing identification information of data acquired from the next-generation sequencer C13, a "test request ID" field, a "link to result report" field with a link to a folder that stores a test result, a "detected mutation" field showing a name of a gene in which a mutation has been detected, and a "panel ID" field showing a gene panel ID.

In step ST502 of FIG. 30, the test information management device C11 determines whether or not a mutation is absent in the result, on the basis of the mutation information acquired in step ST501. For example, the storage device 103 of the test information management device C11 has recorded a determination table shown in FIG. 32B in advance.

The determination table H in FIG. 32B is created for each gene panel ID. An example in which the gene panel ID is P001 is shown here. In the determination table H of FIG. 32B, a name of a gene in which a mutation can be detected in a gene panel of P001 is recorded in a "mutation targeted for first attribute information" field. The first attribute information of a gene mutation a, a gene mutation b, a gene mutation c, . . . a gene mutation i, and a gene mutation z, that is, the presence or absence of a mutation can be detected. A gene targeted for second attribute information is recorded separately for "actionable mutation", "germline mutation", and "other mutation". A gene mutation a and a gene mutation b are recorded in the "actionable mutation" field, a gene mutation h and a gene mutation i are recorded in the "germline mutation" field, and a gene mutation v, a gene mutation w, and a gene mutation x are recorded in the "other mutation" field.

In step ST502 of FIG. 30, the test information management device C11 determines whether or not the gene mutation a and the gene mutation i recorded in step ST501 and stored in the "detected mutation" field of the detection result table G shown in FIG. 32A are absent in the "mutation targeted for first attribute information" field of the determination table H of FIG. 32B.

When the "mutation targeted for first attribute information" field of the determination table H of FIG. 32B has no gene mutation stored in the "detected mutation" field of the detection result table G, step ST502 in FIG. 30 is to be YES. In this case, the test information management device C11 proceeds to step ST503 in FIG. 30. Then, the test information management device C11 assigns and records a "no mutation" label and a variable "0" into the first attribute information field of the test management table L shown in FIG. 28C.

In the example of FIGS. 32A and 32B, since there are the gene mutation a and the gene mutation i in the "mutation targeted for first attribute information" field of the determination table H, step ST502 of FIG. 30 is to be NO. In this case, the test information management device C11 proceeds to step ST504 in FIG. 30. Then, the test information management device C11 assigns the "mutation present" label into the first attribute information field of the test management table L shown in FIG. 28C. Alternatively, the test information management device C11 counts how many gene mutations are stored in the "detected mutation" field of the detection result table G shown in FIG. 32A. Then, the test information management device C11 assigns and records the number as a label of the number indicating the number of mutations in the first attribute information field. In the example of FIG. 32A, the number of mutations is "2".

Figure 31:
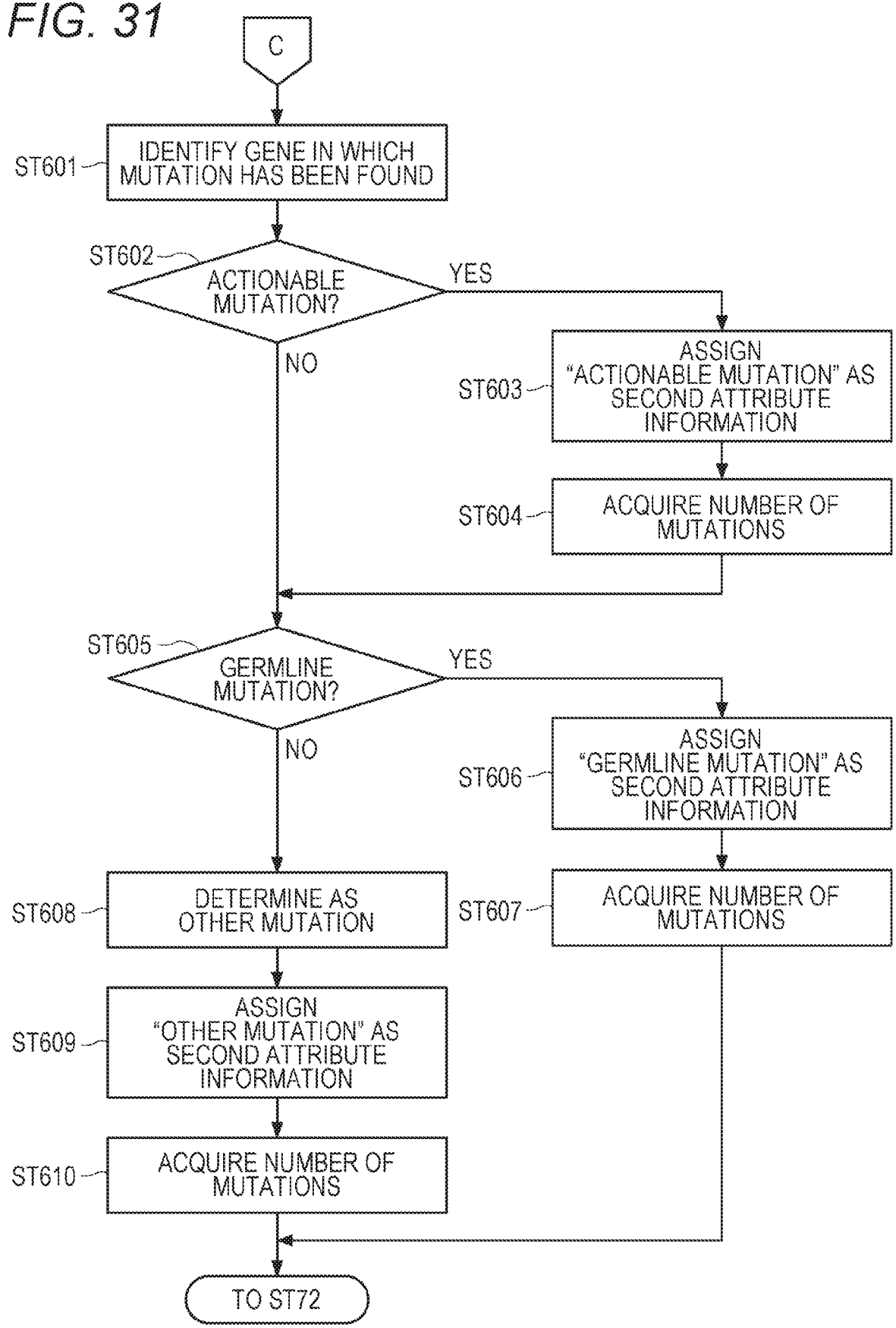
FIG. 31 shows a flowchart for the test information management device C11 to determine attribute information.

Next, the test information management device C11 proceeds to step ST601 in FIG. 31.

In FIG. 31, the second attribute information, that is, a mutation type is determined.

Next, in step ST601 of FIG. 31, the test information management device C11 identifies a gene in which a mutation has been found. For the identification of the gene having a mutation, a search is performed to determine, in the "mutation targeted for second attribute information" field of the determination table H of FIG. 32B, which mutation field has the gene mutation a and the gene mutation i recorded in step ST501 of FIG. 30 and stored in the "detected mutation" field of the detection result table G shown in FIG. 32A.

When the gene stored in the "detected mutation" field of the detection result table G shown in FIG. 32A is in the "actionable mutation" field of the determination table H of FIG. 32B, step ST602 of FIG. 31 is to be YES, and the test information management device C11 proceeds to step ST603 in FIG. 31. Then, a label indicating that there is "actionable mutation" is given and recorded in the "second attribute information" field of the test management table L shown in FIG. 28C. Subsequently, the test information management device C11 proceeds to step ST604. The test information management device C11 counts how many mutations among gene mutations stored in the "detected mutation" field of the detection result table G shown in FIG. 32A are in the "actionable mutation" field of the determination table H of FIG. 32B. Then, the test information management device C11 assigns and records the counts as a label indicating the number of mutations, in the field of the number of "second attribute information" of the test management table L shown in FIG. 28C. In the example of FIG. 32A, the number of mutations of the actionable mutation is "1".

When a gene stored in the "detected mutation" field of the detection result table G shown in FIG. 28A is not in the "actionable mutation" field of the determination table H of FIG. 32B (when step ST602 of FIG. 31 is NO) and after step ST604 in FIG. 31, the test information management device C11 proceeds to step ST605 in FIG. 31.

When the gene is in the "germline mutation" field of the determination table H in FIG. 32B, step ST605 in FIG. 31 is to be YES, and the test information management device C11 proceeds to step ST606 in FIG. 31. Then, a label indicating that there is "germline mutation" is given and recorded in the "second attribute information" field of the test management table shown in FIG. 28C. Subsequently, the test information management device C11 proceeds to step ST607. The test information management device C11 counts how many mutations among gene mutations stored in the "detected mutation" field of the detection result table G shown in FIG. 32A are in the "germline mutation" field of the determination table H of FIG. 32B. Then, the test information management device C11 assigns and records the counts as a label indicating the number of mutations, in the field of the number of "second attribute information" of the test management table L shown in FIG. 28C. In the example of FIG. 32A, the number of mutations of the germline mutation is "1". The test information management device C11 ends the post-processing of step ST607.

When the gene stored in the "detected mutation" field of the detection result table G shown in FIG. 32A is not in the "germline mutation" field of the determination table H of FIG. 32B (when step ST605 of FIG. 31 is NO), the test information management device C11 proceeds to step ST608 of FIG. 31. Then, in step ST609 of FIG. 31, a label indicating that there is "other mutation" is given and recorded in the "second attribute information" field of the test management table shown in FIG. 28C. Subsequently, the test information management device C11 proceeds to step ST610. The test information management device C11 counts how many mutations among gene mutations stored in the "detected mutation" field of the detection result table G shown in FIG. 32A are in the "other mutation" field of the determination table H of FIG. 32B. The test information management device C11 assigns and records the counts as a label indicating the number of mutations, in the field of the number of "second attribute information" of the test management table L shown in FIG. 28C. In the example of FIG. 32A, the number of mutations of the other mutation is "0". The test information management device C11 ends the post-processing of step ST607.

The attribute information recorded in the test management table L by the attribute information acquisition process is transmitted to the integrated data management device A in step ST72 of FIG. 19.

In steps ST501 to ST504 shown in FIG. 30 and steps ST601 to ST610 shown in FIG. 31, the control unit 100 of the test information management device C11 functions as the attribute information acquisition unit 4 shown in FIG. 13.

(3) Report

The test information management device C11 generates a test report (report) of a test result acquired by the processing shown in FIGS. 25 and 26.

An example of a format of a report R1 will be described with reference to FIG. 33. The format of the report R1 is an example including an area S of a summary report, which is a first area (hereinafter, also referred to as "summary report area S"), and an area DT of a detailed report, which is a second area (hereinafter, also referred to as "detailed report area DT"). The summary report area S further includes an area S1 showing a part of test request information indicating information regarding a patient or a test content (hereinafter, also referred to as "request information area S1"), and an area S2 showing a list of all detected gene mutations (hereinafter, also referred to as "mutation list area S2"). The detailed report area DT includes an area DT1 showing detailed information of a gene and a mutation thereof detected in a nucleic acid sequence derived from a first sample (containing a tumor cell) (hereinafter, also referred to as "gene mutation information area DT1"), and an area DT2 showing detailed information of a gene and a mutation thereof in which a germline mutation has been detected in a nucleic acid sequence derived from a second sample (containing a non-tumor cell) (hereinafter, also referred to as "germline mutation information area DT2").

In FIG. 33, an attribute information area S1 may display information for identification of a patient such as a patient identifier (ID), a name of a doctor in charge, and a name of a medical facility, and information indicating a test item such as a gene panel. The gene mutation list area S2 may display all detected gene mutations regardless of being a somatic mutation or a germline mutation. In the example of the gene mutation list area S2 shown in FIG. 33, EGFR, BRAF, and BRCA1 represent gene names, and L858R, V600E, and K1183R represent mutation sites. Therefore, EGFR_L858R indicates that a codon at the 858th amino acid of the EGFR gene is mutated from a nucleic acid sequence encoding leucine (L) to a nucleic acid sequence encoding arginine (R).

The summary report area S is an area that may be displayed to the patient, the doctor in charge, an expert in gene analysis, and the like.

The gene mutation information area DT1 may include information such as a name of a gene in which a mutation has been detected, a mutation identifier (ID), a locus number of a gene in which a mutation has been detected (including chromosome number: CROM and mutation position: POS), a nucleic acid sequence of a reference sequence (REF), a detected mutation sequence (ALT), and an annotation when showing a detected mutation in an analysis report.

The germline mutation information area DT2 may include information such as a name of a gene in which a mutation has been detected, a mutation identifier (ID), a locus number of a gene in which a mutation has been detected (including chromosome number: CROM and mutation position: POS), a nucleic acid sequence of a reference sequence (REF), a detected mutation sequence (ALT), and an annotation when showing a detected mutation in an analysis report.

In the example of FIG. 33, the germline mutation information area DT2 shows that there is a germline mutation "BRCA1_K1183R" in the BRCA1 gene, and "BRCA1_K1183R" is also shown in the gene mutation list area S2 of the summary report area S. In other words, the report R1 shown in FIG. 33 presents the germline mutation "BRCA1_K1183R" shown in the gene mutation list area S2 to the patient.

In the example of FIG. 33, there is further provided an additional information area AP that displays drug information, clinical trial information, article information, and the like, which are information indicating clinical significance. The example of FIG. 33 shows related tumor names corresponding to the detected gene mutations, and drugs that may be applied. Since the detected "EGFR_L858R" mutation and "BRAF_V600E" mutation are actionable mutations, drug information is displayed. Since "BRCA1_K1183R" is a germline mutation, drug information is not displayed. In addition to this, when the detected mutation is another mutation, clinical trial information and/or article information, or a URL linked to each piece of the information can be displayed. The information displayed in the additional information area AP may be acquired from the additional information database APD shown in FIG. 13 corresponding to each gene mutation.

8-3. Expert Meeting Setting

Returning to FIG. 20, a continuation of the operation of the system 1000 will be described.

Figure 20:
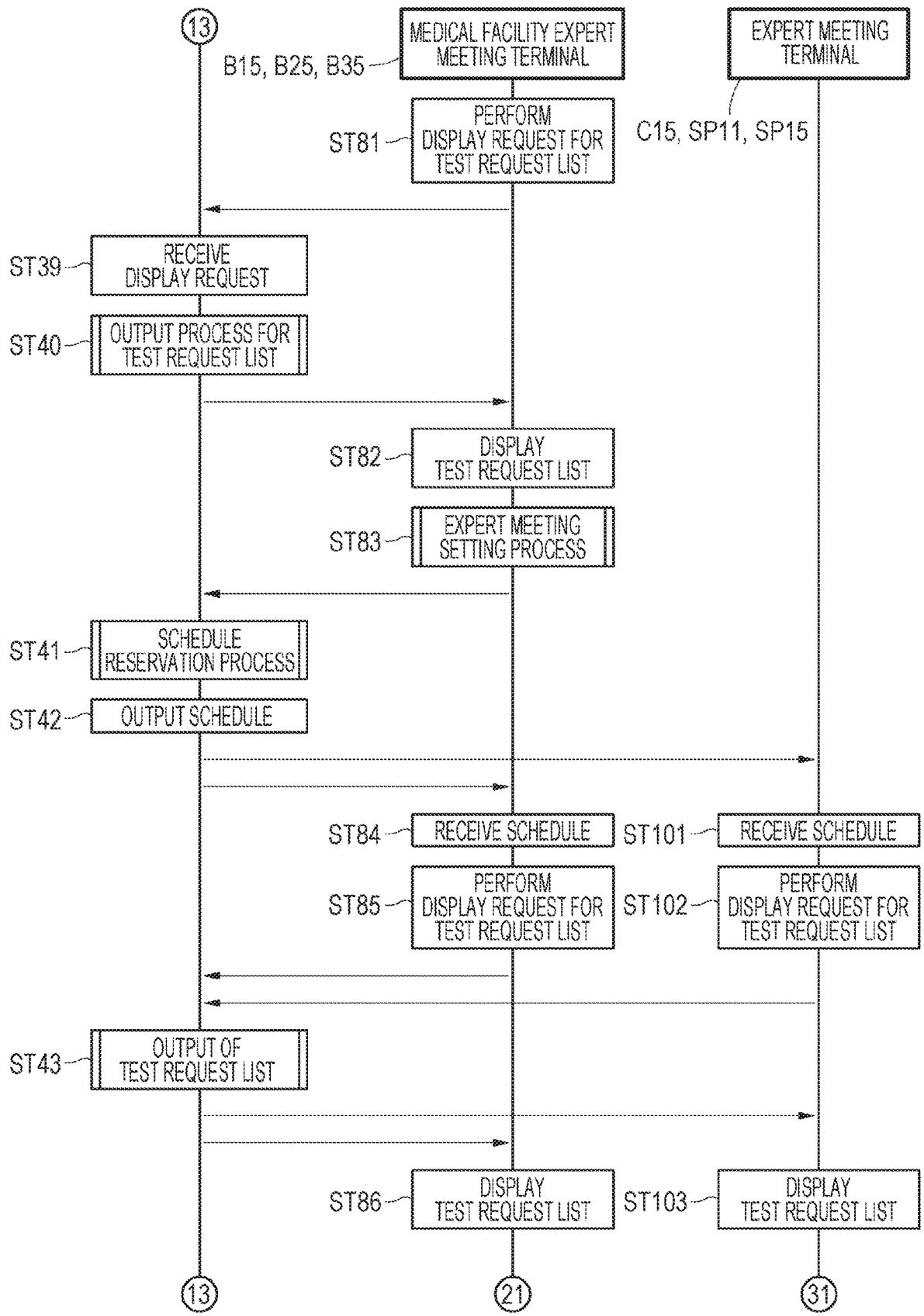
FIG. 20 is a flowchart showing a part of an operation of the system 1000.
Figure 21:
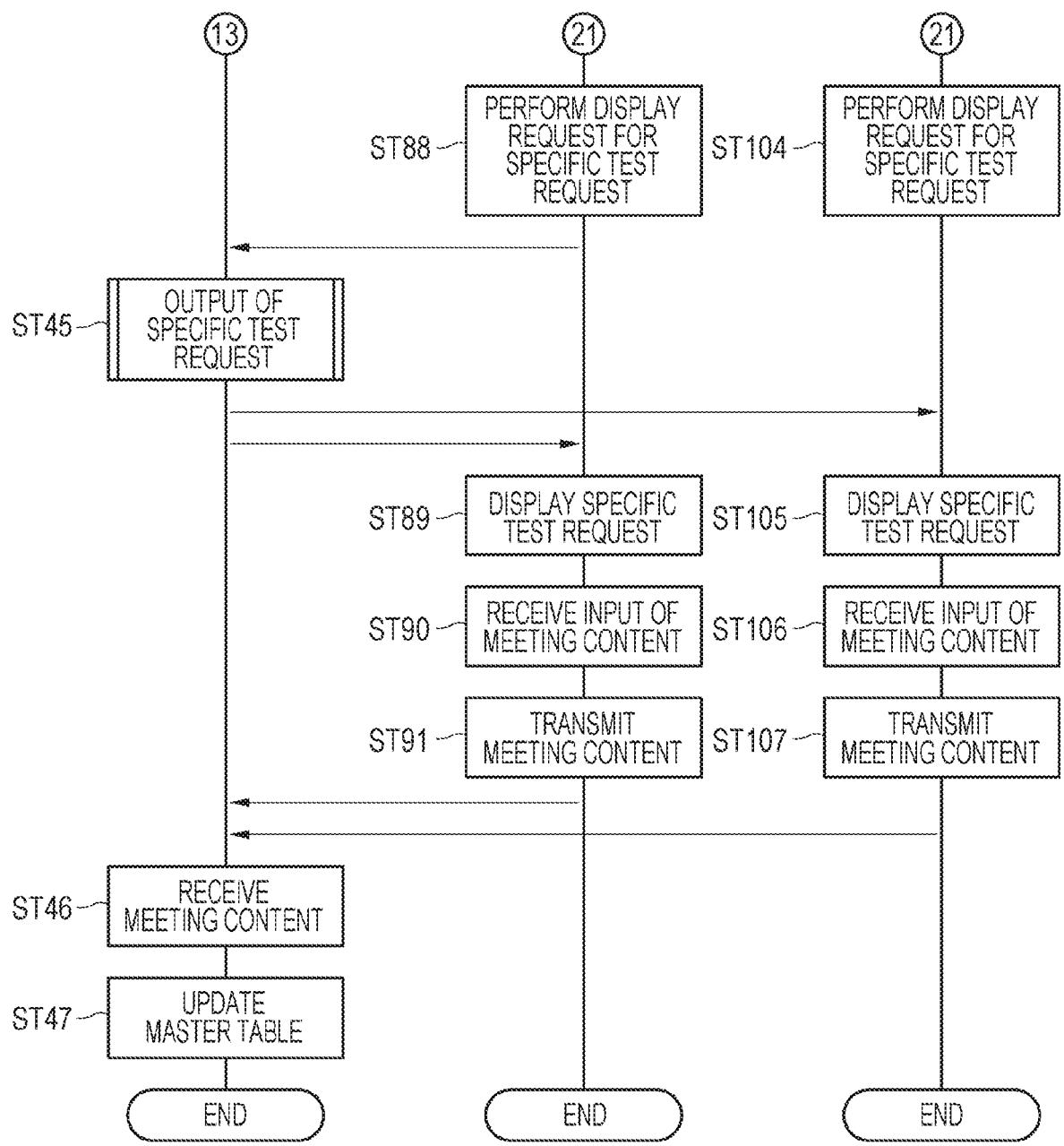
FIG. 21 is a flowchart showing a part of an operation of the system 1000.

The operation of the system shown in FIGS. 20 and 21 is to be communication of the integrated data management device A between with the expert meeting terminals B15, B25, and B35 of the medical facilities B1, B2, and B3, the expert meeting terminal C15 of the test facility C1, the expert meeting terminal SP11, and the bureau expert meeting terminal SP15.

With reference to FIGS. 12 to 17, 19, and 20, a display process for a test request list and an expert meeting setting process in the system 1000 will be described. Since the expert meeting terminal B15 of the medical facility B1, the expert meeting terminal B25 of the medical facility B2, and the expert meeting terminal B35 of the medical facility B3 have the same processing content, processing will be described using the expert meeting terminal B15 of the medical facility B1.

When the doctor in charge H1a displays a test result of a patient for which gene panel testing is requested, the doctor in charge H1a accesses the integrated data management device A via browser software, from the expert meeting terminal B15 of the medical facility B1 provided in the medical facility B1. In step ST81 of FIG. 20, the control unit 100X of the expert meeting terminal B15 of the medical facility B1 shown in FIG. 14 (hereinafter, simply referred to as "expert meeting terminal B15 of the medical facility B1") receives a display request for the test request list UI1 shown in FIG. 9, from the doctor in charge H1a via the input unit 106X. Then, the display request for the test request list UI1 is transmitted to the integrated data management device A via the I/F unit 105X. At this time, the control unit 100X functions as the test request list display request unit X5 shown in FIG. 15.

In step ST39 shown in FIG. 20, the integrated data management device A receives the display request from the expert meeting terminal B15 of the medical facility B1. Subsequently, the integrated data management device A outputs the test request list UI1 shown in FIG. 9 in step ST40 shown in FIG. 20. At this time, the control unit 100A functions as the test request list output unit A19 shown in FIG. 6.

In step ST82, the expert meeting terminal B15 of the medical facility B1 displays the test request list UI1 shown in FIG. 9 outputted from the integrated data management device A, on the output unit 107X such as a display via browser software. At this time, the control unit 100X functions as the test request list output unit X7 shown in FIG. 15.

The doctor in charge H1a sets a schedule of an expert meeting from the expert meeting terminal B15 of the medical facility B1. In step ST83, the expert meeting terminal B15 of the medical facility B1 receives a setting of a meeting schedule by the doctor in charge H1a from the input unit 106X shown in FIG. 14. At this time, the control unit 100X functions as the schedule setting unit X1 shown in FIG. 15. Details of the setting process for the expert meeting will be described later.

The integrated data management device A performs a schedule setting process in ST41 shown in FIG. 20. Details of the schedule setting process will be described later. At this time, the control unit 100A functions as the schedule update unit A20 shown in FIG. 6.

Subsequently, the integrated data management device A outputs the set expert meeting schedule in step ST42 of FIG. 20. This output is, for example, transmission of the expert meeting schedule to each participant in the expert meeting, by using mail software. At this time, the control unit 100A functions as the schedule output unit A21 shown in FIG. 6.

The mail of the expert meeting schedule transmitted from the integrated data management device A is received by mail software of the expert meeting terminal B15 of the medical facility B1 in step ST84 of FIG. 20. At this time, the control unit 100X functions as the schedule reception unit X3 shown in FIG. 15. In step ST101 of FIG. 20, mail software of the expert meeting terminal SP11 also receives the mail of the expert meeting schedule. At this time, the control unit 100Y shown in FIG. 14 functions as the schedule reception unit Y1 shown in FIG. 16.

Prior to the expert meeting, each participant in the expert meeting can display a test request list of a patient to be examined in the expert meeting on each expert meeting terminal.

In the following, the expert meeting terminal B15 of the medical facility B1 and the expert meeting terminal SP11 can display the test request list by similar processing.

An example of communication between the expert meeting terminal B15 of the medical facility B1 and the integrated data management device A will be described first.

The doctor in charge H1a accesses the integrated data management device A via browser software, from the expert meeting terminal B15 of the medical facility B1 provided in the medical facility B1.

In step ST85 of FIG. 20, the expert meeting terminal B15 of the medical facility B1 shown in FIG. 14 receives a display request for the test request list UI1 shown in FIG. 9, from the doctor in charge H1a from the input unit 106X. Then, the display request for the test request list UI1 is transmitted to the integrated data management device A via the I/F unit 105X. At this time, the control unit 100X functions as the test request list display request unit X5 shown in FIG. 15.

In step ST43 shown in FIG. 20, the integrated data management device A receives the display request from the expert meeting terminal B15 of the medical facility B1. Then, the integrated data management device A outputs the test request list UI1 shown in FIG. 9. At this time, the control unit 100A functions as the test request list output unit A19 shown in FIG. 6.

In step ST86, the expert meeting terminal B15 of the medical facility B1 displays the test request list UI1 shown in FIG. 9 outputted from the integrated data management device A, on the output unit 107X such as a display via browser software. At this time, the control unit 100X functions as the test request list output unit X7 shown in FIG. 15.

Each participant can request display for a specific test request assigned to the participant in the expert meeting handled by the participant. For example, by providing a sorting function and an extraction function in the test request list, the participant can rearrange the test request list in accordance with the "holding date and time" of the expert meeting, and extract the test request assigned to the participant with the "group ID" of the expert meeting participated by the participant. Step ST88 shown in FIG. 21 is a step in which the expert meeting terminal B15 of the medical facility B1 makes a display request for such a specific test request. In this step, the control unit 100X functions as the test request list display request unit X5.

In step ST45 shown in FIG. 21, the integrated data management device A receives a display request from the expert meeting terminal B15 of the medical facility B1. Then, the integrated data management device A outputs a specific test request from the test request list UI1 shown in FIG. 9. At this time, the control unit 100A functions as the test request list output unit A19 shown in FIG. 6. The output process for the specific test request will be described later.

In step ST89, the expert meeting terminal B15 of the medical facility B1 displays the test request list UI1 shown in FIG. 9 outputted from the integrated data management device A, on the output unit 107X such as a display via browser software. At this time, the control unit 100X functions as the specific test request list output unit X9 shown in FIG. 15.

The expert meeting terminal B15 of the medical facility B1 receives an input of a meeting content by the doctor in charge H1a from the input unit 106X shown in FIG. 14 in the expert meeting (step ST90). At this time, the control unit 100X functions as the meeting content acquisition unit X17 shown in FIG. 15. Subsequently, in step ST91, the expert meeting terminal B15 of the medical facility B1 transmits the meeting content received in step ST90 to the integrated data management device A. At this time, the control unit 100X functions as the meeting content output unit X19 shown in FIG. 15.

In step ST46, the integrated data management device A receives the meeting content transmitted from the expert meeting terminal B15 of the medical facility B1. In step ST47, the integrated data management device A records the meeting content in the integrated database OG in association with the test request ID and the patient information, to update the master table.

The expert meeting terminal C15 of the test facility C1, the expert meeting terminal SP11 of the external facility SP1, and the bureau expert meeting terminal SP15 perform, in steps ST101 to ST107 of FIGS. 20 and 21, similar processing to that of steps ST84 to ST91 performed by the expert meeting terminal B15 of the medical facility B1.

Regarding the processing performed by the expert meeting terminal C15 of the test facility C1 and the expert meeting terminal SP11 of the external facility SP1, the control unit 100X, the I/F unit 105X, the input unit 106X, and the output unit 107X of the expert meeting terminal B15 of the medical facility B1 shown in FIG. 14 are to be replaced with the control unit 100Y, the I/F unit 105Y, the input unit 106Y, and the output unit 107Y of the expert meeting terminal C15 of the test facility C1 or the expert meeting terminal SP11 shown in FIG. 14. The schedule reception unit X3, the test request list display request unit X5, the test request list output unit X7, and the specific test request list output unit X9 showing functions of the control unit 100X of the expert meeting terminal B15 of the medical facility B1 shown in FIG. 15 are to be replaced with the schedule reception unit Y1, the test request list display request unit Y3, the test request list output unit Y5, and the specific test request list output unit Y7 shown in FIG. 16, respectively.

Regarding the processing performed by the bureau expert meeting terminal SP15, the control unit 100X, the I/F unit 105X, the input unit 106X, and the output unit 107X of the expert meeting terminal B15 of the medical facility B1 shown in FIG. 14 are to be replaced with the control unit 100Z, the I/F unit 105Z, the input unit 106Z, and the output unit 107Z of the bureau expert meeting terminal SP15 shown in FIG. 14. The schedule reception unit X3, the test request list display request unit X5, the test request list output unit X7, the specific test request list output unit X9, the meeting content acquisition unit X17, and the meeting content output unit X19 showing functions of the control unit 100X of the expert meeting terminal B15 of the medical facility B1 shown in FIG. 15 are to be replaced with the schedule reception unit Z1, the test request list display request unit Z3, the test request list output unit Z5, the specific test request list output unit Z7, the meeting content acquisition unit Z13, and the meeting content output unit Z15 shown in FIG. 17.

(1) Recording of Candidate Slot for New Expert Meeting Holding Date and Time

Figure 34:
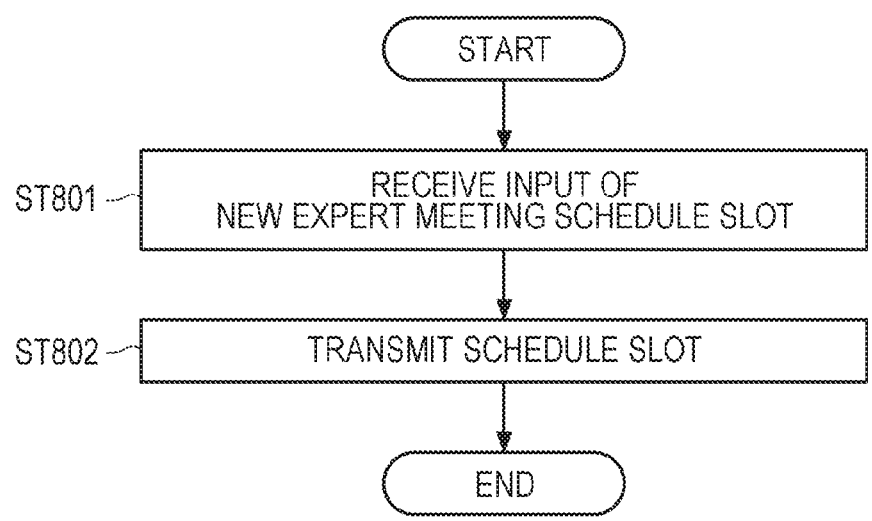
FIG. 34 shows a registration process of a new expert meeting schedule slot in the bureau expert meeting terminal SP15.

FIG. 34 shows a recording process for a candidate slot for a new meeting holding date and time, which is performed by the bureau expert meeting terminal SP15. The control unit 100Z of the bureau expert meeting terminal SP15 (hereinafter, also simply referred to as "bureau expert meeting terminal SP15") records, in the meeting schedule database SDB, a candidate slot for a new meeting holding date and time for display in a graphical user interface for the integrated data management device A to receive a setting of an expert meeting from a doctor in charge.

A staff of a facility that leads the expert meeting inputs a new meeting schedule slot from the input unit 106Z of the bureau expert meeting terminal SP15 shown in FIG. 14.

In step ST801 of FIG. 34, the bureau expert meeting terminal SP15 receives the input of the new meeting schedule slot from the input unit 106Z shown in FIG. 14. At this time, the control unit 100Z of the bureau expert meeting terminal SP15 functions as the new reservation slot registration unit Z17 shown in FIG. 17.

In step ST802 of FIG. 34, the bureau expert meeting terminal SP15 transmits the information inputted in step ST801 of FIG. 34 to the integrated data management device A. At this time, the control unit 100Z of the bureau expert meeting terminal SP15 functions as the schedule update unit Z19 shown in FIG. 17. The transmitted information is recorded in the meeting schedule database SDB by the integrated data management device A.

FIG. 35A shows a form of a candidate schedule table MS, which is one embodiment of a meeting schedule candidate table to be recorded in the meeting schedule database SDB. The candidate schedule table MS is managed with the number of acceptable entries. The candidate schedule table MS is provided with a field for recording a group ID of an expert meeting group to which the doctor in charge belongs, a field for recording a bureau facility ID of the expert meeting, a field for recording a time category ID indicating a time category of required time for the expert meeting, a field for recording a candidate slot of a meeting holding date and time, and a field for recording the number of meetings that can be accepted in the candidate slot of the meeting holding date and time.

FIG. 35B shows a form of a candidate schedule table MS2, which is another embodiment of a meeting schedule candidate table to be recorded in the meeting schedule database SDB. In the candidate schedule table MS2, a candidate schedule is managed with vacant time. The candidate schedule table MS2 is provided with a field for recording a group ID of an expert meeting group to which the doctor in charge belongs, a field for recording a bureau facility ID of the expert meeting, a field for recording a candidate slot of a meeting holding date and time, a field for recording a setting status according to required time for the expert meeting, a field for recording an allocated time [Total time (min)] of a candidate slot of the meeting holding date and time, a field for recording time (min) in which the meeting is set in the candidate slot of the meeting holding date and time, and a field for recording vacant time (min) in the candidate slot of the meeting holding date and time. In the field for recording the setting status, a recording field is provided for each time category ID.

(2) Expert Meeting Setting

With reference to FIG. 36 to FIG. 46, a description is given to details of the graphical user interface UI that is for setting of an expert meeting, a test request list output process of step ST40 shown in FIG. 20, an expert meeting setting process in step ST83, and the schedule setting process in step ST41.

(2-1) Graphical User Interface

FIG. 36 shows an example of the graphical user interface UI that enables setting of an expert meeting. A "setting status" area of the test request list UI1 displays a label of "set" or "unset" indicating whether or not a schedule of an expert meeting has been set. When the schedule of the expert meeting has been set, the set date and time is displayed in a "holding date and time" area. When the schedule of the expert meeting has not been set, "-" is shown in the "holding date and time" area.

(2-2) Dialog Display

Figure 37:
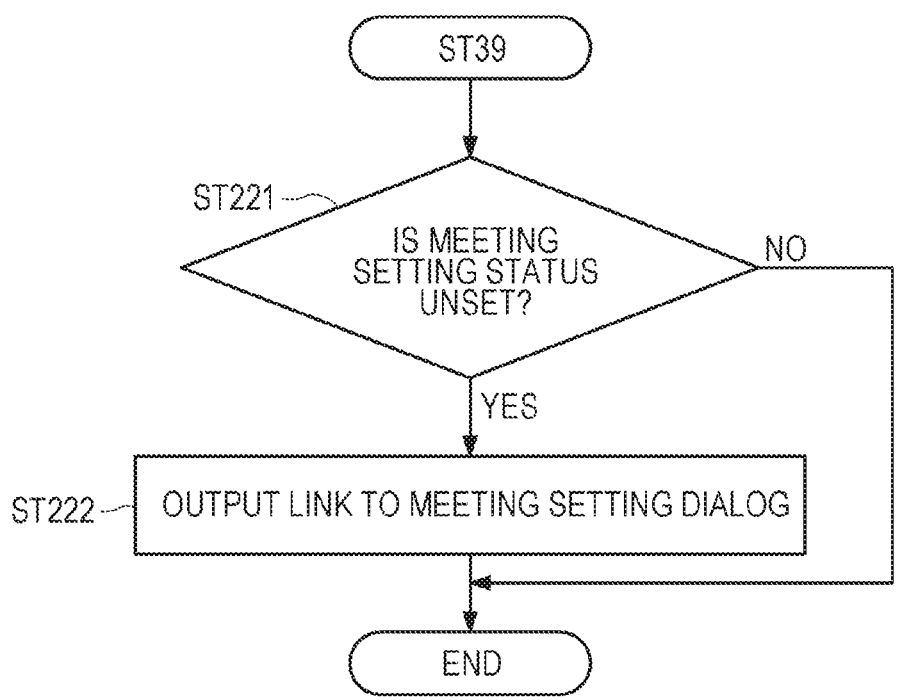
FIG. 37 is a flowchart of a process for displaying a link for setting an expert meeting on a graphical user interface UI, in the integrated data management device A.

FIG. 37 shows a process in which the integrated data management device A displays a link to dialog for setting an expert meeting in the "setting status" field of the graphical user interface UI shown in FIG. 36.

In step ST221 of FIG. 37, the integrated data management device A determines whether or not the setting status of the expert meeting is unset. This determination can be made based on whether or not a holding date and time has been inputted in the "holding date and time" field of each test request ID in the master table M shown in FIG. 7.

When the holding date and time is not recorded in the "holding date and time" field of the master table M shown in FIG. 7 (when step ST221 is "Yes"), the integrated data management device A outputs the "unset" label to the "setting status" field of the graphical user interface UI shown in FIG. 36, in step ST222 of FIG. 37. The "unset" label is provided with a link for outputting an operation screen such as the dialog UI51 shown in FIG. 3A and the dialog UI52 shown in FIG. 3B, and the dialog UI55 shown in FIG. 43D, the dialog UI56 shown in FIG. 43E, the dialog UI57 shown in FIG. 47D, the dialog UI58 shown in FIG. 47E, or the dialog UI60 shown in FIG. 53D, which will be described later.

(2-3) Medical Facility Expert Meeting Terminal Side

A specific step of the expert meeting setting process in step ST83 shown in FIG. 20 will be described with reference to FIG. 38.

Figure 38:
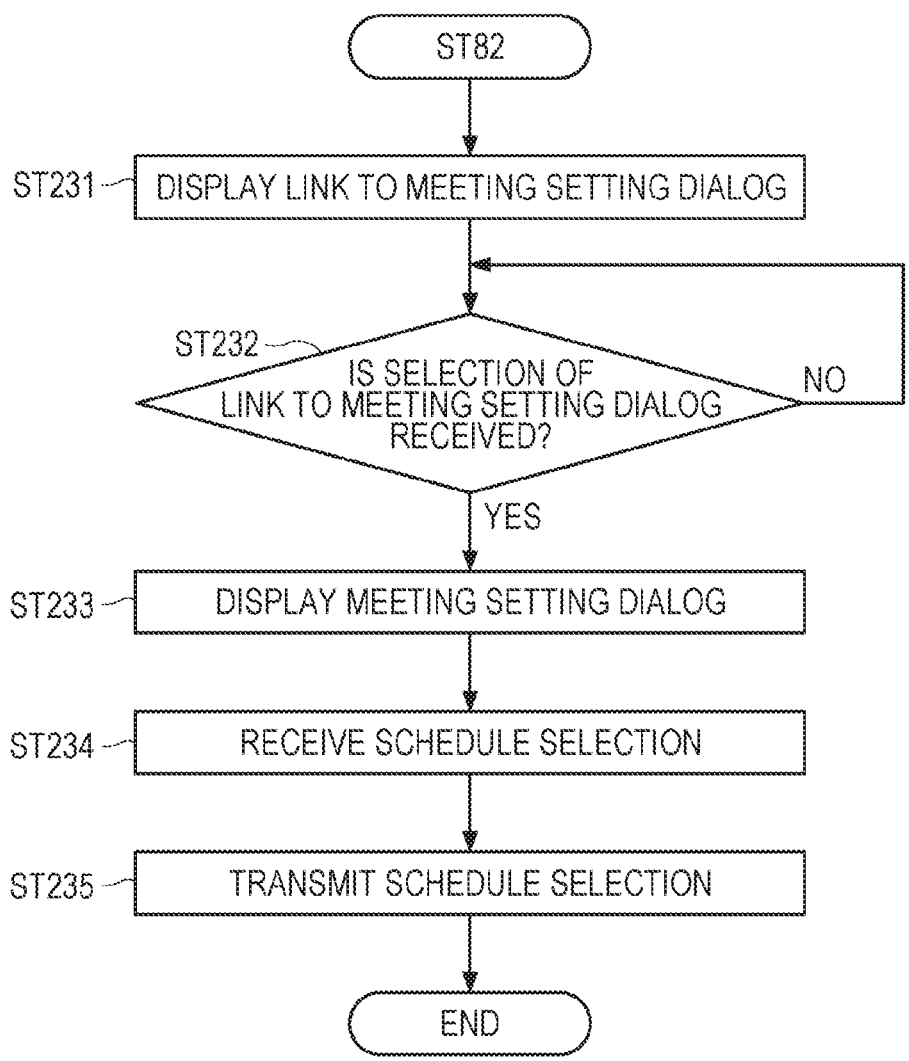
FIG. 38 shows a flowchart of a display process in the expert meeting terminals B15, B25, and B35 of a medical facility.

In step ST231 shown in FIG. 38, the expert meeting terminal B15 of the medical facility B1 uses browser software to display the "unset" label including a link to expert meeting setting dialog outputted by the integrated data management device A in step ST222 of FIG. 37.

The expert meeting terminal B15 of the medical facility B1 determines, in step ST232 shown in FIG. 38, whether selection of the link by the doctor in charge H1a from the input unit 106X has been received.

When the expert meeting terminal B15 of the medical facility B1 receives the selection of the link to the expert meeting setting dialog in step ST232 shown in FIG. 38 (when "Yes"), the expert meeting terminal B15 proceeds to step ST233. Then, the expert meeting terminal B15 displays, on the output unit 107X such as a display of the expert meeting terminal B15 of the medical facility B1, the dialog UI51 shown in FIG. 3A, the dialog UI52 shown in FIG. 3B, the dialog UI55 shown in FIG. 43D, the dialog UI56 shown in FIG. 43E, the dialog UI57 shown in FIG. 47D, the dialog UI58 shown in FIG. 47E, or the dialog UI60 shown in FIG. 53D, which will be described later. In step ST232 shown in FIG. 38, when the selection of the link to the setting dialog for the expert meeting is not received (when "No"), the process waits.

In step ST234 shown in FIG. 38, the expert meeting terminal B15 of the medical facility B1 receives selection of a schedule by the doctor in charge H1a from the input unit 106X. The doctor in charge H1a checks a check box for selecting a candidate schedule for which the expert meeting is desired to be held from the input unit 106X. Then, the doctor in charge H1a selects each "set" icon option. When this is received by the expert meeting terminal B15 of the medical facility B1, the reception of the selection the schedule is performed.

In step ST235 shown in FIG. 38, the expert meeting terminal B15 of the medical facility B1 transmits information received in step ST234, to the integrated data management device A.

(2-4) Integrated Data Management Device Side

Next, a specific step of the schedule setting process of step ST41 shown in FIG. 20 will be described with reference to FIG. 39.

Figure 39:
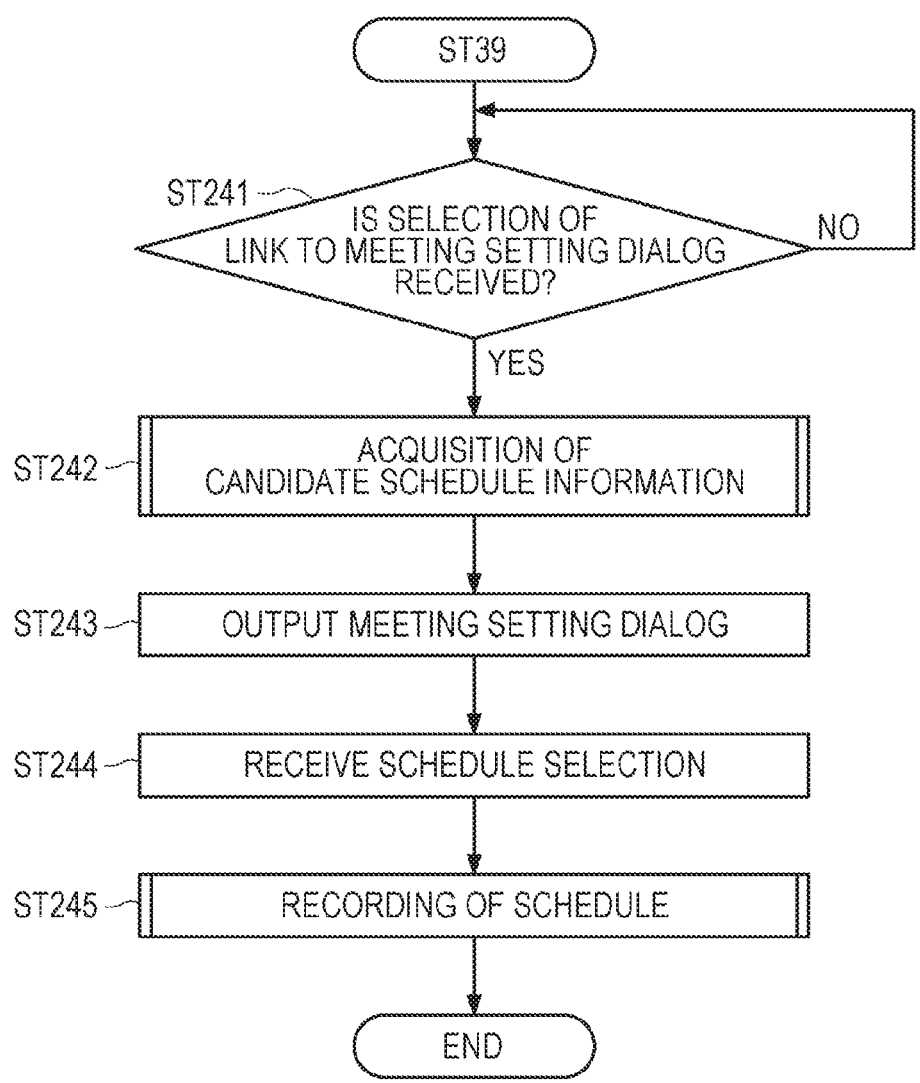
FIG. 39 shows a flowchart of a process for setting an expert meeting in the integrated data management device A.

In step ST241 of FIG. 39, the integrated data management device A determines whether or not selection of a link to the setting dialog for the expert meeting is received from a browser of the expert meeting terminal B15 of the medical facility B1. When the selection of the link is received from the expert meeting terminal B15 of the medical facility B1 (when step ST241 of FIG. 39 is "Yes"), the integrated data management device A proceeds to step ST242. Then, the integrated data management device A acquires a candidate schedule having a vacant slot from the meeting schedule database SDB. A variation of the processing in step ST242 will be described later. In step ST242, the control unit 100A of the integrated data management device A functions as the schedule update unit A20.

Next, the integrated data management device A proceeds to step ST243. Then, the integrated data management device A outputs an operation screen of, including a candidate schedule, the dialog UI51 shown in FIG. 3A and the dialog UI52 shown in FIG. 3B, and the dialog UI55 shown in FIG. 43D, the dialog UI56 shown in FIG. 43E, the dialog UI57 shown in FIG. 47D, the dialog UI58 shown in FIG. 47E, or the dialog UI60 shown in FIG. 53D, which will be described later, to the expert meeting terminal B15 of the medical facility B1. In step ST243, the control unit 100A of the integrated data management device A functions as the schedule output unit A21.

In step ST244 of FIG. 39, the integrated data management device A receives schedule information including the candidate schedule that is transmitted by the expert meeting terminal B15 of the medical facility B1 and selected by the doctor in charge H1a. In step ST245, the integrated data management device A records the schedule information in the meeting schedule database SDB. When the expert meeting is set, the integrated data management device A displays the "set" label in the "setting status" field of the test request list UI1 shown in FIG. 36. The schedule of the expert meeting set in the "holding date and time" field is displayed.

(3) Variation of Candidate Schedule Output Process

A variation of a candidate schedule acquisition process in step ST242 of FIG. 39 will be described.

(3-1) Pattern 1

With reference to FIGS. 3A to 3C and 39 to 42, one embodiment of the output process performed by the integrated data management device A will be described. The present embodiment is an example of outputting a candidate schedule by using the candidate schedule table MS in accordance with whether or not a mutation is detected in gene panel testing.

FIGS. 40A to 40C show an outline of the present embodiment. FIG. 40A shows a part of the master table M. In FIG. 40A, for patient ID: PA01, a mutation is "present" in the first attribute information. For patient ID: PA02, a mutation is "absent" in the first attribute information. FIG. 40B shows a time category table T. In the time category table T, in accordance with the first attribute information that is an outline of a test result, meeting time of 60 minutes (60 min) is assigned and "A" is assigned as the time category ID, to a row with the mutation "present". To a row with the mutation "absent", meeting time of 10 minutes (10 min) is assigned, and "B" is assigned as the time category ID.

The label "meeting time" in the time category table T shown in FIG. 40B corresponds to required time. The time category ID corresponds to a label indicating the required time. In the present embodiment, required time when a mutation is "present" corresponds to the first required time, and required time when a mutation is "absent" corresponds to the second required time.

In the present embodiment, the candidate schedule table MS shown in FIG. 35A is used as FIG. 40C.

In accordance with the first attribute information recorded in the master table M of FIG. 40A, the meeting time and the time category ID of the time category table T of FIG. 40B are assigned to each patient ID.

This processing will be described with reference to FIG. 41.

Figure 41:
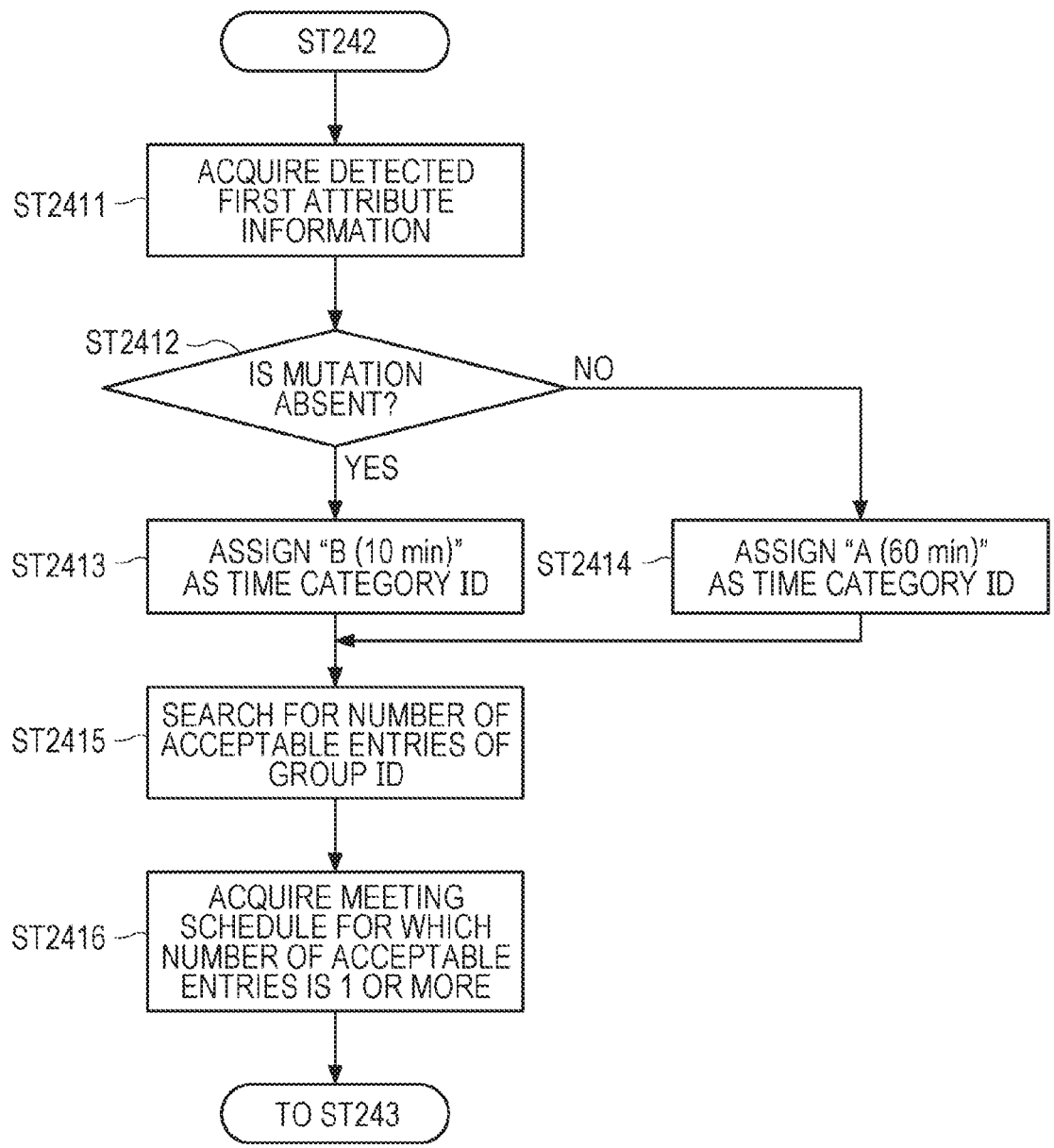
FIG. 41 shows a flowchart of pattern 1.

In step ST2411 of FIG. 41, the integrated data management device A acquires the first attribute information recorded in the master table M shown in FIG. 7 for each patient. In the next step ST2412, the integrated data management device A determines whether or not a mutation is absent. When it is determined that a mutation is absent (when "Yes") in step ST2412, as the time category ID, the label "B" shown in FIG. 40B is assigned and recorded as a label of the time category ID, to the "time category ID" field of the corresponding patient in the master table M shown in FIG. 7.

When it is determined that a mutation is not absent in step ST2412 of FIG. 41 (when "No"), as the time category ID, the integrated data management device A assigns and records the label "A" shown in FIG. 40B as a label of the time category ID, to the "time category ID" field of the corresponding patient in the master table M shown in FIG. 7.

Taking the patient ID: PA01 as an example, in step ST2415 of FIG. 41, the integrated data management device A refers to group ID: G01 corresponding to the patient ID: PA01 in the master table M shown in FIG. 7 and the time category ID "A" recorded in step ST2414 of FIG. 41. Subsequently, in the candidate schedule table MS shown in FIG. 40C, the integrated data management device A searches for the group ID: G01 referenced in the master table M shown in FIG. 7. Further, the integrated data management device A searches for a schedule for which the number of acceptable entries of the time category ID "A" is not "0" from a candidate slot of a meeting holding date and time corresponding to the group ID.

Taking the patient ID: PA02 as an example, in step ST2415 of FIG. 41, the integrated data management device A refers to group ID: G01 corresponding to the patient ID: PA02 in the master table M shown in FIG. 7 and the time category ID "B" recorded in step ST2413 of FIG. 41. Subsequently, in the candidate schedule table MS shown in FIG. 40C, the integrated data management device A searches for the group ID: G01 referenced in the master table M shown in FIG. 7. Further, the integrated data management device A searches for schedule information for which the number of acceptable entries of the time category ID "B" is "1" or more from a candidate slot of a meeting holding date and time corresponding to the group ID. The schedule information includes a holding date, a holding schedule time zone slot, a time category ID, and the like.

Subsequently, in step ST2416 of FIG. 41, the integrated data management device A acquires a meeting schedule for which the number of acceptable entries is "1 or more".

When each doctor in charge of a patient selects "unset label" of "setting status" of the test management list UI1 from the expert meeting terminal of each medical facility, the integrated data management device A outputs a candidate schedule included in the schedule information acquired in step ST2416 of FIG. 41 to the dialog UI51 shown in FIG. 3A or the dialog UI52 shown in FIG. 3B in accordance with a test result, in step ST243 shown in FIG. 39.

The dialog UI51 of FIG. 3A is provided with the candidate schedule display area UI511 as described above. The candidate schedule display area UI511 may display holding dates, time zone labels indicating candidate schedules represented by the meeting time "15:00 to 16:00" and "14:00 to 15:00" and the time category ID "A" according to a test result "mutation present". In the present embodiment, the label "A" indicating the required time is a label indicating that it is first required time in the present specification.

The dialog UI52 of FIG. 3B is provided with the candidate schedule display area UI521 as described above. The candidate schedule display area UI521 may display holding dates, time zone labels indicating candidate schedules represented by the meeting time "16:00 to 16:10", "16:10 to 16:20", and "16:20 to 16:30" and the time category ID "B" according to a test result "no mutation". In the present embodiment, the label "B" indicating the required time is a label indicating that it is the second required time in the present specification. Each doctor in charge of a patient selects a schedule for which an expert meeting is desired to be set from candidate schedules displayed in each dialog. Then, the doctor in charge selects the set icon UI513 or the set icon UI523. This operation causes the schedule set by each doctor in charge to be transmitted from the expert meeting terminal of each medical facility to the integrated data management device A.

In step ST245 shown in FIG. 39, the integrated data management device A receives, for example, schedule information set by each doctor in charge of a patient. Then, the integrated data management device A records the schedule information in the meeting schedule database SDB.

Once the schedule for each expert meeting is set, it is necessary to reduce, from the candidate schedule table MS shown in FIG. 40C, the number of acceptable entries corresponding to the candidate slot of the meeting holding date and time in which the candidate schedule set by each doctor in charge has been included.

Figure 42:
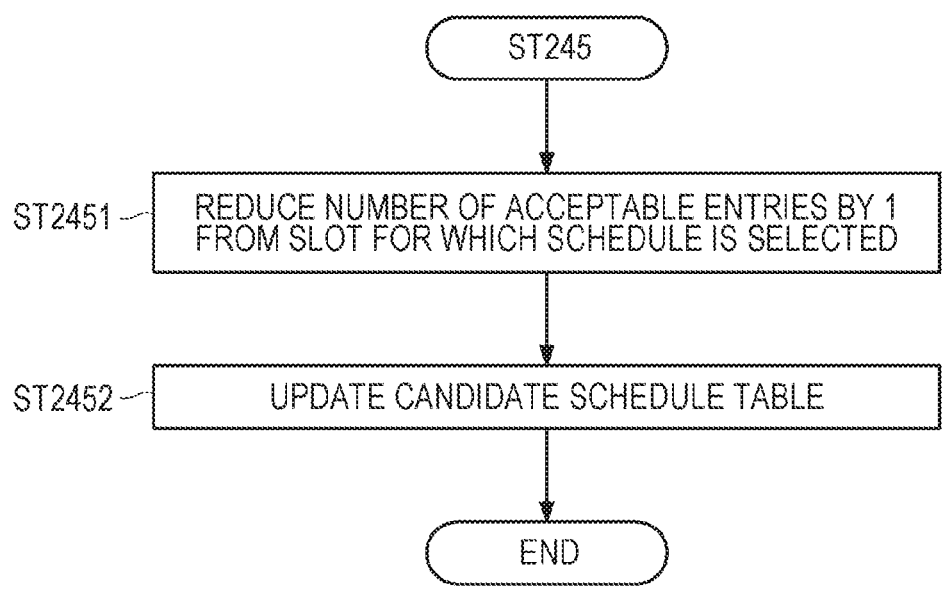
FIG. 42 shows an update process of the candidate schedule table MS.

In step ST2451 shown in FIG. 42, in each candidate schedule table MS shown in FIG. 40C, the integrated data management device A reduces the number by one from the number of acceptable entries corresponding to the candidate slot of the meeting holding date and time for which the doctor in charge has selected the schedule. In step ST2452 of FIG. 42, the integrated data management device A records a change content, to update the candidate schedule table MS.

(3-2) Pattern 2

With reference to FIGS. 43A to 43E to 46, and 39, one embodiment of the output process performed by the integrated data management device A will be described. The present embodiment is an example of outputting a candidate schedule by using the candidate schedule table MS2 in accordance with whether or not a mutation is detected in gene panel testing.

FIG. 43A shows a part of the master table M. In FIG. 43A, for patient ID: PA01, a mutation is "present" in the first attribute information. FIG. 43B shows the time category table T. The time category table T is the same as that in FIG. 40B. In the present embodiment, there is used the candidate schedule table MS2 shown in FIG. 43C corresponding to the candidate schedule table MS shown in FIG. 35B.

In accordance with the first attribute information recorded in the master table M of FIG. 43A, the meeting time and the time category ID of the time category table T of FIG. 43B are assigned to each patient ID.

This processing will be described with reference to FIG. 44.

In step ST2461 of FIG. 44, the integrated data management device A acquires the first attribute information recorded in the master table M shown in FIG. 7 for each patient. In step ST2462 in FIG. 44, the integrated data management device A determines whether or not there is a mutation. When it is determined that there is a mutation (when "Yes") in step ST2462 of FIG. 44, in step ST2463, as the time category ID, the label "A" shown in FIG. 43B is assigned and recorded as a label of the time category ID, to the "time category ID" field of the corresponding patient in the master table M shown in FIG. 7.

Next, the integrated data management device A proceeds to step ST2464 in FIG. 44. Then, the integrated data management device A refers to the candidate schedule table MS2 shown in FIG. 43C, based on a group ID corresponding to each patient of the master table M shown in FIG. 7, and based on the time category ID "A" recorded in step ST2463 of FIG. 44.

Subsequently, the integrated data management device A proceeds to step ST2465 in FIG. 44. The integrated data management device A searches for the group ID: G01 referenced in the master table M shown in FIG. 7, in the candidate schedule table MS2 shown in FIG. 43C. Then, the integrated data management device A acquires schedule information having vacant time of 60 minutes or more, from the candidate slots of the meeting holding date and time corresponding to the group ID.

When it is determined that there is no mutation in step (when "No") ST2462 of FIG. 44, in step ST2466, as the time category ID, the integrated data management device A assigns and records the label "B" shown in FIG. 43B as a label of the time category ID, to the "time category ID" field of the corresponding patient in the master table M shown in FIG. 7.

Next, the integrated data management device A proceeds to step ST2467 in FIG. 44. Then, the integrated data management device A refers to the candidate schedule table MS2 shown in FIG. 43C, based on a group ID corresponding to each patient of the master table M shown in FIG. 7, and based on the time category ID "B" recorded in step ST2466 of FIG. 44.

Subsequently, the integrated data management device A proceeds to step ST2468 in FIG. 44. The integrated data management device A searches for the group ID: G01 referenced in the master table M shown in FIG. 7, in the candidate schedule table MS2 shown in FIG. 43C. Then, the integrated data management device A acquires schedule information having vacant time of 10 minutes or more, from the candidate slots of the meeting holding date and time corresponding to the group ID.

When each doctor in charge of a patient selects "unset label" of "setting status" of the test management list UI1 from the expert meeting terminal of each medical facility, the integrated data management device A outputs a candidate schedule included in the schedule information acquired in step ST2465 of FIG. 44 to the dialog UI55 shown in FIG. 43D in accordance with a test result, in step ST243 shown in FIG. 39. Alternatively, the integrated data management device A outputs the candidate schedule included in the schedule information acquired in step ST2468 of FIG. 44 to the dialog UI56 shown in FIG. 43E.

The output of the candidate schedule may be outputted as the number of acceptable entries according to a meeting time corresponding to each time category ID based on vacant time.

Figure 45:
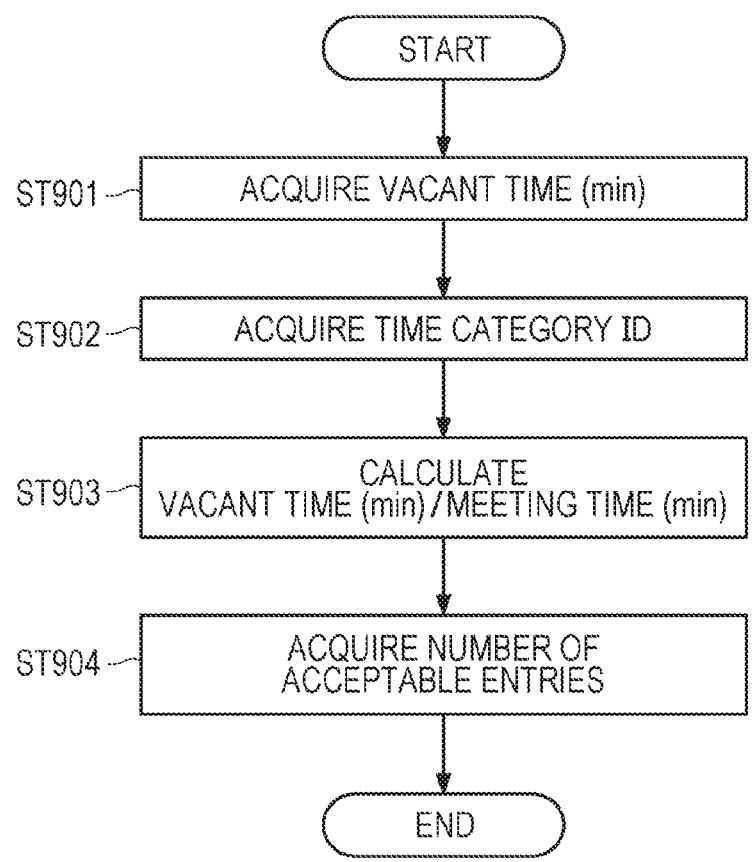
FIG. 45 shows a flowchart for calculating a number of acceptable entries based on vacant time.

FIG. 45 shows a process for acquiring the number of acceptable entries based on the vacant time.

In step ST901 shown in FIG. 45, the integrated data management device A acquires vacant time from the candidate schedule table MS2 shown in FIG. 43C.

In step ST902 shown in FIG. 45, the integrated data management device A acquires the time category ID recorded in step ST2463 or step ST2466 of FIG. 44 from the master table M shown in FIG. 7. Then, the integrated data management device A acquires the meeting time corresponding to the recorded time category ID from the time category table T of FIG. 43B.

The integrated data management device A proceeds to step ST903. Then, the integrated data management device A determines how many meetings that require meeting time corresponding to the time category ID can be accepted based on the vacant time. For example, in a case of 2019 Feb. 8 in FIG. 43C, the vacant time is 90 minutes. Therefore, when the first attribute information indicates mutation present, the vacant time 90 minutes is divided by the meeting time (60 minutes) corresponding to the time category ID "A", and a fraction after the decimal point is truncated, resulting in the integer "1". For example, in a case of 2019 Feb. 8 in FIG. 43C, the vacant time is 90 minutes. Therefore, when the first attribute information indicates that there is no mutation, the vacant time 90 minutes is divided by the meeting time (10 minutes) corresponding to the time category ID "B", and a fraction after the decimal point is truncated, resulting in the integer "11".

In step ST904 shown in FIG. 45, the integrated data management device A acquires the integer calculated in step ST903 as the number of acceptable entries.

The dialog UI55 shown in FIG. 43D includes a candidate schedule display area UI551, and a selection area UI552 for selection of a candidate date. The candidate schedule display area UI551 may display a holding date, and a label indicating the number of acceptable entries of the time category ID "A" as the meeting time corresponding to the test result "mutation present". In the present embodiment, the label "A" indicating the required time is a label indicating that it is the first required time in the present specification.

The dialog UI56 shown in FIG. 43E includes a candidate schedule display area UI561, and a selection area UI562 for selection of a candidate date. The candidate schedule display area UI561 may display a holding date, and a label indicating the number of acceptable entries of the time category ID "B" as the meeting time corresponding to the test result "no mutation". In the present embodiment, the label "B" indicating the required time is a label indicating that it is the second required time in the present specification.

Each doctor in charge of a patient selects a schedule for which an expert meeting is desired to be set from candidate schedules displayed in each dialog. The desired schedule is made by selecting a check box of the desired date in the selection area UI552 or the selection area UI562. After completing the selection in the selection area UI552 or the selection area UI562, each doctor in charge selects a set icon UI553 or a set icon UI563. This operation causes the schedule set by each doctor in charge to be transmitted from the expert meeting terminal of each medical facility to the integrated data management device A.

In step ST245 shown in FIG. 39, the integrated data management device A receives, for example, schedule information set by each doctor in charge of a patient. Then, the integrated data management device A records the schedule information in the meeting schedule database SDB.

Once the schedule for each expert meeting is set, it is necessary to reduce, from the candidate schedule table MS shown in FIG. 43C, vacant time and the like corresponding to the candidate slot of the meeting holding date and time in which the candidate schedule set by each doctor in charge has been included.

Figure 46:
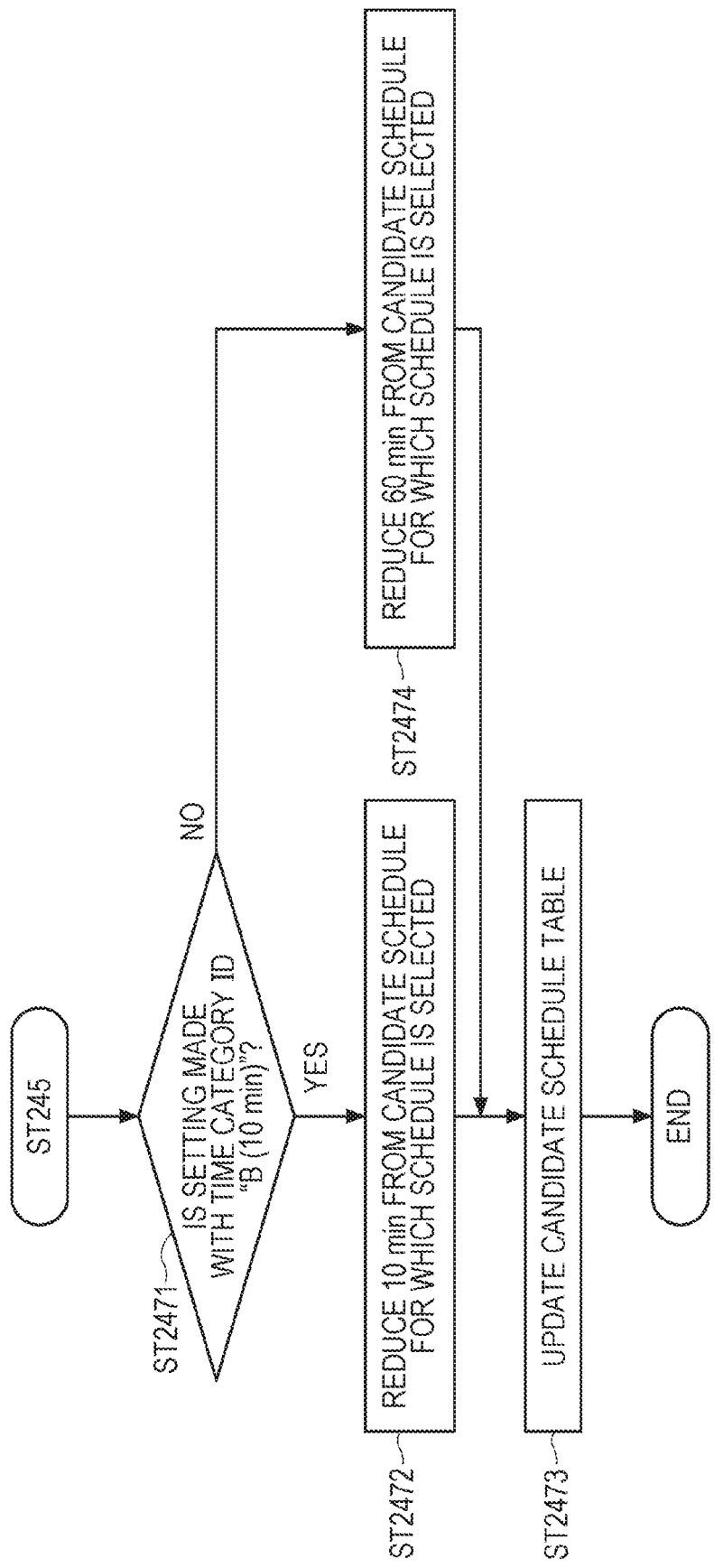
FIG. 46 shows an update process of the candidate schedule table MS2.

As shown in FIG. 46, in step ST2471, the integrated data management device A determines whether or not the schedule is set with the time category ID In a case of "Yes" in step ST2471 of FIG. 46, the integrated data management device A proceeds to step ST2472. Then, the integrated data management device A increases the number by 1 in the field of the setting status "B" of the candidate slot for the meeting holding date and time for which the schedule has been set, in the candidate schedule table MS2 shown in FIG. 43C. The integrated data management device A also reduces 10 minutes from the set time field and the vacant time field.

In a case of "No" in step ST2471 of FIG. 46, the integrated data management device A proceeds to step ST2474. Then, the integrated data management device A increases the number by 1 in the field of the setting status "A" of the candidate slot for the meeting holding date and time for which the schedule has been set, in the candidate schedule table MS2 shown in FIG. 43C. The integrated data management device A also reduces 60 minutes from the set time field and vacant time field.

In step ST2473 of FIG. 46, the integrated data management device A records a change content, to update the candidate schedule table MS2.

(3-3) Pattern 3

With reference to FIGS. 47A to 47E to 49, 45, and 39, one embodiment of the output process performed by the integrated data management device A will be described. The present embodiment is an example of outputting a candidate schedule in accordance with the number of mutations detected in gene panel testing.

FIG. 47A shows a part of the master table M. In FIG. 47A, for patient ID: PA01, a mutation is "present" and the number of mutations is "7" in the first attribute information. For patient ID: PA03, a mutation is "absent" and the number of mutations is "0" in the first attribute information. FIG. 47B shows a time category table T2. In the time category table T2, meeting time is set in accordance with the number of mutations, and a time category ID is recorded corresponding to each meeting time. For example, when the number of mutations is "1 to 5", the meeting time is "30 minutes", and "A1" is assigned as the time category ID. When the number of mutations is "6 to 10", the meeting time is "60 minutes", and "A2" is assigned as the time category ID. When there is no mutation, the number of mutations is "0", the meeting time is "10 minutes", and "B" is assigned as the time category ID. In the present embodiment, the meeting time corresponding to the time category IDs "A1" to "A4" in FIG. 47B is the first required time. The meeting time corresponding to the time category ID "B" is the second required time.

In the present embodiment, basically, the candidate schedule table MS2 shown in FIG. 35B is used. However, in a candidate schedule table MS3 shown in FIG. 47C, a setting status field is added corresponding to the time category IDs "A1" to "A4". In FIG. 47C, for convenience, "A2" and "B" alone are shown.

In the present embodiment, the meeting time and the time category ID in the time category table T2 in FIG. 47B are assigned to each patient ID in the master table M in FIG. 7, in accordance with the number of mutations recorded in the first attribute information in the master table M of FIG. 7.

This processing will be described with reference to FIG. 48.

Figure 48:
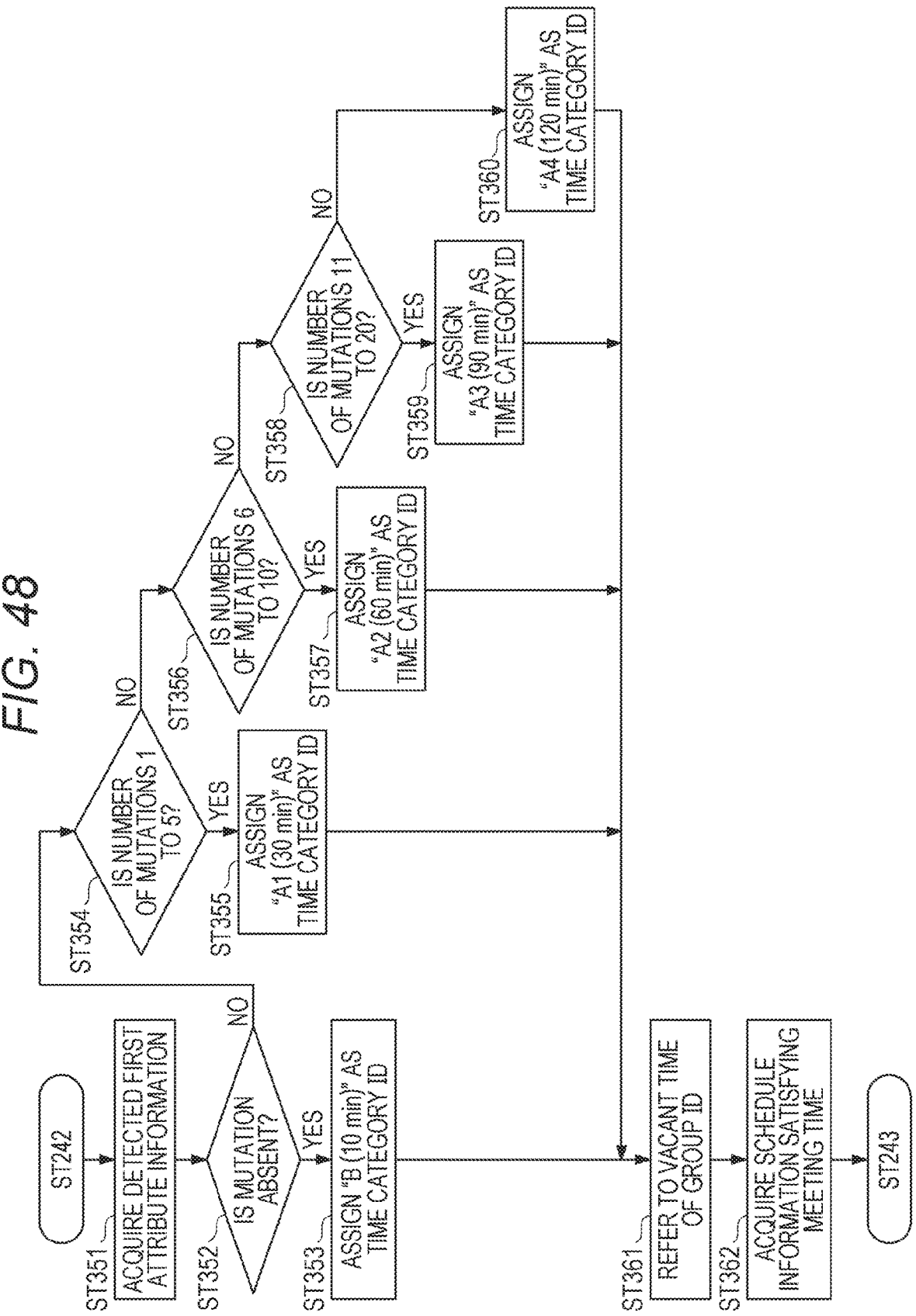
FIG. 48 shows a flowchart of pattern 3.

In step ST351 of FIG. 48, the integrated data management device A acquires the first attribute information recorded in the master table M shown in FIG. 7 for each patient. The acquired first attribute information includes the number of mutations.

In step ST352 in FIG. 48, the integrated data management device A determines whether or not a mutation is absent. When it is determined that a mutation is absent in step (when "Yes") ST352 of FIG. 48, in step ST353, as the time category ID, the label "B" shown in FIG. 48B is assigned and recorded as a label of the time category ID, to the "time category ID" field of the corresponding patient in the master table M shown in FIG. 7.

When it is determined in step ST352 of FIG. 48 that a mutation is present (when "No"), the integrated data management device A proceeds to step ST354 to determine whether the number of mutations is 1 to 5.

When the number of mutations is 1 to 5 (when "Yes") in step ST354 of FIG. 48, the integrated data management device A proceeds to step ST355. Then, the integrated data management device A assigns and records, as the time category ID, the label "A1" shown in FIG. 47B as a label of the time category ID, to the "time category ID" field of the corresponding patient in the master table M shown in FIG. 7.

When the number of mutations is not 1 to 5 (when "No") in step ST354 of FIG. 48, the integrated data management device A proceeds to step ST356 to determine whether the number of mutations is 6 to 10.

When the number of mutations is 6 to 10 (when "Yes") in step ST356 of FIG. 48, the integrated data management device A proceeds to step ST357. Then, the integrated data management device A assigns and records, as the time category ID, the label "A2" shown in FIG. 47B as a label of the time category ID, to the "time category ID" field of the corresponding patient in the master table M shown in FIG. 7.

When the number of mutations is not 6 to 10 (when "No") in step ST356 of FIG. 48, the integrated data management device A proceeds to step ST358 to determine whether the number of mutations is 11 to 20.

When the number of mutations is 11 to 20 (when "Yes") in step ST358 of FIG. 48, the integrated data management device A proceeds to step ST359. Then, the integrated data management device A assigns and records, as the time category ID, the label "A3" shown in FIG. 47B as a label of the time category ID, to the "time category ID" field of the corresponding patient in the master table M shown in FIG. 7.

When the number of mutations is not 11 to 20 (when "No") in step ST358 of FIG. 48, the integrated data management device A proceeds to step ST360. Then, the integrated data management device A assigns and records, as the time category ID, the label "A4" shown in FIG. 47B as a label of the time category ID, to the "time category ID" field of the corresponding patient in the master table M shown in FIG. 7.

When the integrated data management device A assigns each time category ID in step ST353, step ST355, step ST357, step ST359, and step ST360 of FIG. 48, the integrated data management device A proceeds to step ST361 in FIG. 48. Then, the integrated data management device A refers to the candidate schedule table MS3 shown in FIG. 47C on the basis of the group ID corresponding to each patient of the master table M shown in FIG. 7, and the time category ID "B" recorded in step ST353 of FIG. 48.

Subsequently, the integrated data management device A proceeds to step ST362 in FIG. 48. The integrated data management device A searches for the group ID: G01 referenced in the master table M shown in FIG. 7, in the candidate schedule table MS3 shown in FIG. 48C. Then, the integrated data management device A acquires schedule information satisfying the meeting time shown in FIG. 47B, from the candidate slots of the meeting holding date and time corresponding to the group ID.

When each doctor in charge of a patient selects "unset label" of "setting status" of the test management list UI1 from the expert meeting terminal of each medical facility, the integrated data management device A outputs a candidate schedule included in the schedule information acquired in step ST362 of FIG. 48, to the dialog UI57 shown in FIG. 47D in accordance with a test result, in step ST243 shown in FIG. 39. Alternatively, the integrated data management device A outputs the candidate schedule included in the schedule information acquired in step ST362 of FIG. 48 to the dialog UI58 shown in FIG. 47E.

The output of the candidate schedule may be outputted as the number of acceptable entries according to a meeting time corresponding to each time category ID based on vacant time.

The process for acquiring the number of acceptable entries based on the vacant time is similar to steps ST901 to ST904 shown in FIG. 45.

The dialog UI57 shown in FIG. 47D is outputted according to the time category ID shown in FIG. 47B. FIG. 47D shows a case where the time category ID is "A2". The dialog UI57 in FIG. 47D includes a candidate schedule display area UI571, and a selection area UI572 for selection of a candidate date. The candidate schedule display area UI571 may display a holding date, and a label indicating the number of acceptable entries of the time category ID "A2" as the meeting time corresponding to the test result "mutation present". In the present embodiment, the label "A2" indicating the required time is a label indicating that it is the first required time in the present specification.

The dialog UI58 in FIG. 43E includes a candidate schedule display area UI581, and a selection area UI582 for selection of a candidate date. The candidate schedule display area UI581 may display a holding date, and a label indicating the number of acceptable entries of the time category ID "B" as the meeting time corresponding to the test result "no mutation". In the present embodiment, the label "B" indicating the required time is a label indicating that it is the second required time in the present specification.

The method for each doctor in charge of a patient to set a desired schedule from each dialog is similar to pattern 2. The schedule set by each doctor in charge from the expert meeting terminal of each medical facility is transmitted to the integrated data management device A.

In step ST245 shown in FIG. 39, the integrated data management device A receives, for example, schedule information set by each doctor in charge of a patient. Then, the integrated data management device A records the schedule information in the meeting schedule database SDB.

Once the schedule for each expert meeting is set, it is necessary to reduce, from the candidate schedule table MS shown in FIG. 47C, vacant time and the like corresponding to the candidate slot of the meeting holding date and time in which the candidate schedule set by each doctor in charge has been included.

Figure 49:
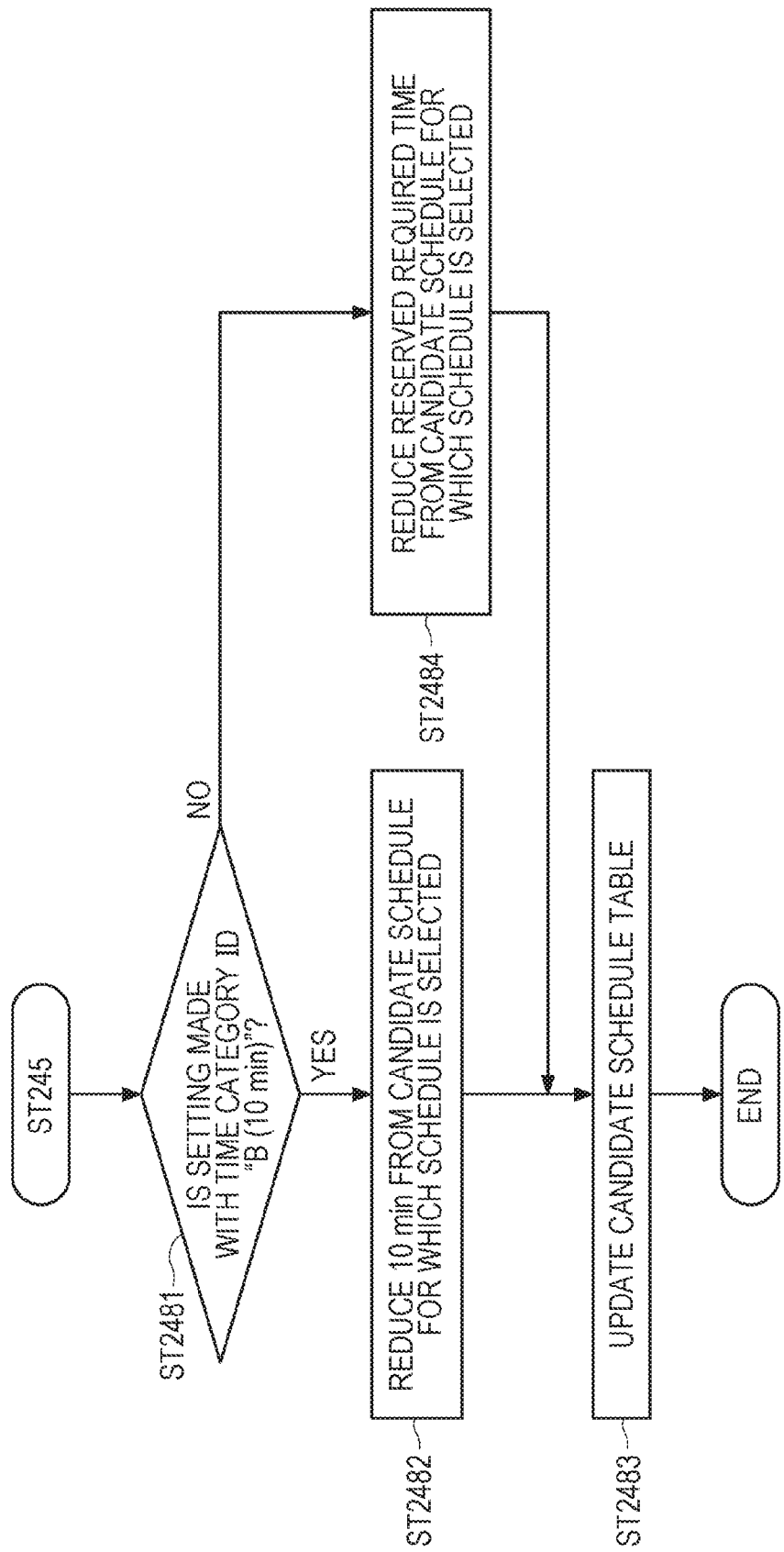
FIG. 49 shows an update process of the candidate schedule table MS3.

As shown in FIG. 49, in step ST2481, the integrated data management device A determines whether or not the schedule is set with the time category ID "B".

In a case of "Yes" in step ST2481 of FIG. 49, the integrated data management device A proceeds to step ST2482. Then, the integrated data management device A increases the number by 1 in the field of the setting status "B" of the candidate slot for the meeting holding date and time for which the schedule has been set, in the candidate schedule table MS3 shown in FIG. 47C. The integrated data management device A also reduces 10 minutes from the set time field and the vacant time field.

In a case of "No" in step ST2481 of FIG. 49, the integrated data management device A proceeds to step ST2484. Then, the integrated data management device A increases the number by 1 in the field corresponding to the time category ID for which the meeting is set, in "A1" to "A4" of the setting status of the candidate slot of the meeting holding date and time for which the schedule is set, in the candidate schedule table MS3 shown in FIG. 47C. The integrated data management device A also reduces the required time corresponding to the time category ID for which the meeting is set, from the set time field and the vacant time field.

In step ST2483 of FIG. 49, the integrated data management device A records a change content, to update the candidate schedule table MS3.

(3-4) Pattern 4

With reference to FIGS. 50A to 50C to 52, 47A to 47E, 45, 39, and 49, one embodiment of the output process performed by the integrated data management device A will be described. The present embodiment is an example of outputting a candidate schedule in accordance with a mutation type detected in gene panel testing.

FIG. 50A shows a part of the master table M. In FIG. 50A, for patient ID: PA01, a mutation is "present" in the first attribute information, and a mutation type is "actionable mutation" and the number of mutations is "6" in the second attribute information. For patient ID: PA03, a mutation is "present" in the first attribute information, and a mutation type is "actionable mutation" and "germline mutation", and the numbers of mutations are "5" and "1", respectively, in the second attribute information. FIG. 50B shows the time category table T2. The time category table T2 is similar to that of FIG. 47B. In the present embodiment, the meeting time corresponding to the time category IDs "A1" to "A4" in FIG. 50B may be the first required time. The meeting time corresponding to the time category ID "B" is the second required time.

In the present embodiment, the candidate schedule table MS3 shown in FIG. 47C is used. FIG. 50C shows an additional time category table AD as an example for adding meeting time. The additional time category table AD is provided with a field indicating the presence or absence of a germline mutation, a field indicating additional time, and a field indicating an additional time ID for identification of a category of the additional time. For example, when the germline mutation is "present", "C" is assigned as the additional time ID, and the additional time of 15 minutes is assigned. When the germline mutation is "absent", "D" is assigned as the additional time ID, and the additional time is not assigned. In the present embodiment, when additional time is assigned, time obtained by adding the additional time corresponding to the additional time ID "C" to the meeting time corresponding to the time category IDs "A1" to "A4" in FIG. 50B may be the first required time.

In the present embodiment, the meeting time and the time category ID in the time category table T2 in FIG. 50B are assigned to each patient ID in the master table M in FIG. 7, in accordance with the number of mutations recorded in the second attribute information in the master table M of FIG. 7. The additional time ID shown in FIG. 50C is assigned to each patient ID in the master table M of FIG. 7, in accordance with the mutation type recorded in the second attribute information in the master table M of FIG. 7.

This processing will be described with reference to FIG. 51.

Figure 51:
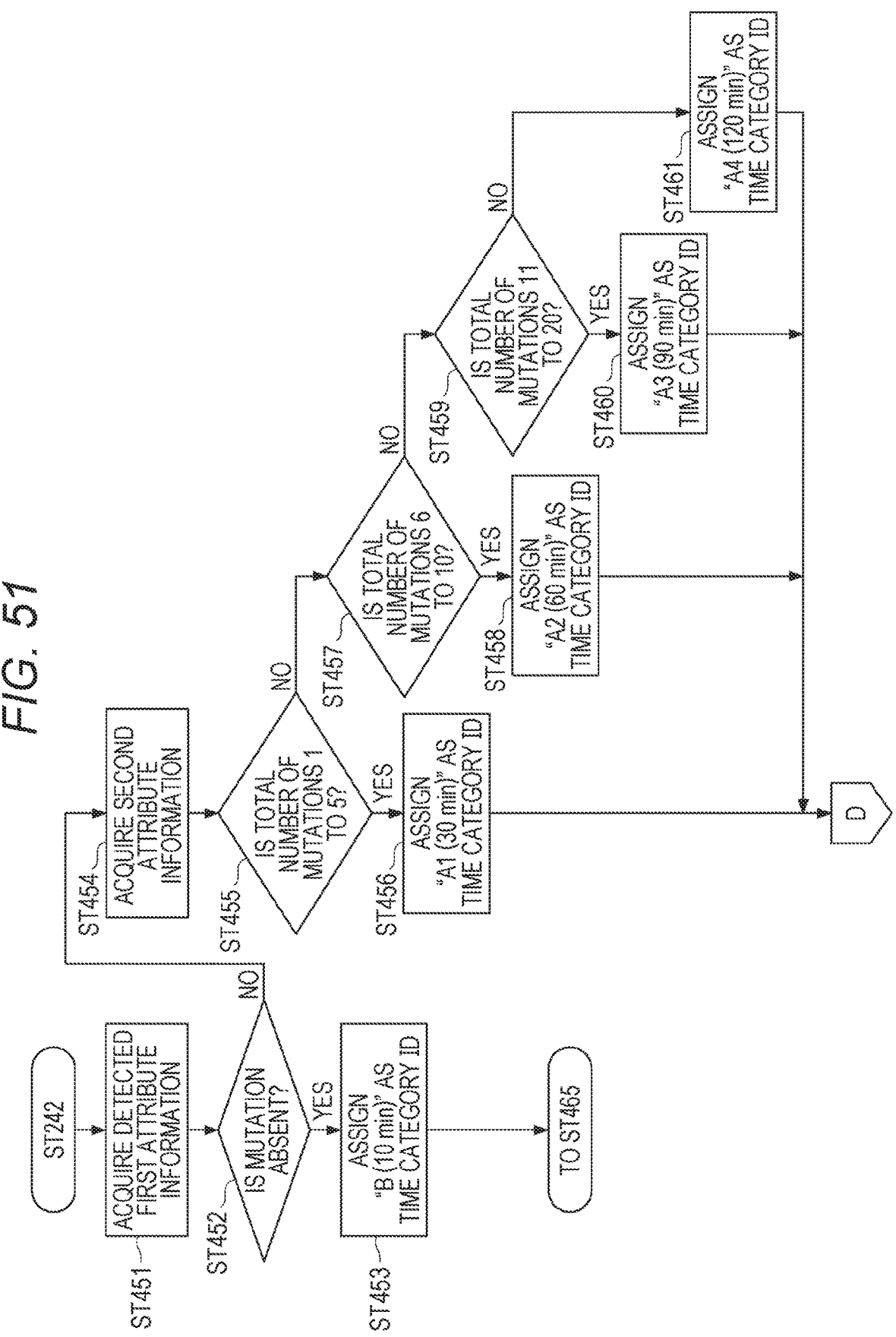
FIG. 51 shows a first half of a flowchart for pattern 4.

In step ST451 of FIG. 51, the integrated data management device A acquires the first attribute information recorded in the master table M shown in FIG. 7 for each patient.

In step ST452 in FIG. 51, the integrated data management device A determines whether or not a mutation is absent. When it is determined that a mutation is absent (when "Yes") in step ST452 of FIG. 51, in step ST453, as the time category ID, the label "B" shown in FIG. 51B is assigned and recorded as a label of the time category ID, to the "time category ID" field of the corresponding patient in the master table M shown in FIG. 7.

When it is determined in step ST452 of FIG. 51 that a mutation is not absent (when "No"), the integrated data management device A proceeds to step ST454. Then, the integrated data management device A acquires the second attribute information.

The integrated data management device A proceeds to step ST455, to determine whether a total number of mutations included in the second attribute information is 1 to 5.

When the total number of mutations is 1 to 5 (when "Yes") in step ST455 of FIG. 51, the integrated data management device A proceeds to step ST456. Then, the integrated data management device A assigns and records, as the time category ID, the label "A1" shown in FIG. 50B as a label of the time category ID, to the "time category ID" field of the corresponding patient in the master table M shown in FIG. 7.

When the total number of mutations is not 1 to 5 (when "No") in step ST455 of FIG. 51, the integrated data management device A proceeds to step ST457. Then, the integrated data management device A determines whether the total number of mutations is 6 to 10.

When the total number of mutations is 6 to 10 (when "Yes") in step ST457 of FIG. 51, the integrated data management device A proceeds to step ST458. Then, the integrated data management device A assigns and records, as the time category ID, the label "A2" shown in FIG. 50B as a label of the time category ID, to the "time category ID" field of the corresponding patient in the master table M shown in FIG. 7.

When the total number of mutations is not 6 to 10 (when "No") in step ST457 of FIG. 51, the integrated data management device A proceeds to step ST459. Then, the integrated data management device A determines whether the total number of mutations is 11 to 20.

When the number of mutations is 11 to 20 (when "Yes") in step ST459 of FIG. 51, the integrated data management device A proceeds to step ST460. Then, the integrated data management device A assigns and records, as the time category ID, the label "A3" shown in FIG. 50B as a label of the time category ID, to the "time category ID" field of the corresponding patient in the master table M shown in FIG. 7.

When the total number of mutations is not 11 to 20 (when "No") in step ST459 of FIG. 51, the integrated data management device A proceeds to step ST461. Then, the integrated data management device A assigns and records, as the time category ID, the label "A4" shown in FIG. 50B as a label of the time category ID, to the "time category ID" field of the corresponding patient in the master table M shown in FIG. 7.

Figure 52:
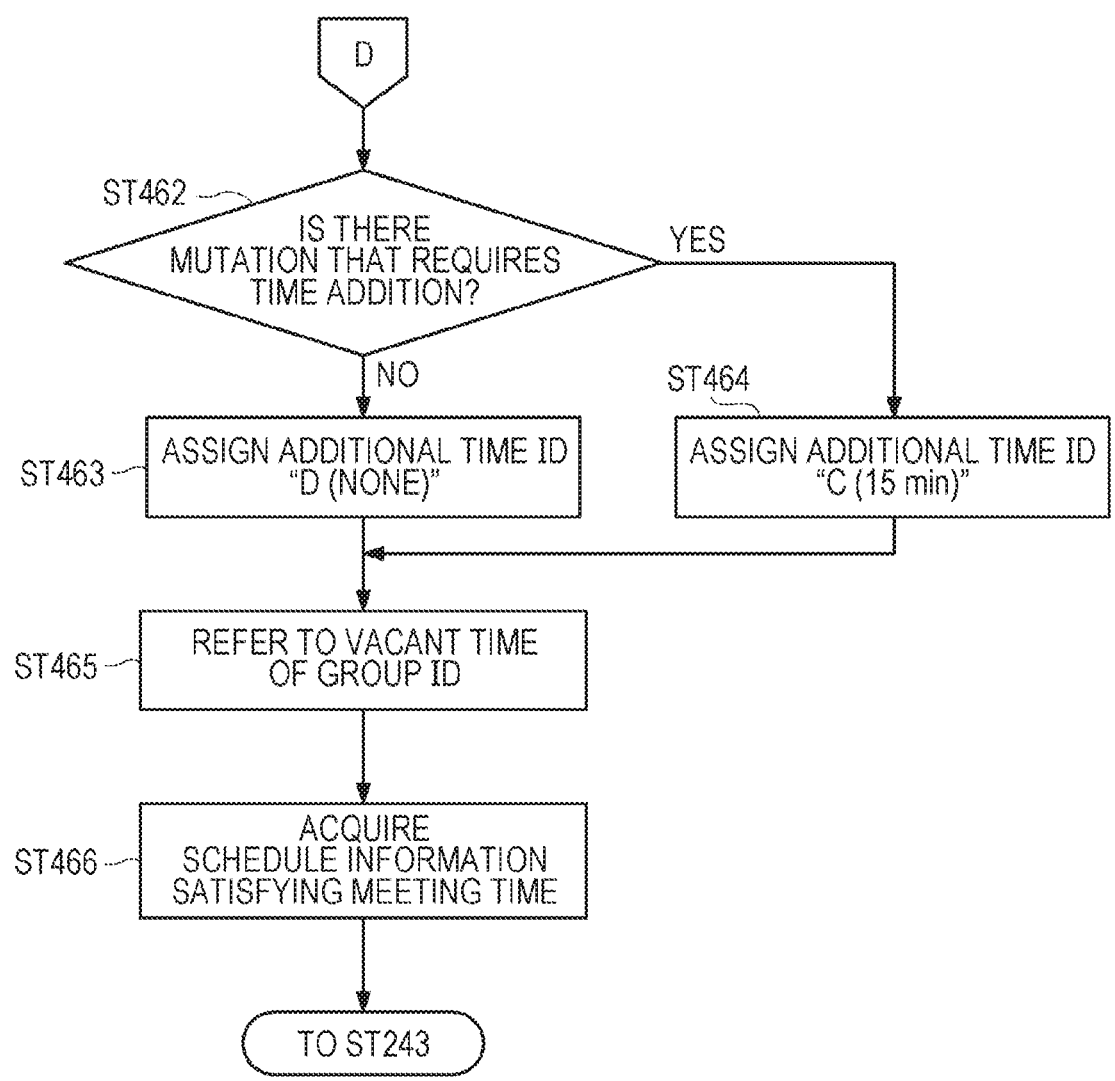
FIG. 52 shows a latter half of the flowchart for pattern 4.

When the integrated data management device A assigns each time category ID in step ST456, step ST458, step ST460, and step ST461, the integrated data management device A proceeds to step ST462 in FIG. 52. Steps from step ST462 are for adding the additional time.

As shown in FIG. 50A, the number of mutations detected by the gene panel testing is the same "6" in the patient ID: PA01 and the patient ID: PA03, but the mutation types are different. For example, the patient ID: PA03 includes a germline mutation, which may increase the required time for the meeting. Therefore, it is desirable to add in advance the required time for the meeting more than that of the patient ID: PA01.

In step ST462 of FIG. 52, the integrated data management device A determines whether or not it is necessary to add the meeting time, based on the mutation type of the second attribute information acquired in step ST454 of FIG. 51. A description is given here with "germline mutation" as a mutation that requires the additional meeting time.

In step ST462 of FIG. 52, when it is determined that there is no mutation (germline mutation) that requires the additional meeting time (when "No"), the integrated data management device A proceeds to step ST463, to assign the additional time ID "D".

In step ST462 of FIG. 52, when it is determined that there is a mutation (germline mutation) that requires the additional meeting time (when "Yes"), the integrated data management device A proceeds to step ST464, to assign the additional time ID "C".

FIGS. 53A to 53D show an example of acquiring schedule information from the candidate schedule table MS3 on the basis of FIG. 50B and FIG. 50C, and outputting an operation screen that enables schedule setting of the expert meeting. FIG. 53A corresponds to FIG. 50B, and FIG. 53B corresponds to FIG. 50C. FIG. 53C shows the candidate schedule table MS3. FIG. 53D shows an example of the dialog UI60 that is for schedule setting of an expert meeting.

The integrated data management device A proceeds to step ST465 after step ST453 of FIG. 51, and step ST463 or step ST464 of FIG. 52. Then, the integrated data management device A refers to the candidate schedule table MS3 shown in FIG. 53C, based on a group ID corresponding to each patient of the master table M shown in FIG. 7, and based on the time category ID recorded in step ST453, step ST456, step ST458, step ST460, or step ST461 of FIG. 51. When the additional time ID "C" is assigned in step ST464, the additional time ID "C" is also given to refer to the candidate schedule table MS3 shown in FIG. 53C.

Subsequently, the integrated data management device A proceeds to step ST466 in FIG. 52. The integrated data management device A searches for the group ID: G01 referenced in the master table M shown in FIG. 7, in the candidate schedule table MS3 shown in FIG. 53C. Then, from a candidate slot of a meeting holding date and time corresponding to the group ID, the integrated data management device A acquires schedule information satisfying the meeting time shown in FIG. 53A, or schedule information satisfying meeting time obtained by adding the additional time shown in FIG. 53B to the meeting time shown in FIG. 53A.

When each doctor in charge of a patient selects "unset label" of "setting status" of the test management list UI1 from the expert meeting terminal of each medical facility, the integrated data management device A outputs a candidate schedule included in the schedule information acquired in step ST466 of FIG. 52, to the dialog UI60 shown in FIG. 53D in accordance with a test result, in step ST243 shown in FIG. 39. The dialog outputted based on the time category ID "B" assigned in step ST453 of FIG. 51 is similar to the dialog UI58 shown in FIG. 47E. Therefore the description of the dialog UI58 shown in FIG. 47E is cited here.

The output of the candidate schedule may be outputted as the number of acceptable entries according to a meeting time corresponding to each time category ID based on vacant time.

Figure 54:
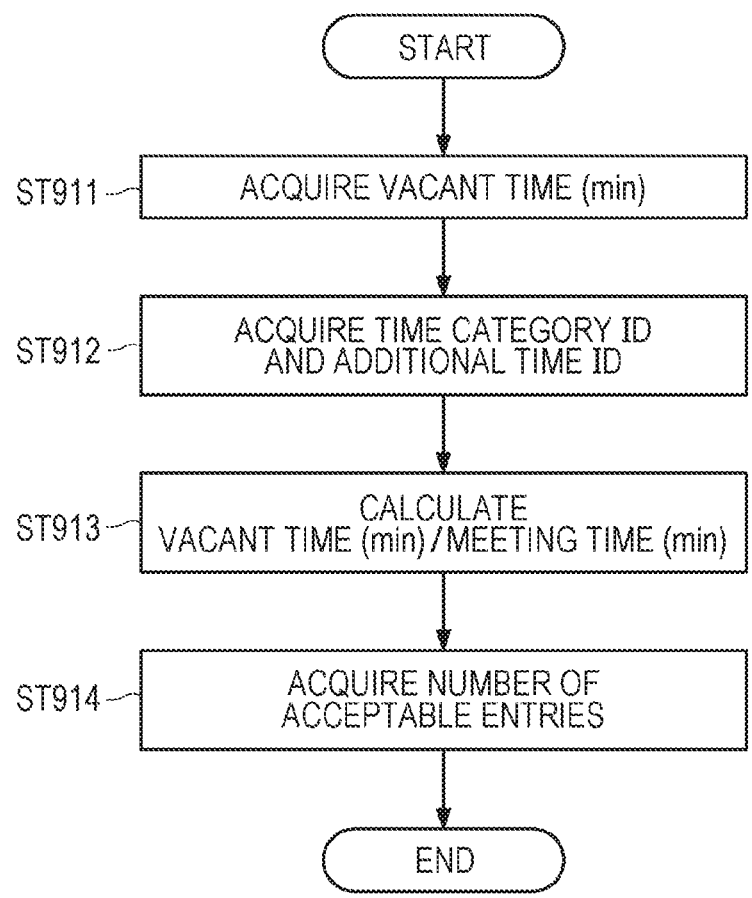
FIG. 54 shows a flowchart for calculating a number of acceptable entries based on vacant time.

FIG. 54 shows a process for acquiring the number of acceptable entries based on the vacant time.

In step ST911 shown in FIG. 54, the integrated data management device A acquires vacant time from the candidate schedule table MS3 shown in FIG. 53C.

In step ST912 shown in FIG. 54, the integrated data management device A acquires the time category ID recorded in step ST458, step ST460, or step ST461 of FIG. 51 from the master table M shown in FIG. 7, and the additional time ID acquired in step ST464 of FIG. 52. Then, the integrated data management device A acquires the meeting time corresponding to the recorded time category ID and additional time ID, from the time category table T2 of FIG. 53A and the additional time category table AD of FIG. 53B.

The integrated data management device A proceeds to step ST913. Then, integrated data management device A calculates how many meetings can be accepted that require meeting time corresponding to a total time of the time category ID and the additional time ID, based on the vacant time. The number of acceptable entries can be calculated by dividing the vacant time acquired in step ST911 of FIG. 54 by the total of the meeting time corresponding to the time category ID and the additional time ID, and truncating a fraction after the decimal point. In the example of FIGS. 53A to 53D, the patient ID: PA03 shown in FIG. 50A has the time category ID of "A2" shown in FIG. 53A and an additional time ID of "C" shown in FIG. 53B. Therefore, the meeting required time to examine the patient ID: PA03 is 75 minutes of "A2"+"C". Since the vacant time on 2019 Feb. 8 of the group ID: G01 shown in FIG. 53C is 90 minutes, the integer calculated in step ST913 of FIG. 54 is "1".

In step ST914 shown in FIG. 54, the integrated data management device A acquires the integer calculated in step ST913 as the number of acceptable entries.

The dialog UI60 shown in FIG. 53D is outputted according to the time category ID shown in FIG. 53A and the additional time ID shown in FIG. 53B. FIG. 53D shows a case where the time category ID is "A2" and the additional time ID is "C". The dialog UI60 in FIG. 53D includes a candidate schedule display area UI601, and a selection area UI602 for selection of a candidate date. The candidate schedule display area UI601 may display a holding date, and a label indicating the number of acceptable entries for meeting time of both the time category ID "A2" and the additional time ID "C", as the meeting time according to the test result "mutation present".

The method for each doctor in charge of a patient to set a desired schedule from each dialog is similar to pattern 2. The schedule set by each doctor in charge from the expert meeting terminal of each medical facility is transmitted to the integrated data management device A.

In step ST245 shown in FIG. 39, the integrated data management device A receives, for example, schedule information set by each doctor in charge of a patient. Then, the integrated data management device A records the schedule information in the meeting schedule database SDB.

Once the schedule for each expert meeting is set, it is necessary to reduce, from the candidate schedule table MS3 shown in FIG. 53C, vacant time and the like corresponding to the candidate slot of the meeting holding date and time in which the candidate schedule set by each doctor in charge has been included. This process is similar to the process shown in FIG. 49.

(4) Schedule Rearrangement Process

For the meeting schedule that has been set based on the vacant time of the candidate slot of the meeting holding date and time shown in (3-2) to (3-4) above, an order of holding may be rearranged within the same holding date in accordance with the required time for the set meeting, priority, and the like. Also when the set meeting is canceled, the order of holding of the meeting can be changed. According to the present embodiment, the order of holding can be adjusted within the same scheduled holding date.

(4-1) Adjustment Pattern 1

Figures 55A, 55B, 55C:
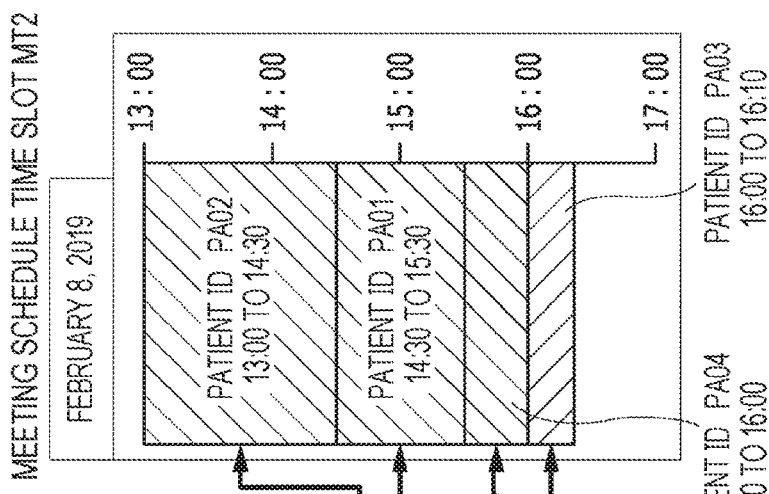
FIGS. 55A to 55C show an outline of adjustment pattern 1 in a schedule rearrangement process.

With reference to FIGS. 55A to 55C and 56, one embodiment for adjusting an order of holding meetings will be described. FIG. 55A shows a part of the master table M shown in FIG. 7 in a case where meeting time varies depending on the number of mutations of pattern 3 shown in (3-3) above. The second attribute information with different numbers of mutations is recorded for a plurality of patients. FIG. 55B shows the time category table T. An example of pattern 3 shown in (3-3) above is shown here, but the present embodiment can also be realized with pattern 4 shown in (3-4) above. For convenience, pattern 3 shown in (3-3) above is taken as an example.

FIG. 55C shows a meeting schedule time slot MT2 stored in the meeting schedule database SDB. The meeting schedule time slot MT2 stores a time zone for holding a meeting associated with a patient ID. When a setting of the expert meeting is recorded in step ST245 shown in FIG. 39, for example, each patient ID and the first required time or the second required time corresponding to each patient ID are stored in a candidate slot of a meeting holding date and time of the meeting schedule time slot MT2. The integrated data management device A performs the processing shown in FIG. 56, for example, one week before the holding date of the meeting, to adjust the order of holding within the same meeting holding date in accordance with required time for a meeting of each patient. This processing may be automatically performed by the integrated data management device A, a predetermined number of days before the holding date of the meeting. Alternatively, a staff of an expert meeting bureau may perform this processing through input from the input unit 106Z of the bureau expert meeting terminal SP15, if necessary.

Figure 56:
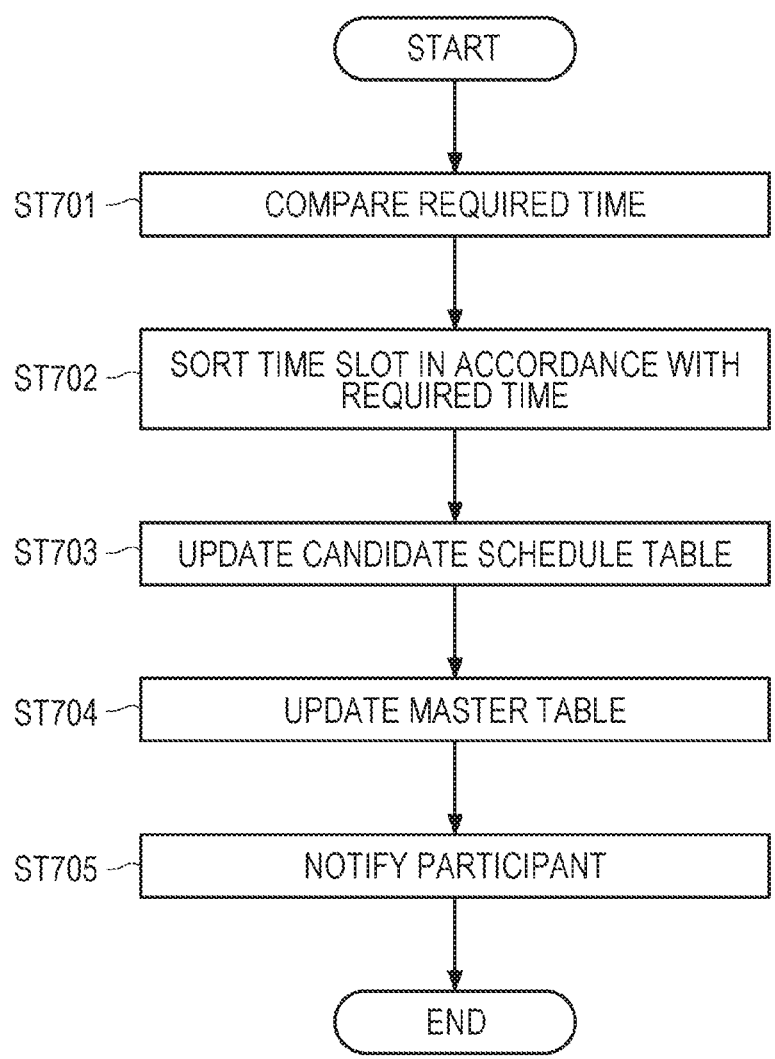
FIG. 56 is a flowchart of adjustment pattern 1.

In step ST701 of FIG. 56, the integrated data management device A compares required time for a meeting of each patient within the same meeting holding date.

In step ST702 of FIG. 56, the integrated data management device A sorts the meetings so that the meetings are held in order of longer required time, for example.

The integrated data management device A updates the meeting schedule time slot MT2 in step ST703 of FIG. 56. Then, the integrated data management device A updates the "holding date and time" field of the meeting of each patient in the master table M shown in FIG. 7 in step ST704.

In step ST705 of FIG. 56, the integrated data management device A notifies a participant in the expert meeting corresponding to each patient, of the schedule update. This notification is made to each participant by mail or the like, with, as a trigger, the update of the meeting schedule time slot MT2 in step ST703 or the update of the master table M in step ST704, for example.

(4-2) Adjustment Pattern 2

In the present embodiment, an order of holding expert meetings is adjusted in accordance with priority of a patient.

Figure 57:
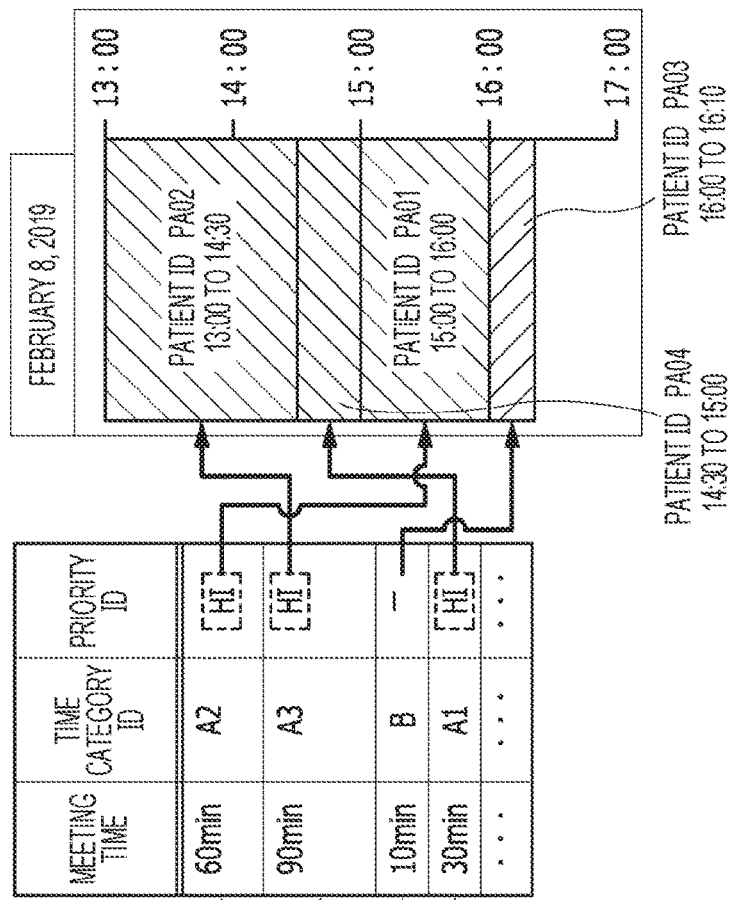
FIG. 57A shows a part of the master table M.
FIG. 57B shows meeting time, a time category ID, and a priority ID.
FIG. 57C shows a meeting schedule time slot MT3.

With reference to FIGS. 57A to 57C and 58, one embodiment for adjusting an order of holding meetings will be described. FIG. 57A shows a part of the master table M shown in FIG. 7 in a case where meeting time varies depending on the number of mutations of pattern 3 shown in (3-3) above. The second attribute information with different numbers of mutations is recorded for a plurality of patients. FIG. 57B shows meeting time set for each patient in accordance with the number of mutations, a time category ID, and a priority ID indicating priority. In a case of a patient with high priority for holding the expert meeting, for example, in a case where a result detected in gene panel testing is "actionable mutation", a label "HI" indicating high priority is given. An example of pattern 3 shown in (3-3) above is shown here, but the present embodiment can also be realized with pattern 4 shown in (3-4) above. For convenience, pattern 3 shown in (3-3) above is taken as an example.

FIG. 57C shows a meeting schedule time slot MT3 stored in the meeting schedule database SDB. The meeting schedule time slot MT3 stores a time zone for holding a meeting associated with a patient ID. When a setting of the expert meeting is recorded in step ST245 shown in FIG. 39, for example, each patient ID, the first required time or the second required time corresponding to each patient ID, and the priority ID are stored in a candidate slot for the meeting holding date and time in the meeting schedule time slot MT3. The integrated data management device A performs the processing shown in FIG. 58, for example, one week before the holding date of the meeting, to adjust the order of holding within the same meeting holding date in accordance with required time for a meeting of each patient. This processing may be automatically performed by the integrated data management device A, a predetermined number of days before the holding date of the meeting. Alternatively, a staff of an expert meeting bureau may perform this processing through input from the input unit 106Z of the bureau expert meeting terminal SP15, if necessary.

Figure 58:
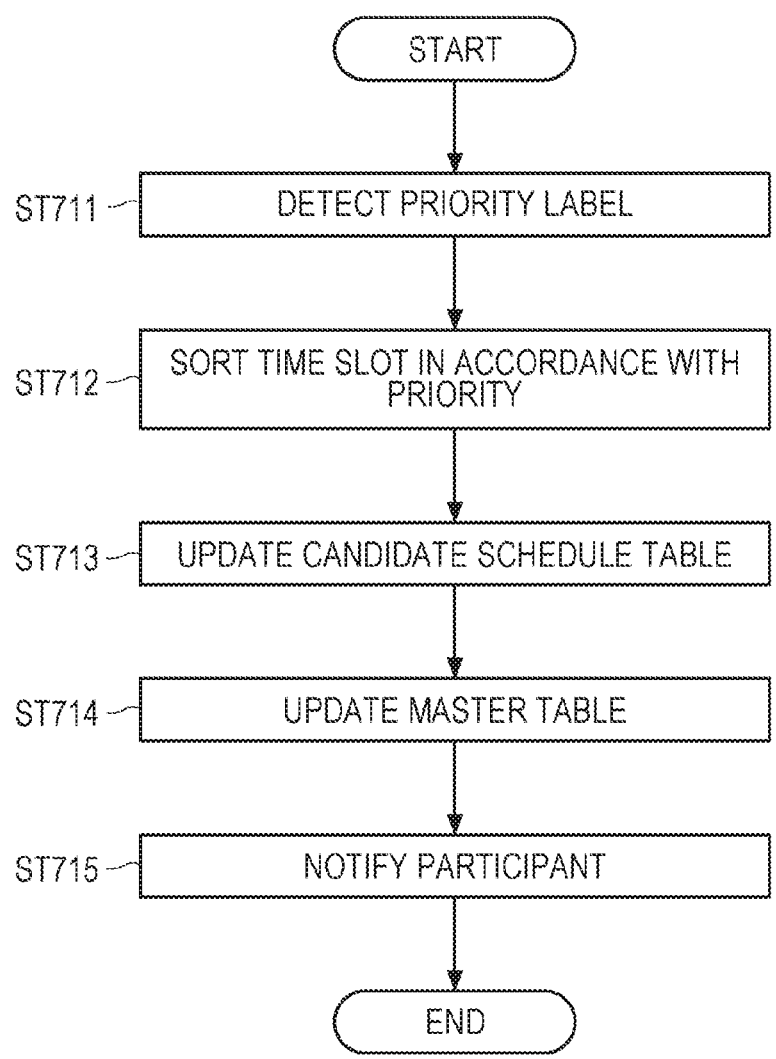
FIG. 58 shows a flowchart of adjustment pattern 2.

In step ST711 of FIG. 58, the integrated data management device A detects whether each patient has a label indicating priority within the same meeting holding date.

In step ST712 of FIG. 58, the integrated data management device A performs sorting, for example, so that the meeting holding time of the patient having the label indicating priority is earlier.

The integrated data management device A updates the meeting schedule time slot MT3 in step ST713 of FIG. 58. Then, the integrated data management device A updates the "holding date and time" field of the meeting of each patient in the master table M shown in FIG. 7 in step ST714.

In step ST715 of FIG. 58, the integrated data management device A notifies a participant in the expert meeting corresponding to each patient, of the schedule update. This notification is made to each participant by mail or the like, with, as a trigger, the update of the meeting schedule time slot MT3 in step ST713 or the update of the master table M in step ST714, for example.

When the integrated data management device A detects a label "HI" indicating priority in step ST711 of FIG. 58, the integrated data management device A may search as to whether there is vacant time in a candidate slot of the meeting holding date and time earlier than the meeting holding date and time set for the patient with "HI". For example, when there is vacant time due to cancellation and the like in a candidate slot of an early meeting holding date and time at which an expert meeting has been set earlier, and the vacant time satisfies the required time for the meeting of the patient with "HI", the schedule of the meeting may be changed, for example, by setting the meeting of the patient with "HI" in the vacant time. In this case, the integrated data management device A displays a screen for accepting a change, to accept the schedule change.

(5) Link to Quality Information

The integrated data management device A may output quality information to the test request list UI1 as shown in FIG. 59, in the test request list output process of step ST43 shown in FIG. 20. When no mutation is detected in gene panel testing, this quality information needs to be evaluated at the expert meeting, as to whether or not the determination of no somatic mutation in step ST208 shown in FIG. 25, or the determination of no germline mutation in step ST307 shown in FIG. 26 has been appropriate, after considering information regarding sample quality such as whether a nucleic acid has been properly obtained from a sample, or information regarding test quality such as whether there has been no problem in reaction in sequencing. A display example of the graphical user interface UI shown in FIG. 59 is useful for examining suitability of the sample and the test at the expert meeting.

Figure 60:
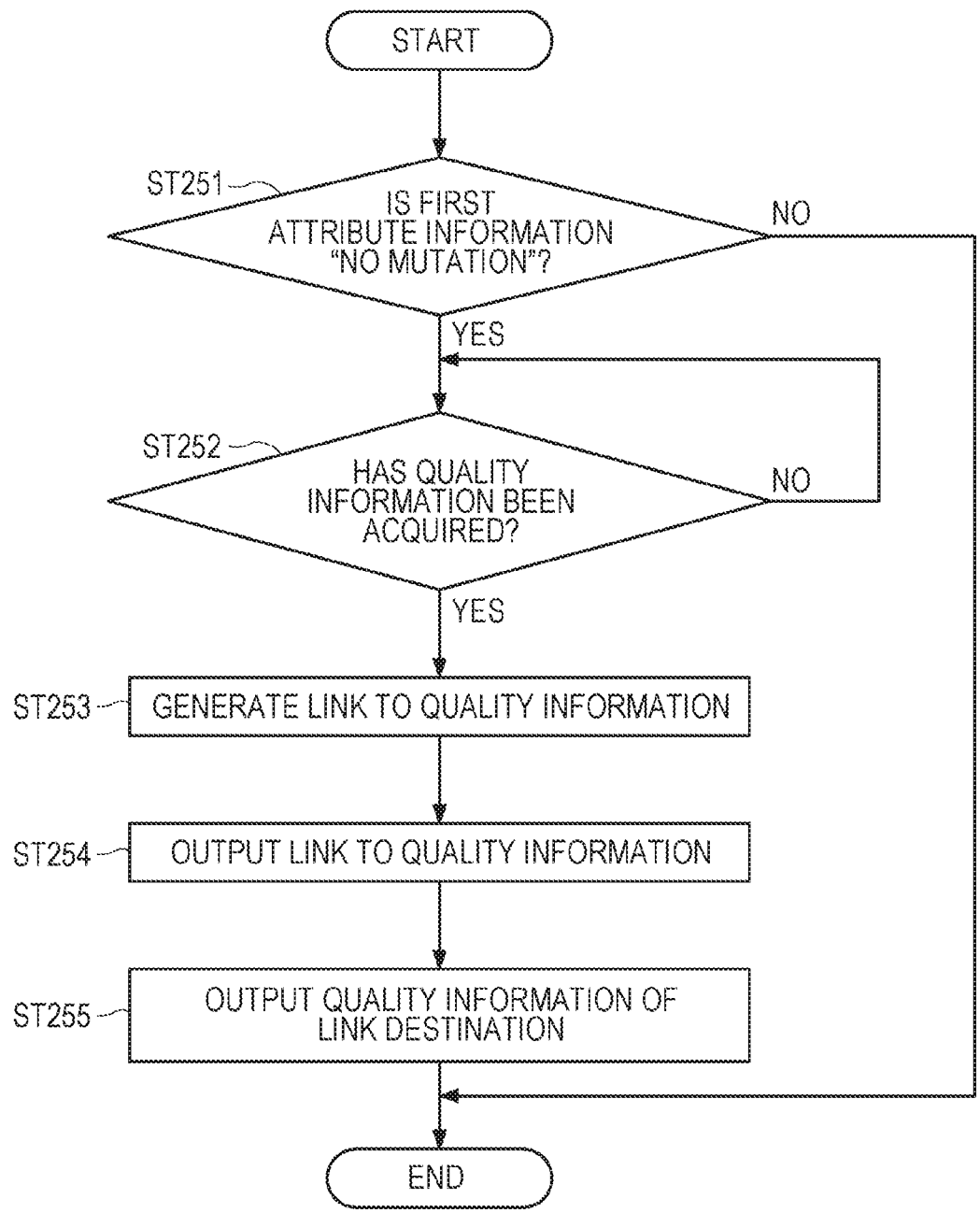
FIG. 60 is a flowchart of a process for displaying a link to quality information on the graphical user interface UI, in the integrated data management device A.

FIG. 60 shows a display process for the graphical user interface UI of FIG. 59 in the test request list output process of step ST43 shown in FIG. 20.

(5-1) Integrated Data Management Device Side

In step ST251 shown in FIG. 60, in the master table M corresponding to a test request ID of a patient to be examined in the expert meeting, the integrated data management device A determines whether or not there is a "no mutation" label indicating that there is no mutation in the "first attribute information" area of the master table M shown in FIG. 7.

In step ST251 shown in FIG. 60, when the integrated data management device A determines that there is the "no mutation" label (when "Yes"), the integrated data management device A proceeds to step ST252.

Next, in step ST252 of FIG. 60, the integrated data management device A confirms whether quality information of the test and the sample has been acquired, and the quality information of the test and the sample has been recorded in the "quality information" field of the master table M shown in FIG. 7.

When the quality information of the test and the sample has been acquired (when "Yes") in step ST252 of FIG. 60, the integrated data management device A proceeds to step ST253.

In step ST253, the integrated data management device A generates a link to the "quality information" field of the master table M shown in FIG. 7, in a "registered" label indicating that the quality information is registered, which is outputted in the "quality information" field of the test request list UI1 shown in FIG. 59. Association between the "quality information" field of the test request list UI1 and the "quality information" field of the master table M can be made with the test request ID or the sample ID corresponding to the test request ID.

In step ST254 of FIG. 60, the integrated data management device A outputs the "registered" label provided with the link generated in step ST253.

The integrated data management device A waits for access to the label provided with the link outputted in step ST254 from the expert meeting terminal C15 of the test facility C1 described later. Then, the integrated data management device A outputs quality information of the link destination in step ST255 of FIG. 60.

(5-2) Expert Meeting Terminal Side

At the expert meeting, quality of the gene panel testing is evaluated on the basis of the quality information, mainly by the clinical technologist T1 and the bioinformatician T20 at the test facility C1.

Figure 61:
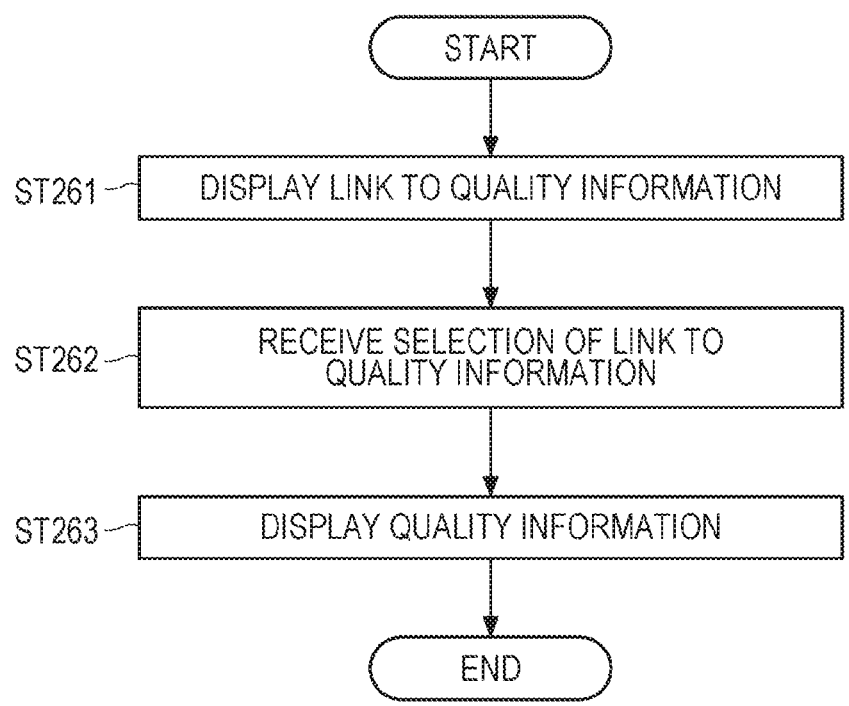
FIG. 61 shows a flowchart of a display process in the expert meeting terminal C15 of the test facility C1.

In step ST103 shown in FIG. 20, when the clinical technologist T1 and the bioinformatician T20 who participate in the expert meeting display quality information from the test request list UI1, in step ST261 shown in FIG. 61, the expert meeting terminal C15 of the test facility C1 uses browser software to display the "registered" label provided with the link outputted by the integrated data management device A in step ST254 of FIG. 60, in the quality information field of the test request list UI1 displayed on the output unit 107Y such as a display shown in FIG. 14.

In step ST262 shown in FIG. 61, the expert meeting terminal C15 of the test facility C1 receives selection of the label displayed in step ST254 of FIG. 60 from the input unit 106Y shown in FIG. 14. Input from the input unit 106Y is made by the clinical technologist T1 and the bioinformatician T20.

In step ST263 shown in FIG. 61, the expert meeting terminal C15 of the test facility C1 displays quality information of the link destination outputted by the integrated data management device A in step ST255 of FIG. 60.

(6) Link to External Database

When the second attribute information of "actionable mutation" or "other mutation" is given as a result of gene panel testing, information regarding a treatment method or the like may be examined from an external database, in an expert meeting, in accordance with a type of a gene in which a mutation has been detected, a site of the mutation, and the like.

In the test request list output process of step ST43 shown in FIG. 20, as shown in FIG. 62, the integrated data management device A may output fields of "result registration" indicating that the test result of the test request list UI1 has been registered, and of "information DB" displaying a link to an external information database (DB), in accordance with the second attribute information.

The "result registration" field indicates that the test result has been registered in the "test result" field of the master table M shown in FIG. 7. The "result registration" field displays the label "registered" provided with a link to the "test result" field of the master table M. The "result registration" field of the test request list UI1 shown in FIG. 62 and the "test result" field of the master table M shown in FIG. 7 are associated by the test request ID or the sample ID corresponding to the test request ID.

The "Information DB" field may display a "drug DB" label provided with a link to the drug information database server F11, a "clinical trial DB" label provided with a link to the clinical trial database server F21, and an "article DB" label provided with a link to the article database server F31, in accordance with the second attribute information.

By displaying such a link to an information database, a participant in the expert meeting can access information regarding mutation information of a gene of a patient to be examined from the test request list UI1, which improves convenience.

(6-1) Integrated Data Management Device Side

Figure 63:
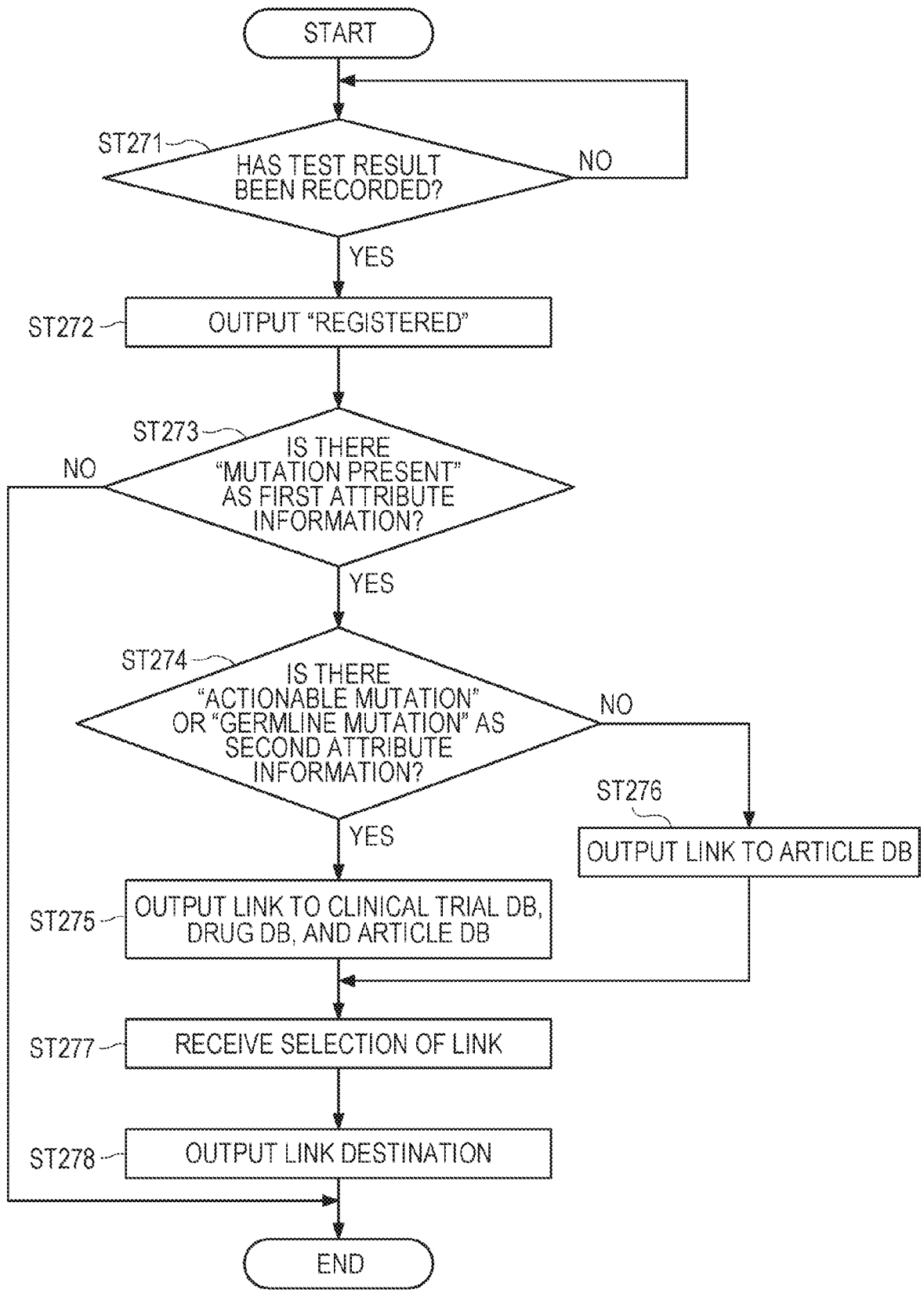
FIG. 63 shows a flowchart of a process for displaying a link to an external database on the graphical user interface UI, in the integrated data management device A.

FIG. 63 shows a generation process for a link to an external database and an output process for the link, in the integrated data management device A.

In step ST271 of FIG. 63, the integrated data management device A determines whether or not the test result has been recorded in the "test result" field of the master table M shown in FIG. 7.

When the "test result" is not recorded (when "No") in step ST271 of FIG. 63, the integrated data management device A waits until the "test result" is recorded in the master table M. This is because, since information search in the external database is performed based on a specific gene name or mutation site, it is not possible to perform the information search before a detailed test result is registered even if a link to an external database is displayed.

When the "test result" is recorded (when "Yes") in step ST271 of FIG. 63, the integrated data management device A proceeds to step ST272. Then, the integrated data management device A outputs the "registered" label to the "result registration" field of the test request list UI1 in FIG. 62.

Subsequently, the integrated data management device A proceeds to step ST273 of FIG. 63. Then, the integrated data management device A refers to the "first attribute information" field of the master table M shown in FIG. 7. When a "mutation present" label is included in the "first attribute information field" (when step ST273 in FIG. 63 is "YES"), the integrated data management device A proceeds to step ST274 in FIG. 63. When the "mutation present" label is not included in the "first attribute information field" (when step ST273 in FIG. 63 is "NO"), the integrated data management device A ends the process.

In step ST274 of FIG. 63, the integrated data management device A refers to the "second attribute information" of the master table M shown in FIG. 7. Then, the integrated data management device A determines whether or not there is a label of "actionable mutation" and/or "germline mutation" in the "second attribute information" field. In step ST274 of FIG. 63, when there is the label of "actionable mutation" and/or "germline mutation" (when "Yes"), the integrated data management device A proceeds to step ST275 in FIG. 63. Then, the integrated data management device A outputs labels of "drug DB" and "clinical trial DB". When there is no label of "actionable mutation" and/or "germline mutation" (when "No") in step ST274 of FIG. 63, a label of "other mutation" is given to the "second attribute information" field. In this case, the integrated data management device A proceeds to step ST276 in FIG. 63, to output the "article DB" label.

To the "drug DB", the "clinical trial DB", and the "article DB", URLs for accessing the corresponding servers are linked. The link of each database is stored in the integrated database OG of the integrated data management device A shown in FIG. 4.

The integrated data management device A waits for access from each expert meeting terminal to the "information DB" field of the test request list UI1 shown in FIG. 62. Then, the integrated data management device A receives selection of any of the "drug DB" label, the "clinical trial DB" label, or the "article DB" label in step ST277 shown in FIG. 63.

Subsequently, the integrated data management device A outputs a link destination of the selected label in step ST278 shown in FIG. 63.

(6-2) Expert Meeting Terminal Side

At the expert meeting, each participant refers to an external database.

In steps ST86 and ST103 shown in FIG. 20, each participant at the expert meeting accesses the external database from the test request list UI1 shown in FIG. 62.

Figure 64:
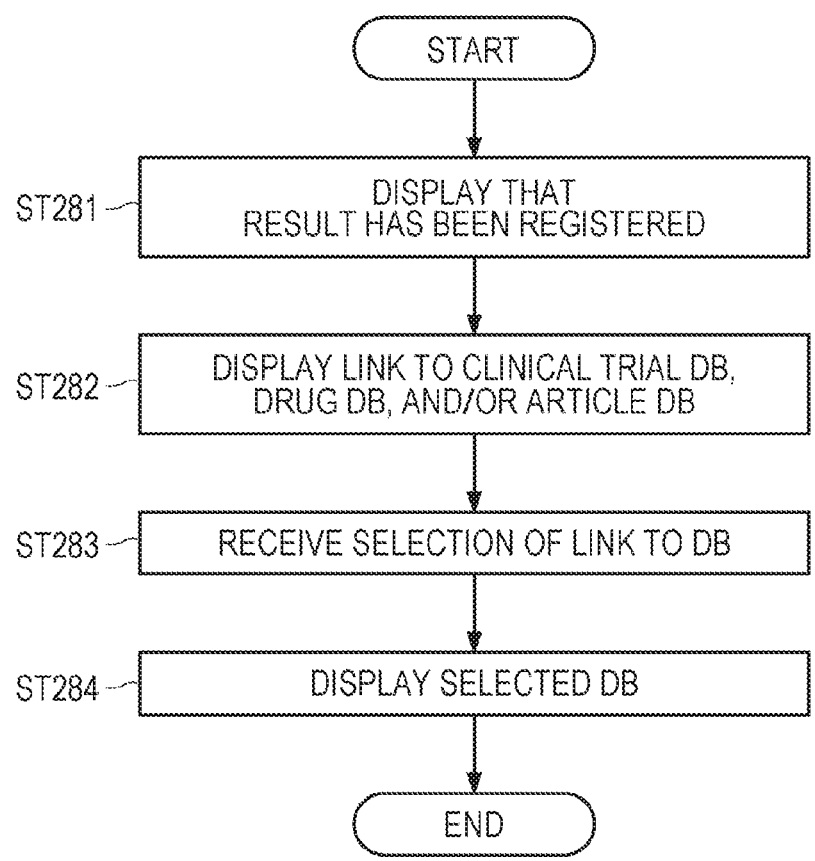
FIG. 64 shows a flowchart of a display process in the expert meeting terminal SP11 of an external facility SP1 and the bureau expert meeting terminal SP15.

In step ST281 shown in FIG. 64, each of the expert meeting terminals B15, B25, B35, C15, SP11, and SP15 uses browser software to display the "registered" label outputted by the integrated data management device A in step ST272 of FIG. 63, in the "result registration" field of the test request list UI1 displayed on the output units 107X, 107Y, and 107Z such as a display shown in FIG. 14.

In step ST282 shown in FIG. 64, each of the expert meeting terminals B15, B25, B35, C15, SP11, and SP15 uses the browser software to display the test request list UI1 including the label of "drug DB", "clinical trial DB", or "article DB" outputted in step ST275 or step ST276 in FIG. 63.

In step ST283 shown in FIG. 64, each of the expert meeting terminals B15, B25, B35, C15, SP11, and SP15 receives selection of the label displayed in step ST282 of FIG. 64, from the input unit 106X, 106Y, and 106Z shown in FIG. 14. Input from the input units 106X, 106Y, and 106Z is made by each participant in the expert meeting.

In step ST284 shown in FIG. 64, each of the expert meeting terminals B15, B25, B35, C15, SP11, and SP15 displays the external database of the link destination outputted by the integrated data management device A in step ST278 of FIG. 63.

9. Computer Program

The following steps may be executed on a computer as a computer program for managing a test request for gene panel testing: steps ST21 to ST38 shown in FIGS. 18 to 19, steps ST501 to ST504 shown in FIG. 30, steps ST601 to ST610 shown in FIG. 31, and steps ST321 to ST338 shown in FIGS. 55A to 55C; or steps ST21 to ST47 shown in FIGS. 18 to 21; steps ST501 to ST504 shown in FIG. 30; and steps ST601 to ST607 shown in FIG. 31; steps ST221 and ST222 shown in FIG. 37; steps ST241 to ST245 shown in FIG. 39; steps ST2411 to ST2416 shown in FIG. 41; steps ST2451 and ST2452 shown in FIG. 42; steps ST2461 to ST2468 shown in FIG. 44; steps ST901 to ST904 shown in FIG. 45; steps ST2471 to ST2474 shown in FIG. 46; steps ST351 to ST362 shown in FIG. 48; steps ST2481 to ST2484 shown in FIG. 49; steps ST451 to ST461 shown in FIG. 51, steps ST462 to ST466 shown in FIG. 52; steps ST911 to ST914 shown in FIG. 54; steps ST701 to ST705 shown in FIG. 56; steps ST711 to ST715 shown in FIG. 58; steps ST251 to ST255 shown in FIG. 60; and steps ST271 to ST278 shown in FIG. 63.

The computer program can be provided as a program product such as a storage medium. The computer program is stored in a storage medium such as a hard disk, a semiconductor memory device such as a flash memory, or an optical disk. A storage format of the program in the storage medium is not limited as long as the control unit can read the program. The storage in the storage medium is desirably non-volatile.

III. Other Processing and Modified Example (1) User Authentication Process at Test Request A description is given to an example of the test request process of step ST1 of FIG. 18 performed by the test request information acquisition unit 1B of the clinical information management device B10 shown in FIG. 11 mentioned in "Flow of test request" in 8-1 above. FIG. 65 shows a flow of a user authentication process of step ST1 of FIG. 18.

In step ST111 of FIG. 65, when the doctor in charge H1a makes a test request for gene panel testing with the clinical information management device B10, the doctor in charge H1a logs in to access the user interface UIa that is shown in FIG. 22 and stored in the integrated database OG of the integrated data management device A. The clinical information management device B10 receives, from the input unit 106B shown in FIG. 10, a processing start command by the doctor in charge H1a, that is, for example, selection of a URL of a gene panel testing request. Then, the clinical information management device B10 uses browser software to display a login screen on the output unit 107B such as a display shown in FIG. 10.

Subsequently, in step ST112 shown in FIG. 65, the clinical information management device B10 receives input of a user ID and a password by the doctor in charge H1a, from the input unit 106B shown in FIG. 10. Then, the clinical information management device B10 transmits the user ID and the password to the integrated data management device A.

The integrated database OG shown in FIG. 4 stores a login information table in which a user ID and a login password are recorded shown in FIG. 66. The integrated data management device A collates recorded information of this login information table with the information inputted in step ST112 of FIG. 65. When the collation is successful, the user interface UIa shown in FIG. 22 is outputted via the browser software.

In step ST113 in FIG. 65, the clinical information management device B10 receives the input of the test request information in step ST1 of FIG. 18 described in 8-1 above. Then, the clinical information management device B10 transmits the received test request information to the integrated data management device A.

(2) Modified Example of Test Request Screen

In inputting the test request information in step ST1 of FIG. 18, information on a request source facility, information related to a doctor in charge, information regarding a bureau that leads the expert meeting, and the like may be recorded in advance in the integrated database OG. In step ST113 of FIG. 65, it is possible to output, to a corresponding area, information regarding the information on the request source facility, the information related the doctor in charge, the information regarding the bureau that leads the expert meeting, and the like recorded in advance, in the user interface UIa shown in FIG. 22.

(3) Modified Example of Test Request ID Assignment

In the master table M shown in FIG. 7, the "test request ID" may be individually issued by a numbering system owned by a facility that has received the test request, or may be issued at will of a person in charge of the facility that has received the test request.

(4) Output Process for Specific Test Request

In step ST45 shown in FIG. 21, the integrated data management device A can set access authority to the test request list UI1 shown in FIG. 9 according to a user ID, a group ID, and a role ID, to limit display of the individual test request display area UI3 stored in the master table M in accordance with the ID. For one individual test request display area UI3, display of each area displayed in the test request list UI1 can also be changed in accordance with the access authority.

(5) Modified Example of Test Request List

In the test request list shown in FIG. 9, the attribute information may be discernibly displayed for every attribute information. The "discernible" may be represented by changing a display color of a label for every attribute information. The attribute information may be represented by an identification symbol such as an alphabet such as "A", "G", and "O". In a display example, a reference symbol SM is represented in FIG. 9.

Specific attribute information (such as no mutation) may be displayed with a common symbol (for example, "!") for calling attention.

The identification by the common symbol for calling attention and the color of the label may be displayed when a label different from progress of a normal test is given to the "test status" of the test request list, for example, when "sample reacquisition", "test stop", or the like is recorded.

The test request list may be displayed in accordance with priority of the attribute information, by setting the priority in advance for every attribute information in the test request list.

(6) Temporary Reservation for Meeting

In step ST235 shown in FIG. 38, the example in which the doctor in charge H1a selects a schedule has been described. However, as another embodiment, for example, before the result of the gene panel testing is obtained, the doctor in charge H1a can use the dialog UI51 shown in FIG. 3A, the dialog UI52 shown in FIG. 3B, the dialog UI55 shown in FIG. 43D, the dialog UI56 shown in FIG. 43E, the dialog UI57 shown in FIG. 47D, the dialog UI58 shown in FIG. 47E, or the dialog UI60 shown in FIG. 53D, to temporarily reserve the setting for the expert meeting. The temporary reservation is made by each doctor in charge selecting the "set" icon in each dialog, in the dialog UI51 shown in FIG. 3A, the dialog UI52 shown in FIG. 3B, the dialog UI55 shown in FIG. 43D, the dialog UI56 shown in FIG. 43E, the dialog UI57 shown in FIG. 47D, the dialog UI58 shown in FIG. 47E, or the dialog UI60 shown in FIG. 53D. With the temporary reservation, a label indicating "temporarily reserved" may be displayed in the "setting status" field of the test request list UI1 shown in FIG. 67. The "temporarily reserved" label has a link to dialog UI7 shown in FIG. 68. When the doctor in charge H1a selects the "temporarily reserved" label, for example, the dialog UI7 is displayed on the output unit 107X of the expert meeting terminal B15 of the medical facility B1. For confirming the reservation, the expert meeting is regularly set by the doctor in charge H1a selecting a meeting notification icon UI77, and the "set" label is displayed in the "setting status" field of the test request list UI1. With the regular setting, the schedule of the expert meeting can be transmitted by mail to each participant in the expert meeting.

(7) Modified Example of Dialog

The dialog UI7 shown in FIG. 68 may display an area UI71 that displays patient identification information for identification of the patient, such as a patient name, gender, a date of birth, and the like, an area UI73 that displays a list of members who participate in the expert meeting, an area UI75 for schedule setting of the expert meeting, and the meeting notification icon UI77 that receives selection by the doctor in charge H1a to confirm the setting and notify each participant in the meeting by mail that the meeting has been set.

The patient name, the gender, the date of birth, and the like are read from a corresponding area in the master table M shown in FIG. 7. The list of members who participate in the expert meeting is read from the expert meeting group table GT (FIG. 8B) linked to the area of "group ID" of the master table M shown in FIG. 7. In the dialog UI7, the area UI75 for schedule setting of the expert meeting may display, a candidate schedule displayed in the dialog UI51 shown in FIG. 3A, the dialog UI52 shown in FIG. 3B, the dialog UI55 shown in FIG. 43D, the dialog UI56 shown in FIG. 43E, the dialog UI57 shown in FIG. 47D, the dialog UI58 shown in FIG. 47E, or the dialog UI60 shown in FIG. 53D.

(8) Meeting Time and Required Time

The meeting time and the required time shown in 1. to 8. above are examples and can be set as appropriate. However, the second required time is shorter than the first required time.

(9) Variation for Determining Required Time for Meeting

In 8-3. above, an example has been shown in which the required time for the meeting is determined based on the number of mutations and a mutation type, but the required time for the meeting may be determined with information indicating clinical significance. For example, in (6) of 8-3. above, in the mutation type, a link is provided to information indicating clinical significance of a gene mutation detected by gene panel testing such as, drug information, clinical trial information, and article information. Also in the report shown in FIG. 33 described in (3) of 8-3. above, information indicating clinical significance is described as additional information. Therefore, for example, in pattern 4 shown in 8-3. (3-4) above, the additional time ID may be given instead of a predetermined gene mutation on the basis of the information indicating the clinical significance, for example. When clinical trial information and/or article information is assigned to the information indicating clinical significance, the additional time ID "C" can be desirably attached.

(10) Test Result for Setting Expert Meeting Time

In the 8-3. above, a description has been given to the process of outputting a candidate schedule of the expert meeting on the basis of the attribute information acquired by the test information management device C11 in step ST71 shown in FIG. 19. However, for example, the integrated data management device A may output a candidate schedule of the expert meeting on the basis of a test result described in the report received in step ST37 shown in FIG. 19. The report shown in FIG. 33 includes the gene mutation information area DT1 and the germline mutation information area DT2. The additional information area AP in which information indicating clinical significance is described is also provided. Therefore, information indicating the number of mutations, the mutation type, and clinical significance can be acquired by the integrated data management device A reading information indicating what kind of gene mutation is included in these areas, the number of mutations, and the clinical significance. The integrated data management device A can also use the determination table H shown in FIG. 32B to determine the number of mutations and the mutation type. The subsequent processing is as described in 8-3 above.

(11) Modified Example 1 of System 1000

In the above-mentioned embodiment, the integrated data management device A acquires test request information from the clinical information management devices B10, B20, and B30, and acquires the attribute information from the test information management device C11. However, these pieces of information may be acquired from a same computer. For example, the clinical information management devices B10, B20, and B30 may transmit the test request information to the test information management device C11, and the test information management device C11 may transmit the test request information and the attribute information to the integrated data management device A.

(12) Modified Example 2 of System 1000

The integrated data management device A may be a web server that provides cloud computing. The clinical information management device B10, the expert meeting terminal B15, the clinical information management device B20, the expert meeting terminal B25, the clinical information management device B30, and the expert meeting terminal B35 may access the integrated data management device A, which is a web server, via a web browser. That is, the system 1000 may be a cloud computing system that does not require a dedicated application to access the integrated data management device A.

What is claimed is:

1. A method for supporting a first and a second expert meeting for interpretation of genetic information of at least a first patient and a second patient by a plurality of medical persons by a computer, comprising:
    acquiring a first test result of gene panel testing that analyzes genetic information of the first patient;
    acquiring a second test result of gene panel testing that analyzes genetic information of the second patient;
    determining that the first test result indicates a presence of a gene mutation in the first patient;
    determining that the second test result indicates an absence of a gene mutation in the second patient;
    determining that a first required time duration for the first expert meeting corresponds to a first preset time duration length in response to determining that the first test result indicates the presence of the gene mutation in the first patient;
    determining that a second required time duration for the second expert meeting corresponds to a second preset time duration length in response to determining that the second test result indicates the absence of a gene mutation in the second patient, wherein the first preset time duration length is longer than the second preset time duration length;
    outputting an operation screen that enables schedule setting of the first expert meeting and the second expert meeting, based on the first required time duration of the first expert meeting and the second required time duration of the second expert meeting; and
    executing the schedule setting by receiving a selection of at least one candidate schedule in a selection area comprised in the at least one candidate schedule that are displayed on the operation screen and subsequently receiving a confirmation of the selection of the at least one candidate schedule on the operation screen.

2. The method according to claim 1, wherein
the one or more candidate schedules comprise:
    information indicating the first required time duration for the first expert meeting according to the first test result, or
    information indicating the second required time duration for the second expert meeting according to the second test result; and
    a candidate date.

3. The method according to claim 2, wherein the information indicating the first or second required time duration is at least one selected from start time and end time of the expert meeting, time duration required for the expert meeting, and a label indicating time duration required for the expert meeting.

4. The method according to claim 1, wherein
    the first test result comprises at least one selected from a number of detected gene mutations and a type of a gene mutation that has been detected.

5. The method according to claim 4, wherein the first required time duration for the first expert meeting according to the first test result varies depending on the type of the gene mutation that has been detected.

6. The method according to claim 4, wherein
    the type of the gene mutation comprises at least one selected from an actionable mutation and a germline mutation.

7. The method according to claim 4, wherein the first required time duration for the first expert meeting according to the first test result varies depending on a number of detected gene mutations.

8. The method according to claim 1, wherein
    the first test result comprises information indicating clinical significance for a gene mutation detected in the gene panel testing, and
    wherein determining that the first required time duration corresponds to the first preset time duration length also based at least in part on the information indicating clinical significance.

9. The method according to claim 8, wherein
    the information indicating clinical significance comprises at least one selected from drug information, clinical trial information, and article information corresponding to the gene mutation.

10. The method according to claim 1, further comprising, adjusting an order of holding a plurality of expert meetings including the first and second expert meetings based on information inputted through the operation screen and based on a predetermined rule.

11. The method according to claim 10, wherein the predetermined rule comprises adjusting an order of holding the plurality of expert meetings, based on a length of meeting time or priority of holding a meeting.

12. The method according to claim 1, further comprising, accepting a schedule change of the first or second expert meeting that has been set based on information inputted via the operation screen.

13. A support device for supporting a first and a second expert meeting for interpretation of genetic information of at least a first patient and a second patient by a plurality of medical persons, comprising:
a control unit configured to:
acquire a first test result of gene panel testing that analyzes genetic information of the first patient;
acquire a second test result of gene panel testing that analyzes genetic information of the second patient;
determine that the first test result indicates a presence of a gene mutation in the first patient;
determine that the second test result indicates an absence of a gene mutation in the second patient;
determine that a first required time duration for the first expert meeting corresponds to a first preset time duration length in response to determining that the first test result indicates the presence of the gene mutation in the first patient;
determine that a second required time duration for the second expert meeting corresponds to a second preset time duration length in response to determining that the second test result indicates the absence of a gene mutation in the second patient, wherein the first preset time duration length is longer than the second preset time duration length;
output an operation screen that enables schedule setting of the first expert meeting and the second expert meeting, based on the first required time duration of the first expert meeting and the second required time duration of the second expert meeting; and
execute the schedule setting by receiving a selection of at least one candidate schedule in a selection area comprised in the at least one candidate schedule that are displayed on the operation screen and subsequently receiving a confirmation of the selection of the at least one candidate schedule on the operation screen.

14. A computer-readable medium having stored therein a computer program for supporting a first and a second expert meeting for interpretation of genetic information of at least a first patient and a second patient by a plurality of medical persons, wherein, when executed by a computer, the computer program causes the computer to perform a method comprising:
acquiring a first test result in gene panel testing that analyzes genetic information of the first patient;
acquiring a second test result in gene panel testing that analyzes genetic information of the second patient;
determining that the first test result indicates a presence of a gene mutation in the first patient;
determining that the second test result indicates an absence of a gene mutation in the second patient;
determining that a first required time duration for the first expert meeting corresponds to a first preset time duration length in response to determining that the first test result indicates the presence of the gene mutation in the first patient;
determining that a second required time duration for the second expert meeting corresponds to a second preset time duration length in response to determining that the second test result indicates the absence of a gene mutation in the second patient, wherein the first preset time duration length is longer than the second preset time duration length;
outputting an operation screen that enables schedule setting of the first expert meeting and the second expert meeting, based on the first required time duration of the first expert meeting and the second required time duration of the second expert meeting; and
executing the schedule setting by receiving a selection of at least one candidate schedule in a selection area comprised in the at least one candidate schedule that are displayed on the operation screen and subsequently receiving a confirmation of the selection of the at least one candidate schedule on the operation screen.

15. A support system for supporting a first and a second expert meeting for interpretation of genetic information of at least a first patient and a second patient by a plurality of medical persons, the support system comprising:
a support device comprising a control unit; and
one or more other computers,
wherein
the control unit of the support device is configured to:
acquire a first test result of gene panel testing that analyzes genetic information of the first patient;
acquire a second test result of gene panel testing that analyzes genetic information of the second patient;
determine that the first test result indicates a presence of a gene mutation in the first patient;
determine that the second test result indicates an absence of a gene mutation in the second patient;
determine that a first required time duration for the first expert meeting corresponds to a first preset time duration length in response to determining that the first test result indicates the presence of the gene mutation in the first patient;
determine that a second required time duration for the second expert meeting corresponds to a second preset time duration length in response to determining that the second test result indicates the absence of a gene mutation in the second patient, wherein the first preset time duration length is longer than the second preset time duration length; and
output an operation screen that enables schedule setting of the first expert meeting and the second expert meeting, based on the first required time duration of the first expert meeting and the second required time duration of the second expert meeting, to the one or more other computers, and
the one or more other computers is configured to:
acquire and display the operation screen; and
execute the schedule setting by receiving a selection of at least one candidate schedule in a selection area comprised in the at least one candidate schedule that are displayed on the operation screen and subsequently receiving a confirmation of the selection of the at least one candidate schedule on the operation screen.

* * * * *